US008389241B2

(12) United States Patent
Hara et al.

(10) Patent No.: US 8,389,241 B2
(45) Date of Patent: Mar. 5, 2013

(54) ENZYME THAT CATALYZES A PEPTIDE-FORMING REACTION FROM A CARBOXY COMPONENT AND AN AMINE COMPONENT, MICROBE PRODUCING THE SAME, AND A METHOD OF PRODUCING A DIPEPTIDE USING THE ENZYME OR MICROBE

(75) Inventors: Seiichi Hara, Kawasaki (JP); Kenzo Yokozeki, Kawasaki (JP); Isao Abe, Kawasaki (JP); Naoto Tonouchi, Kawasaki (JP); Yasuko Jojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/611,827

(22) Filed: Sep. 12, 2012

(65) Prior Publication Data
US 2013/0011873 A1 Jan. 10, 2013

Related U.S. Application Data

(60) Division of application No. 13/211,834, filed on Aug. 17, 2011, which is a division of application No. 12/729,656, filed on Mar. 23, 2010, now Pat. No. 8,039,232, which is a division of application No. 11/841,151, filed on Aug. 20, 2007, now Pat. No. 7,736,871, which is a division of application No. 10/855,533, filed on May 28, 2004, now Pat. No. 7,288,389, which is a continuation of application No. PCT/JP03/09468, filed on Jul. 25, 2003.

(30) Foreign Application Priority Data

Jul. 26, 2002 (JP) ................................ 2002-218957
Jan. 24, 2003 (JP) ................................ 2003-016765

(51) Int. Cl.
*C12P 21/06* (2006.01)
*C12N 9/00* (2006.01)
*C12N 1/20* (2006.01)
*C12N 15/00* (2006.01)
*C07H 21/04* (2006.01)

(52) U.S. Cl. .................... 435/69.1; 435/183; 435/252.3; 435/320.1; 536/23.2

(58) Field of Classification Search .................... None
See application file for complete search history.

(56) References Cited

U.S. PATENT DOCUMENTS

| 7,288,389 | B2 | 10/2007 | Hara et al. |
| 7,338,780 | B2 | 3/2008 | Yokozeki et al. |
| 7,361,458 | B2 | 4/2008 | Yokozeki et al. |
| 7,736,871 | B2 | 6/2010 | Hara et al. |
| 8,039,232 | B2 | 10/2011 | Hara et al. |
| 2004/0204577 | A1 | 10/2004 | Hara et al. |
| 2008/0050773 | A1 | 2/2008 | Hara et al. |
| 2008/0274530 | A1 | 11/2008 | Hara et al. |

FOREIGN PATENT DOCUMENTS

| EP | 0 278 787 | 8/1988 |
| EP | 0 359 399 | 3/1990 |
| JP | 53-92729 | 8/1978 |
| JP | 1-96194 | 4/1989 |
| JP | 6-234715 | 8/1994 |
| JP | 2000-78971 | 3/2000 |
| WO | WO 90/01555 | 2/1990 |
| WO | WO 99/61050 | 12/1999 |
| WO | WO 00/58478 | 10/2000 |
| WO | WO 01/70937 A1 | 9/2001 |
| WO | WO 03/010187 | 2/2003 |
| WO | WO 03/010189 | 2/2003 |
| WO | WO 03/010307 | 2/2003 |

OTHER PUBLICATIONS

F. Krieg, et al., "Enzymatic Peptide Synthesis by the Recombinant Proline-Specific Endopeptidase from *Flavobacterium meningosepticum* and Its Mutationally Altered CYS-556 Variant", Appl Microbiol Biotechnol, 1995, 42, pp. 844-852.
P. Vandamme, et al., "New Perspectives in the Classification of the Flavobacteria: Description of *Chryseobacterium* Gen. Nov., Bergeyella Gen. Nov., and Empedobacter Nom. Rev.", International Journal of Systematic Bacteriology, vol. 44, No. 4, Oct. 1994, pp. 827-831, XP-009050959.
J.J. Polderman-Tijmes, et al., "Cloning Sequence Analysis, and Expression in *Escherichia coli* of the Gene Encoding an Alpha-Amino Acid Ester Hydrolase From Acetobacter Turbidans", Applied and Enviromental Microbiology, vol. 68, No. 1, Jan. 2002, pp. 211-218, XP-001121414.
Guo, et al. Protein tolerance to random amino acid change, PNAS, 101/25, 9205-9210, 2004.
S. Akabori, et al., "Protection of Amide-Nitrogen for Peptide Synthesis. A Novel Synthesis of Peptides Containing C-Terminal Glutamine", Bull. Chem. Soc. Jpn., 34, May 1961, p. 739.
Y. Shimonishi, et al., "Studies on the Synthesis of Peptides Containing Glutamine As the C-Terminal. I. Protection of Amide-Nitrogen With Xanthyl Group During Peptide Synthesis", Bull. Chem. Soc. Jpn., vol. 35, No. 12, Dec. 1962, pp. 1966-1970.
Y. Shimonishi, "Studies of the Synthesis of Peptides Containing C-Terminal Glutamine. II. The Synthesis and Use of Alpha-P-Nitrobenzyl Gamma-Methyl L-Glutamate", Bull. Chem. Soc. Jpn., vol. 37, No. 2, Feb. 1964, pp. 200-203.
K. Morihara, et al., "Alpha-Chymotrypsin as the Catalyst for Peptide Synthesis", Biochem. J., 1977, 163, pp. 531-542.

(Continued)

*Primary Examiner* — Christian Fronda
(74) *Attorney, Agent, or Firm* — Oblon, Spivak, McClelland, Maier & Neustadt, L.L.P.

(57) ABSTRACT

DNA and recombinant DNA that encode a peptide-forming enzyme, a method for producing a peptide-forming enzyme, and a method for producing a dipeptide are disclosed. A method for producing a dipeptide includes producing a dipeptide from a carboxy component and an amine component by using a culture of a microbe belonging to the genus *Sphingobacterium* and having the ability to form the dipeptide from the carboxy component and the amine component, a microbial cell separated from the culture, treated microbial cell product of the microbe or a peptide-forming enzyme derived from the microbe.

11 Claims, 4 Drawing Sheets

OTHER PUBLICATIONS

Peter M. Howley, et al., "A Rapid Method for Detecting and Mapping Homology Between Heterologous DNAs", The Journal of Biological Chemistry, vol. 254, No. 11, Jun. 10, 1979, pp. 4876-4883.

Anshul Dubey, et al., "Identifying the Interacting Positions of a Protein Using Boolean Learning and Support Vector Machines", Computational Biology and Chemistry, 30, 2006, pp. 268-279.

Office Action issued Nov. 18, 2010, in Argentinean Patent Application No. P040100093 (with English translation).

Extended European Search Report issued on Apr. 5, 2011 in corresponding European Application No. 10 00 9020.

"LERGA83TR LERG *Arabidopsis thaliana* Genomic Clone LERGA83, Genomic Survey Sequence", EMBL Database Online, EMBL: AQ961701, XP 002624560, 1 Page.

ENZYME THAT CATALYZES A PEPTIDE-FORMING REACTION FROM A CARBOXY COMPONENT AND AN AMINE COMPONENT, MICROBE PRODUCING THE SAME, AND A METHOD OF PRODUCING A DIPEPTIDE USING THE ENZYME OR MICROBE

CROSS-REFERENCE TO RELATED APPLICATIONS

The present application is a divisional application of U.S. Ser. No. 13/211,834, filed Aug. 17, 2011, which is a divisional application of U.S. Ser. No. 12/729,656, filed Mar. 23, 2010, which is a divisional application of U.S. Ser. No. 11/841,151, filed on Aug. 20, 2007, which is a divisional application of U.S. Ser. No. 10/855,533, filed on May 28, 2004, which is a continuation of PCT/JP03/09468 filed on Jul. 25, 2003, which claims priority to JP 2003-16765, filed on Jan. 24, 2003, and to JP 2002-218957, filed on Jul. 26, 2002.

TECHNICAL FIELD

The present invention relates to a novel enzyme that can form a peptide easily, at high yield and inexpensively without going through a complex synthetic method. More particularly, the present invention relates to a novel enzyme that catalyzes a peptide-forming reaction from a carboxy component and an amine component, to a microbe that produces the enzyme, and to a method for producing dipeptide using this enzyme or microbe.

BACKGROUND ART

Peptides are used in the fields of pharmaceuticals, foods and various other fields. For example, since L-alanyl-L-glutamine has higher stability and water-solubility than L-glutamine, it is widely used as a component of fluid infusion and serum-free media.

Chemical synthesis methods, which have been known as methods for producing peptides, are not always easy. Known examples of such methods include a method that uses N-benzyloxycarbonylalanine (hereinafter, "Z-alanine") and protected L-glutamine (see Bull. Chem. Soc. Jpn., 34, 739 (1961), Bull. Chem. Soc. Jpn., 35, 1966 (1962)), a method that uses Z-alanine and protected L-glutamic acid-γ-methyl ester (see Bull. Chem. Soc. Jpn., 37, 200 (1964)), a method that uses Z-alanine ester and unprotected glutamic acid (see Japanese Patent Application Laid-open Publication No. H1-96194), a method that involves synthesis of an N-(2-substituted)-propionyl glutamine derivative as an intermediate from a 2-substituted-propionyl halide as a raw material (see Patent Application Laid-open Publication No. H6-234715).

However, since all these methods require the introduction and elimination of protecting groups or the use of an optically active intermediate, they are not considered to be adequately satisfactory in terms of their industrial advantages.

On the other hand, widely known examples of typical peptide production methods using enzymes consist of a condensation reaction that uses an N-protected and C-unprotected carboxy component and an N-unprotected, C-protected amine component (hereinafter, "Reaction 1"), and a substitution reaction that uses an N-protected, C-protected carboxy component and an N-unprotected, C-protected amine component (hereinafter, "Reaction 2"). An example of Reaction 1 is a method for producing Z-aspartylphenylalanine methyl ester from Z-aspartic acid and phenylalanine methyl ester (see Japanese Patent Application Laid-open Publication No. S53-92729), while an example of Reaction 2 is a method for producing acetylphenylalanylleucine amide from acetylphenylalanine ethyl ester and leucine amide (see Biochemical J., 163, 531 (1977)). There have been reported very few research examples of method that uses an N-unprotected, C-protected carboxy component. An example of a substitution reaction that uses an N-unprotected, C-protected carboxy component and an N-unprotected, C-protected amine component (hereinafter, "Reaction 3") is described in International Patent Publication WO 90/01555. For example, a method for producing arginylleucine amide from arginine ethyl ester and leucine amide may be mentioned of. Examples of substitution reactions that use an N-unprotected, C-protected carboxy component and an N-unprotected, C-unprotected amine component (hereinafter, "Reaction 4") are described in European Patent Publication EP 278787A1 and European Patent Publication EP 359399B1. For example, a method for producing tyrosylalanine from tyrosine ethyl ester and alanine may be mentioned of.

DISCLOSURE OF THE INVENTION

The most inexpensive production method among the aforementioned methods of Reactions 1 to 4 naturally falls within the class of Reaction 4, which involves the fewest protecting groups.

However, the example of Reaction 4 of the prior art (see European Patent Publication EP 278787A1) had the following major problems: (1) extremely slow rate of peptide production, (2) low peptide production yield, (3) the peptides that can be produced are limited to those that contain amino acids with comparatively high hydrophobicity, (4) the amount of enzyme added is extremely large, and (5) comparatively expensive carboxypeptidase preparations derived from molds, yeasts or plants are required. In the Reaction 4, there is no method known whatsoever that uses an enzyme derived from bacteria or yeasts other than the genus *Saccharomyces*, and there are no known method for producing alanylglutamine and other peptides that are highly hydrophilic. In consideration of this background, there is a need to develop an industrially inexpensive method for producing these peptides.

It is an object of the present invention to provide a novel enzyme that can form a peptide easily, at high yield and inexpensively without going through a complex synthesis method. More particularly, an object of the present invention is to provide a novel enzyme that catalyzes a peptide-forming reaction from a carboxy component and an amine component, a microbe that produces the enzyme, and a method for inexpensively producing a peptide using this enzyme or microbe.

As a result of conducting extensive research in consideration of the above object, the inventors of the present invention have found a novel enzyme that efficiently forms a peptide from newly discovered bacteria belonging to the genus *Empedobacter*, etc. and determined the sequence of this enzyme gene, thereby leading to completion of the present invention.

Namely, the present invention is as described below.

[1] A DNA encoding a protein selected from the group consisting of (A), (C), (E), (G), (I), (K), (M), (O), (Q), (S), (U), and (W), wherein the protein has an amino acid sequence defined as follows:

(A) an amino acid sequence consisting of amino acid residue numbers 23 to 616 of SEQ ID NO:6, (C) an amino acid sequence consisting of amino acid residue numbers 21 to 619 of SEQ ID NO:12,
(E) an amino acid sequence consisting of amino acid residue numbers 23 to 625 of SEQ ID NO:18,
(G) an amino acid sequence consisting of amino acid residue numbers 23 to 645 of SEQ ID NO:23,
(I) an amino acid sequence consisting of amino acid residue numbers 26 to 620 of SEQ ID NO:25,
(K) an amino acid sequence consisting of amino acid residue numbers 18 to 644 of SEQ ID NO:27,
(M) an amino acid sequence consisting of SEQ ID NO:6,
(O) an amino acid sequence consisting of SEQ ID NO:12,
(Q) an amino acid sequence consisting of SEQ ID NO:18,
(S) an amino acid sequence consisting of SEQ ID NO:23,
(U) an amino acid sequence consisting of SEQ ID NO:25, or
(W) an amino acid sequence consisting of SEQ ID NO:27,
[2] A recombinant DNA including the DNA according to [1] above.
[3] A transformed cell including the recombinant DNA according to [2] above.
[4] A method for producing a peptide-forming enzyme including:
culturing the transformed cell according to [3] above in a medium for a time and under conditions suitable to produce the peptide-forming enzyme, and
accumulating the peptide-forming enzyme in the medium and/or transformed cell.
[5] A method for producing a dipeptide including:
culturing the transformed cell according to [3] in a medium for a time and under conditions suitable to produce a peptide-forming enzyme in a culture, and
mixing the culture with a carboxy component and an amine component to synthesize a dipeptide by enzymatic catalysis facilitated by a peptide-forming enzyme encoded by the DNA.
[6] The method for producing a dipeptide according to [5] above, wherein the cell is a microbe belonging to the genus *Sphingobacterium* that has an ability to form the dipeptide from the carboxy component and the amine component.
[7] The method for producing a dipeptide according to [6] above, wherein the cell is separated from the culture.
[8] The method for producing a dipeptide according to [6] above, wherein the cell is a treated microbial cell product of the microbe.
[9] A DNA encoding a protein selected from the group consisting of (B), (D), (F), (H), (J), (L), (N), (P), (R), (T), (V), and (X), wherein the protein has an amino acid sequence defined as follows:
(B) an amino acid sequence including substitution, deletion, insertion, addition, and/or inversion of one or a plurality of amino acids in amino acid residue numbers 23 to 616 of SEQ ID NO:6, and has at least 50% of the peptide-forming activity of a protein corresponding to unmutated amino acid residue numbers 23 to 616 of SEQ ID NO:6 at 50° C. and a pH of 8,
(D) an amino acid sequence including substitution, deletion, insertion, addition, and/or inversion of one or a plurality of amino acids in amino acid residue numbers 21 to 619 of SEQ ID NO:12, and has at least 50% of the peptide-forming activity of a protein corresponding to unmutated amino acid residue numbers 21 to 619 of SEQ ID NO:12 at 50° C. and a pH of 8,
(F) an amino acid sequence including substitution, deletion, insertion, addition, and/or inversion of one or a plurality of amino acids in amino acid residue numbers 23 to 625 of SEQ ID NO:18, and has at least 50% of the peptide-forming activity of a protein corresponding to unmutated amino acid residue numbers 23 to 625 of SEQ ID NO:18 at 50° C. and a pH of 8,
(H) an amino acid sequence including substitution, deletion, insertion, addition, and/or inversion of one or a plurality of amino acids in amino acid residue numbers 23 to 645 of SEQ ID NO:23, and has at least 50% of the peptide-forming activity of a protein corresponding to unmutated amino acid residue numbers 23 to 645 of SEQ ID NO:23 at 50° C. and a pH of 8,
(J) an amino acid sequence including substitution, deletion, insertion, addition, and/or inversion of one or a plurality of amino acids in amino acid residue numbers 26 to 620 of SEQ ID NO:25, and has at least 50% of the peptide-forming activity of a protein corresponding to unmutated amino acid residue numbers 26 to 620 of SEQ ID NO:25 at 50° C. and a pH of 8,
(L) an amino acid sequence including substitution, deletion, insertion, addition, and/or inversion of one or a plurality of amino acids in amino acid residue numbers 18 to 644 of SEQ ID NO:27, and has at least 50% of the peptide-forming activity of a protein corresponding to unmutated amino acid residue numbers 18 to 644 of SEQ ID NO:27 at 50° C. and a pH of 8,
(N) a mature protein region, having an amino acid sequence including substitution, deletion, insertion, addition, and/or inversion of one or a plurality of amino acids in an amino acid sequence consisting of SEQ ID NO:6, and has at least 50% of the peptide-forming activity of a protein corresponding to unmutated SEQ ID NO:6 at 50° C. and a pH of 8,
(P) a mature protein region, having an amino acid sequence including substitution, deletion, insertion, addition, and/or inversion of one or a plurality of amino acids in an amino acid sequence consisting of SEQ ID NO:12, and has at least 50% of the peptide-forming activity of a protein corresponding to unmutated SEQ ID NO:12 at 50° C. and a pH of 8,
(R) a mature protein region, having an amino acid sequence including substitution, deletion, insertion, addition, and/or inversion of one or a plurality of amino acids in an amino acid sequence consisting of SEQ ID NO:18, and has at least 50% of the peptide-forming activity of a protein corresponding to unmutated SEQ ID NO:18 at 50° C. and a pH of 8,
(T) a mature protein region, having an amino acid sequence including substitution, deletion, insertion, addition, and/or inversion of one or a plurality of amino acids in an amino acid sequence consisting of SEQ ID NO:23, and has at least 50% of the peptide-forming activity of a protein corresponding to unmutated SEQ ID NO:23 at 50° C. and a pH of 8,
(V) a mature protein region, having an amino acid sequence including substitution, deletion, insertion, addition, and/or inversion of one or a plurality of amino acids in an amino acid sequence consisting of SEQ ID NO:25, and has at least 50% of the peptide-forming activity of a protein corresponding to unmutated SEQ ID NO:25 at 50° C. and a pH of 8, or
(X) a mature protein region, having an amino acid sequence including substitution, deletion, insertion, addition, and/or inversion of one or a plurality of amino acids in an amino acid sequence consisting of SEQ ID NO:27, and has at least 50% of the peptide-forming activity of a protein corresponding to unmutated SEQ ID NO:27 at 50° C. and a pH of 8.
[10] The DNA according to [9] above, wherein the plurality is 2 to 50 amino acid residues.
[11] A recombinant DNA including the DNA according to [9] above.

[12] A transformed cell including the recombinant DNA according to [11] above.

[13] A method for producing a peptide-forming enzyme including:
culturing the transformed cell according to [12] above, in a medium for a time and under conditions suitable to produce the peptide-forming enzyme, and
accumulating the peptide-forming enzyme in the medium and/or transformed cell.

[14] A method for producing a dipeptide including:
culturing the transformed cell according to [12] above in a medium for a time and under conditions suitable to produce a peptide-forming enzyme in a culture, and
mixing the culture with a carboxy component and an amine component to synthesize a dipeptide by enzymatic catalysis facilitated by a peptide-forming enzyme encoded by the DNA.

[15] The method for producing a dipeptide according to [14] above, wherein the cell is a microbe belonging to the genus *Sphingobacterium* that has an ability to form the dipeptide from the carboxy component and the amine component.

[16] The method for producing a dipeptide according to [15] above, wherein the cell is separated from the culture.

[17] The method for producing a dipeptide according to [15] above, wherein the cell is a treated microbial cell product of the microbe.

[18] A DNA selected from the group consisting of (a), (c), (e), (g), (i), (k), (m), (o), (q), (s), (u), and (w), wherein the DNA has a base sequence defined as follows:
(a) a base sequence consisting of base numbers 127 to 1908 of SEQ ID NO:5,
(c) a base sequence consisting of base numbers 121 to 1917 of SEQ ID NO:11,
(e) a base sequence consisting of base numbers 127 to 1935 of SEQ ID NO:17,
(g) a base sequence consisting of base numbers 127 to 1995 of SEQ ID NO:22,
(i) a base sequence consisting of base numbers 104 to 1888 of SEQ ID NO:24,
(k) a base sequence consisting of base numbers 112 to 1992 of SEQ ID NO:26,
(m) a base sequence consisting of base numbers 61 to 1908 of SEQ ID NO:5,
(o) a base sequence consisting of base numbers 61 to 1917 of SEQ ID NO:11,
(q) a base sequence consisting of base numbers 61 to 1935 of SEQ ID NO:17,
(s) a base sequence consisting of base numbers 61 to 1995 of SEQ ID NO:22,
(u) a base sequence consisting of base numbers 29 to 1888 of SEQ ID NO:24, or
(w) a base sequence consisting of base numbers 61 to 1992 of SEQ ID NO:26.

[19] A recombinant DNA including the DNA according to [18] above.

[20] A transformed cell including the recombinant DNA according to [19] above.

[21] A method for producing a peptide-forming enzyme including:
culturing the transformed cell according to [20] in a medium for a time and under conditions suitable to produce the peptide-forming enzyme, and
accumulating the peptide-forming enzyme in the medium and/or transformed cell.

[22] A method for producing a dipeptide including:
culturing the transformed cell according to [20] in a medium for a time and under conditions suitable to produce a peptide-forming enzyme in a culture, and
mixing the culture with a carboxy component and an amine component to synthesize a dipeptide by enzymatic catalysis facilitated by a peptide-forming enzyme encoded by the DNA.

[23] The method for producing a dipeptide according to [22] above, wherein the cell is a microbe belonging to the genus *Sphingobacterium* that has an ability to form the dipeptide from the carboxy component and the amine component.

[24] The method for producing a dipeptide according to [23], wherein the cell is separated from the culture.

[25] The method for producing a dipeptide according to [23], wherein the cell is a treated microbial cell product of the microbe.

[26] A DNA selected from the group consisting of (b), (d), (f), (h), (j), (l), (n), (p), (r), (t), (v), and (x), wherein the DNA has a base sequence defined as follows:
(b) a base sequence that hybridizes under stringent conditions with a DNA having a base sequence complementary to a base sequence consisting of base numbers 127 to 1908 of SEQ ID NO:5, and encodes a protein that has at least 50% of the peptide-forming activity at 50° C. and a pH of 8 of a protein encoded by unmutated base numbers 127 to 1908 of SEQ ID NO:5,
(d) a base sequence that hybridizes under stringent conditions with a DNA having a base sequence complementary to a base sequence consisting of base numbers 121 to 1917 of SEQ ID NO:11, and encodes a protein that has at least 50% of the peptide-forming activity at 50° C. and a pH of 8 of a protein encoded by unmutated base numbers 121 to 1917 of SEQ ID NO:11,
(f) a base sequence that hybridizes under stringent conditions with a DNA having a base sequence complementary to a base sequence consisting of base numbers 127 to 1935 of SEQ ID NO:17, and encodes a protein that has at least 50% of the peptide-forming activity at 50° C. and a pH of 8 of a protein encoded by unmutated base numbers 127 to 1935 of SEQ ID NO:17,
(h) a base sequence that hybridizes under stringent conditions with a DNA having a base sequence complementary to a base sequence consisting of base numbers 127 to 1995 of SEQ ID NO:22, and encodes a protein that has at least 50% of the peptide-forming activity at 50° C. and a pH of 8 of a protein encoded by unmutated base numbers 127 to 1995 of SEQ ID NO:22,
(j) a base sequence that hybridizes under stringent conditions with a DNA having a base sequence complementary to a base sequence consisting of base numbers 104 to 1888 of SEQ ID NO:24, and encodes a protein that has at least 50% of the peptide-forming activity at 50° C. and a pH of 8 of a protein encoded by unmutated base numbers 104 to 1888 of SEQ ID NO:24,
(l) a base sequence that hybridizes under stringent conditions with a DNA having a base sequence complementary to a base sequence consisting of base numbers 112 to 1992 of SEQ ID NO:26, and encodes a protein that has at least 50% of the peptide-forming activity at 50° C. and a pH of 8 of a protein encoded by unmutated base numbers 112 to 1992 of SEQ ID NO:26,
(n) a base sequence that hybridizes under stringent conditions with a DNA having a base sequence complementary to a base sequence consisting of base numbers 61 to 1908 of SEQ ID NO:5, and encodes a protein that has at least 50% of the peptide-forming activity at 50° C. and a pH of 8 of a protein encoded by unmutated base numbers 61 to 1908 of SEQ ID NO:5, (p) a base sequence that hybridizes under stringent conditions with a DNA having a base sequence complementary to a base sequence consisting of base numbers 61 to 1917 of SEQ ID NO:11, and encodes a protein that has at least 50% of the peptide-forming activity at 50° C. and a pH of 8 of a protein encoded by unmutated base numbers 61 to 1917 of SEQ ID NO:11, (r) a base sequence that hybridizes under stringent conditions with a DNA having a base sequence complementary to a base sequence consisting of base numbers 61 to 1935 of SEQ ID NO:17, and encodes a protein that has at least 50% of the peptide-forming activity at 50° C. and a pH of 8 of a protein encoded by unmutated base numbers 61 to 1935 of SEQ ID NO:17, (t) a base sequence that hybridizes under stringent conditions with a DNA having a base sequence complementary to a base sequence consisting of base numbers 61 to 1995 of SEQ ID NO:22, and encodes a protein that has at least 50% of the peptide-forming activity at 50° C. and a pH of 8 of a protein encoded by unmutated base numbers 61 to 1995 of SEQ ID NO:22, (v) a base sequence that hybridizes under stringent conditions with a DNA having a base sequence complementary to a base sequence consisting of base numbers 29 to 1888 of SEQ ID NO:24, and encodes a protein that has at least 50% of the peptide-forming activity at 50° C. and a pH of 8 of a protein encoded by unmutated base numbers 29 to 1888 of SEQ ID NO:24, or (x) a base sequence that hybridizes under stringent conditions with a DNA having a base sequence complementary to a base sequence consisting of base numbers 61 to 1992 of SEQ ID NO:26, and encodes a protein that has at least 50% of the peptide-forming activity at 50° C. and a pH of 8 of a protein encoded by unmutated base numbers 61 to 1992 of SEQ ID NO:26.

[27] A recombinant DNA including the DNA according to [26] above.

[28] A transformed cell including the recombinant DNA according to [26] above.

[29] A method for producing a peptide-forming enzyme including:
culturing the transformed cell according to [28] in a medium for a time and under conditions suitable to produce the peptide-forming enzyme, and
accumulating the peptide-forming enzyme in the medium and/or transformed cell.

[30] A method for producing a dipeptide including:
culturing the transformed cell according to [28] in a medium for a time and under conditions suitable to produce a peptide-forming enzyme in a culture, and
mixing the culture with a carboxy component and an amine component to synthesize a dipeptide by enzymatic catalysis facilitated by a peptide-forming enzyme encoded by the DNA.

[31] The method for producing a dipeptide according to [30] above, wherein the cell is a microbe belonging to the genus *Sphingobacterium* that has an ability to form the dipeptide from the carboxy component and the amine component.

[32] The method for producing a dipeptide according to [31] above, wherein the cell is separated from the culture.

[33] The method for producing a dipeptide according to [31] above, wherein the cell is a treated microbial cell product of the microbe.

[34] The DNA according to [26] above, wherein stringent conditions are conditions under which washing is carried out at 60° C. at a salt concentration equivalent to 1×SSC and 0.1% SDS.

[35] A recombinant DNA including the DNA according to [34].

[36] A transformed cell including the recombinant DNA according to [35].

[37] A method for producing a peptide-forming enzyme including:
culturing the transformed cell according to [36] in a medium for a time and under conditions suitable to produce the peptide-forming enzyme, and
accumulating the peptide-forming enzyme in the medium and/or transformed cell.

[38] A method for producing a dipeptide including:
culturing the transformed cell according to [36] in a medium and under conditions suitable to produce a dipeptide-forming enzyme in a culture, and
mixing the culture with a carboxy component and an amine component to synthesize a dipeptide by enzymatic catalysis facilitated by a peptide-forming enzyme encoded by the DNA.

Furthermore, the amino acid sequence described in SEQ ID NO: 6 is specified by the DNA described in SEQ ID NO: 5 of the Sequence Listing. The amino acid sequence described in SEQ ID NO: 12 is specified by the DNA described in SEQ ID NO: 11. The amino acid sequence described in SEQ ID NO: 18 is specified by the DNA described in SEQ ID NO: 17. The amino acid sequence described in SEQ ID NO: 23 is specified by the DNA described in SEQ ID NO: 22. The amino acid sequence described in SEQ ID NO: 25 is specified by the DNA described in SEQ ID NO: 24. The amino acid sequence described in SEQ ID NO: 27 is specified by the DNA described in SEQ ID NO: 26.

BEST MODE FOR CARRYING OUT THE INVENTION

Figure 1:
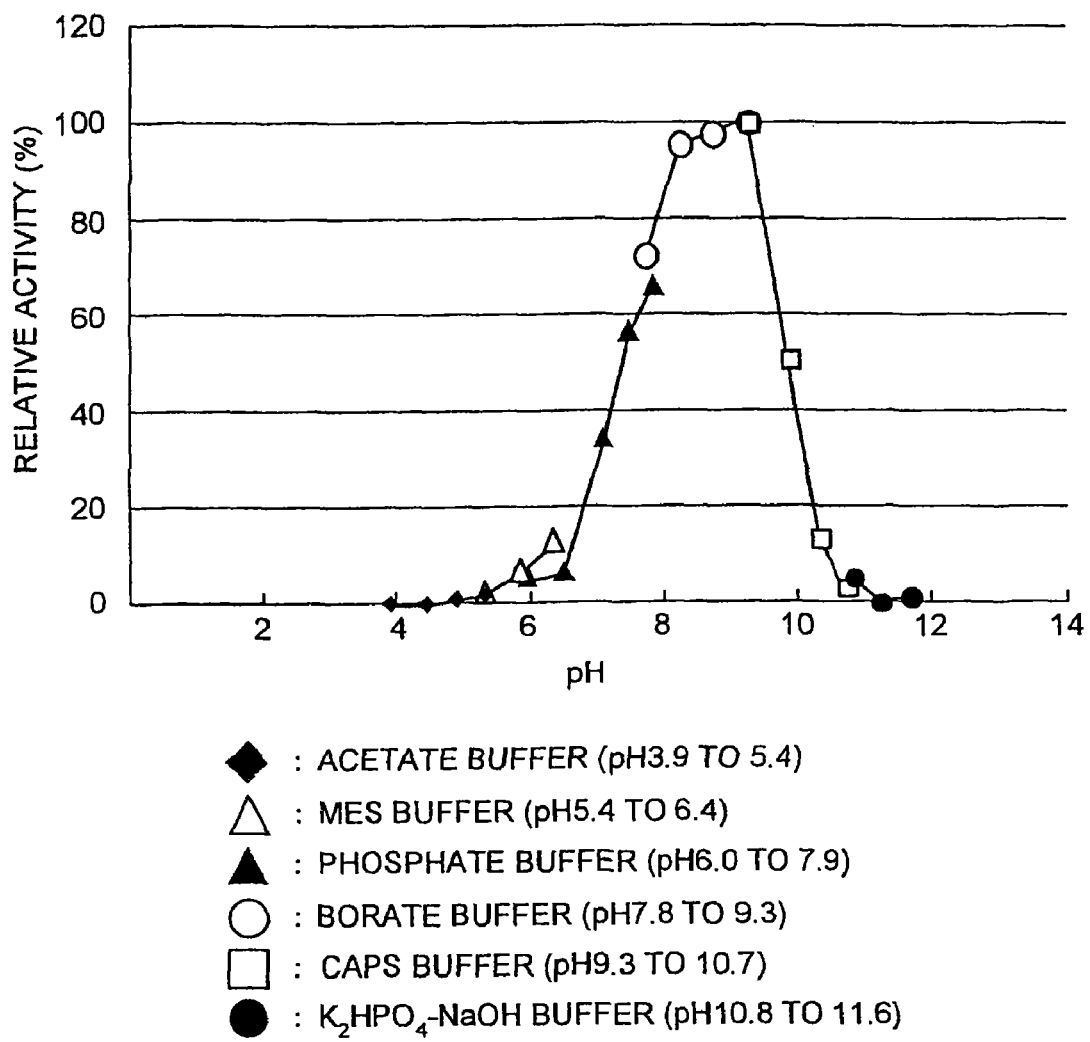
FIG. 1 is a graph illustrating the optimum pH of the enzyme of *Empedobacter* of the present invention.

Hereinafter, the novel dipeptide-forming enzyme gene of the present invention and the dipeptide-forming enzyme that is the product of that gene.

(1) Microbes Harboring the DNA of the Present Invention

The DNA of the present invention encodes a protein having the ability to form a peptide from a carboxy component and an amine component. In the present specification, a carboxy component refers to a component that provides a carbonyl site (CO) in a peptide bond (—CONH—), while an amine component refers to a component that provides an amino site (NH) in a peptide bond. In addition, in the present specification, unless otherwise indicated specifically, the term "peptide" when used alone refers to a polymer having at least one peptide bond. In addition, in the present specification, "dipeptide" refers to a peptide having one peptide bond.

Examples of microbes harboring the DNA of the present invention include bacteria belonging to the genus *Empedobacter*, genus *Sphingobacterium*, genus *Pedobacter*, genus *Taxeobacter*, genus *Cyclobacterium* or genus *Psycloserpens*, while more specific examples thereof include *Empedobacter brevis* strain ATCC 14234 (strain FERM P-18545, strain FERM BP-8113), *Sphingobacterium* sp. strain FERM BP-8124, *Pedobacter heparinus* strain IFO 12017, *Taxeobacter gelupurpurascens* strain DSMZ 11116, *Cyclobacterium marinum* strain ATCC 25205 and *Psycloserpens burtonensis* strain ATCC 700359. *Empedobacter brevis* strain ATCC 14234 (strain FERM P-18545, strain FERM BP-8113), *Sphingobacterium* sp. strain FERM BP-8124, *Pedobacter heparinus* strain IFO 12017, *Taxeobacter gelupurpurascens* strain DSMZ 11116, *Cyclobacterium marinum* strain ATCC 25205 and *Psycloserpens burtonensis* strain ATCC 700359 are microbes that were selected as a result of searching by the inventors of the present invention for microbes that produce an enzyme which forms a peptide from a carboxy component and an amine component at high yield.

Among the aforementioned strains of microbes, those microbes described with FERM numbers have been deposited at the independent administrative corporation, National Institute of Advanced Industrial Science and Technology, International Patent Organism Depository (Chuo Dai-6, 1-1 Higashi 1-Chome, Tsukuba-shi, Ibaraki-ken, Japan), and can be furnished by referring to each number.

Among the aforementioned strains of microbes, those microbes described with ATCC numbers have been deposited at the American Type Culture Collection (P.O. Box 1549, Manassas, Va. 20110, the United States of America), and can be furnished by referring to each number.

Among the aforementioned strains of microbes, those microbes described with IFO numbers have been deposited at the Institute of Fermentation, Osaka (2-17-85 Jusanbon-cho, Yodogawa-ku, Osaka-shi, Japan), and can be furnished by referring to each number.

Among the aforementioned strains of microbes, those microbes described with NBRC numbers have been deposited at the NITE Biological Resource Center of the National Institute of Technology and Evaluation (5-8 Kazusa-Kamaashi 2-Chome, Kisarazu-shi, Chiba-ken, Japan), and can be furnished by referring to each number.

Among the aforementioned strains of microbes, those microbes described with DSMZ numbers have been deposited at the Deutche Sammlung von Mikroorganismen and Zellkulturen GmbH (German Collection of Microbes and Cell Cultures) (Mascheroder Weg 1b, 38124 Braunschweig, Germany), and can be furnished by referring to each number.

*Empedobacter brevis* strain ATCC 14234 (strain FERM P-18545, strain FERM BP-8113) was deposited at the International Patent Organism Depository of the independent administrative corporation, National Institute of Advanced Industrial Science and Technology (Chuo Dai-6, 1-1 Higashi 1-Chome, Tsukuba-shi, Ibaraki-ken, Japan) on Oct. 1, 2001 and assigned the deposit number of FERM P-18545. Control of this organism was subsequently transferred to deposition under the provisions of the Budapest Treaty at the International Patent Organism Depository of the independent administrative corporation, National Institute of Advanced Industrial Science and Technology on Jul. 8, 2002 and was assigned the deposit number of FERM BP-8113 (indication of microbe: *Empedobacter brevis* strain AJ 13933).

*Sphingobacterium* sp. strain AJ 110003 was deposited at the International Patent Organism Depository of the independent administrative corporation, National Institute of Advanced Industrial Science and Technology on Jul. 22, 2002, and was assigned the deposit number of FERM BP-8124. Note that the strain AJ 110003 (FERM BP-8124) was identified to be the aforementioned *Sphingobacterium* sp. by the identification experiment described below. The strain FERM BP-8124 is a Gram-negative rod (0.7 to 0.8×1.5 to 2.0 µm) that forms spores and is not motile. Its colonies are round with a completely smooth border, contain low protrusions and have a glossy, light yellow color. The organism grows at 30° C. and is catalase positive, oxidase positive and negative for the OF test (glucose), and was identified as a bacterium belonging to the genus *Sphingobacterium* based on these properties. Moreover, because of the properties that it is negative for nitrate reduction, negative for indole production, negative for acid production from glucose, arginine dihydrolase negative, urease positive, esculin hydrolysis positive, gelatin hydrolysis negative, β-galactosidase positive, glucose assimilation positive, L-arabinose assimilation negative, D-mannose assimilation positive, D-mannitol assimilation negative, N-acetyl-D-glucosamine assimilation positive, maltose assimilation positive, potassium gluconate assimilation negative, n-capric acid assimilation negative, adipic acid assimilation negative, dl-malic acid assimilation negative, sodium citrate assimilation negative, phenyl acetate assimilation negative and cytochrome oxidase positive, it was determined to have properties that are similar to those of *Sphingobacterium multivorum* or *Sphingobacterium spiritivorum*. Moreover, although results of analyses on the homology of the base sequence of the 16S rRNA gene indicate the highest degree of homology with *Sphingobacterium multivorum* (98.8%), there was no strain with which the bacterial strain matched completely. Accordingly, this bacterial strain was therefore identified as *Sphingobacterium* sp.

(2) Microbe Culturing

In order to obtain microbial cells of microbes having the DNA of the present invention, the microbes can be cultured and grown in a suitable medium. There is no particular restriction on the medium used for this purpose so far as it allows the microbes to grow. This medium may be an ordinary medium containing ordinary carbon sources, nitrogen sources, phosphorus sources, sulfur sources, inorganic ions, and organic nutrient sources as necessary.

For example, any carbon source may be used so far as the microbes can utilize it. Specific examples of the carbon source that can be used include sugars such as glucose, fructose, maltose and amylose, alcohols such as sorbitol, ethanol and glycerol, organic acids such as fumaric acid, citric acid, acetic acid and propionic acid and their salts, hydrocarbons such as paraffin as well as mixtures thereof.

Examples of nitrogen sources that can be used include ammonium salts of inorganic acids such as ammonium sulfate and ammonium chloride, ammonium salts of organic acids such as ammonium fumarate and ammonium citrate, nitrates such as sodium nitrate and potassium nitrate, organic nitrogen compounds such as peptones, yeast extract, meat extract and corn steep liquor as well as mixtures thereof.

In addition, nutrient sources used in ordinary media, such as inorganic salts, trace metal salts and vitamins, can also be suitably mixed and used.

There is no particular restriction on culturing conditions, and culturing can be carried out, for example, for about 12 to about 48 hours while properly controlling the pH and temperature within a pH range of 5 to 8 and a temperature range of 15 to 40° C., respectively, under aerobic conditions.

(3) Purification of Enzyme

The DNA of the present invention encodes a peptide-forming enzyme. This peptide-forming enzyme can be purified from bacteria belonging to, for example, the genus *Empedobacter*. A method for isolating and purifying a peptide-forming enzyme from *Empedobacter brevis* is explained as an example of purification of the enzyme.

First, a microbial cell extract is prepared from the microbial cells of *Empedobacter brevis*, for example, the strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) by disrupting the cells using a physical method such as ultrasonic disruption or an enzymatic method using a cell wall-dissolving enzyme and removing the insoluble fraction by centrifugation and so forth. The peptide-forming enzyme can then be purified by fractionating the microbial cell extract solution obtained in the above manner by combining ordinary protein purification methods such as anion exchange chromatography, cation exchange chromatography or gel filtration chromatography.

An example of a carrier for use in anion exchange chromatography is Q-Sepharose HP (manufactured by Amersham). The enzyme is recovered in the non-adsorbed fraction under conditions of pH 8.5 when the cell extract containing the enzyme is allowed to pass through a column packed with the carrier.

An example of a carrier for use in cation exchange chromatography is MonoS HR (manufactured by Amersham). After adsorbing the enzyme onto the column by allowing the cell extract containing the enzyme to pass through a column packed with the carrier and then washing the column, the enzyme is eluted with a buffer solution having a high salt concentration. At that time, the salt concentration may be sequentially increased or a concentration gradient may be applied. For example, in the case of using MonoS HR, the enzyme adsorbed onto the column is eluted with NaCl of about 0.2 to about 0.5 M.

The enzyme purified in the manner described above can then be further uniformly purified by gel filtration chromatography and so forth. An example of the carrier for use in gel filtration chromatography is Sephadex 200pg (manufactured by Amersham).

In the aforementioned purification procedure, the fraction containing the enzyme can be verified by assaying the peptide-forming activity of each fraction according to the method indicated in the examples to be described later. The internal amino acid sequence of the enzyme purified in the manner described above is shown in SEQ ID NO: 1 and SEQ ID NO: 2 of the Sequence Listing.

(4) DNA of the Present Invention and Transformants (4-1) DNA of the Present Invention A DNA of the present invention having the base sequence consisting of base numbers 61 to 1908 described in SEQ ID NO: 5 was isolated from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002). The DNA consisting of bases numbers 61-1908 described in SEQ ID NO: 5 is a code sequence (hereinafter, "CDS") portion. The base sequence consisting of bases numbers 61 to 1908 contains a signal sequence region and a mature protein region. The signal sequence region consists of bases numbers 61 to 126, while the mature protein region consists of bases numbers 127 to 1908. Namely, the present invention provides both a peptide enzyme protein gene that contains a signal sequence, and a peptide enzyme protein gene in the form of a mature protein. The signal sequence contained in the sequence described in SEQ ID NO: 5 is a type of leader sequence, and the main function of the leader peptide encoded by this leader sequence is presumed to be excretion from inside the cell membrane to outside the cell membrane. The protein encoded by bases numbers 127 to 1908, namely the site excluding the leader peptide, is a mature protein, and is presumed to exhibit a high degree of peptide-forming activity.

The DNA having a base sequence consisting of bases numbers 61 to 1917 described in SEQ ID NO: 11, which is also a DNA of the present invention, was isolated from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). The DNA having a base sequence consisting of bases numbers 61 to 1917 is a code sequence (CDS) portion. The base sequence consisting of bases numbers 61 to 1917 contains a signal sequence region and a mature protein region. The signal sequence region is a region that consists of bases numbers 61 to 120, while the mature protein region is a region that consists of bases numbers 121 to 1917. Namely, the present invention provides both a gene for a peptide enzyme protein gene that contains a signal sequence, and a gene for a peptide enzyme protein gene in the form of a mature protein. The signal sequence contained in the sequence described in SEQ ID NO: 11 is a kind of leader sequence. The main function of a leader peptide encoded by the leader sequence is presumed to be excretion from inside the cell membrane to outside the cell membrane. The protein encoded by bases numbers 121 to 1917, namely the portion excluding the leader peptide, is a mature protein, and it is presumed to exhibit a high degree of peptide-forming activity.

A DNA of the present invention having the base sequence consisting of bases numbers 61 to 1935 described in SEQ ID NO: 17 was isolated from *Pedobacter heparinus* strain IFO 12017 (Depositary institution: Institute of Fermentation, Osaka, Address of depositary institution: 2-17-85 Jusanbon-cho, Yodogawa-ku, Osaka-shi, Japan). The DNA consisting of bases numbers 61 to 1935 described in SEQ ID NO: 17 is a CDS portion. A signal sequence region and a mature protein region are contained in the base sequence consisting of bases numbers 61 to 1935. The signal sequence region consists of bases numbers 61 to 126, while the mature protein region consists of bases numbers 127 to 1935. Namely, the present invention provides both a peptide enzyme protein gene that contains a signal sequence, and a peptide enzyme protein gene in the form of a mature protein. The signal sequence contained in the sequence described in SEQ ID NO: 17 is a type of leader sequence, and the main function of the leader peptide encoded by this leader sequence region is presumed to be excretion from inside the cell membrane to outside the cell membrane. The protein encoded by bases numbers 127 to 1935, namely the site excluding the leader peptide, is a mature protein, and is presumed to exhibit a high degree of peptide-forming activity.

A DNA of the present invention having a base sequence consisting of bases numbers 61 to 1995 described in SEQ ID NO: 22 was isolated from *Taxeobacter gelupurpurascens* strain DSMZ 11116 (Depositary institution: Deutsche Sammlung von Mikroorganismen and Zellkulturen GmbH (German Collection of Microbes and Cell Cultures), Address of depositary institution: Mascheroder Weg 1b, 38124 Braunschweig, Germany). The DNA consisting of bases numbers 61 to 1995 described in SEQ ID NO: 22 is a CDS portion. A signal sequence region and a mature protein region are contained in the base sequence consisting of bases numbers 61 to 1995. The signal sequence region consists of bases numbers 61 to 126, while the mature protein region consists of bases numbers. 127 to 1995. Namely, the present invention provides both a peptide enzyme protein gene that contains a signal sequence, and a peptide enzyme protein gene in the form of a mature protein. The signal sequence contained in the sequence described in SEQ ID NO: 22 is a type of leader sequence, and the main function of the leader peptide encoded by this leader sequence region is presumed to be excretion from inside the cell membrane to outside the cell membrane. The protein encoded by bases numbers 127 to 1995, namely the site excluding the leader peptide, is a mature protein, and is presumed to exhibit a high degree of peptide-forming activity.

A DNA of the present invention having a base sequence consisting of bases numbers 29 to 1888 described in SEQ ID NO: 24 was isolated from *Cyclobacterium marinum* strain ATCC 25205 (Depositary institution: American Type Culture Collection, Address of depositary institution: P.O. Box 1549, Manassas, Va. 20110, the United States of America). The DNA consisting of bases numbers 29 to 1888 described in SEQ ID NO: 24 is a CDS portion. A signal sequence region and a mature protein region are contained in the base sequence consisting of bases numbers 29 to 1888. The signal sequence region consists of bases numbers 29 to 103, while the mature protein region consists of bases numbers 104 to 1888. Namely, the present invention provides both a peptide enzyme protein gene that contains a signal sequence, and a peptide enzyme protein gene in the form of a mature protein. The signal sequence contained in the sequence described in SEQ ID NO: 24 is a type of leader sequence, and the main function of the leader peptide encoded by this leader sequence region is presumed to be excretion from inside the cell membrane to outside the cell membrane. The protein encoded by bases numbers 104 to 1888, namely the site excluding the leader peptide, is a mature protein, and is presumed to exhibit a high degree of peptide-forming activity.

A DNA of the present invention having a base sequence consisting of bases numbers 61 to 1992 described in SEQ ID NO: 26 was isolated from *Psycloserpens burtonensis* strain ATCC 700359 (Depositary institution: American Type Culture Collection, Address of depositary institution: P.O. Box 1549, Manassas, Va. 20110, the United States of America). The DNA consisting of bases numbers 61 to 1992 described in SEQ ID NO: 26 is a CDS portion. A signal sequence region and a mature protein region are contained in the base sequence consisting of bases numbers 61 to 1992. The signal sequence region consists of bases numbers 61 to 111, while the mature protein region consists of bases numbers 112 to 1992. Namely, the present invention provides both a peptide enzyme protein gene that contains a signal sequence, and a peptide enzyme protein gene in the form of a mature protein. The signal sequence contained in the sequence described in SEQ ID NO: 26 is a type of leader sequence, and the main function of the leader peptide encoded by this leader sequence region is presumed to be excretion from inside the cell membrane to outside the cell membrane. The protein encoded by bases numbers 112 to 1992, namely the site excluding the leader peptide, is a mature protein, and is presumed to exhibit a high degree of peptide-forming activity.

Furthermore, the various gene recombination techniques described below can be carried out in compliance with the descriptions in publications such as Molecular Cloning, 2nd edition, Cold Spring Harbor Press (1989).

The DNA of the present invention can be obtained by polymerase chain reaction (hereinafter, "PCR") (refer to PCR; White T. J. et al., Trends Genet., 5, 185 (1989)) or hybridization from a chromosomal DNA or a DNA library of *Empedobacter brevis*, *Sphingobacterium* sp., *Pedobacter heparinus*, *Taxeobacter gelupurpurascens*, *Cyclobacterium marinum* or *Psycloserpens burtonensis*. Primers for PCR can be designed based on the internal amino acid sequences determined based on peptide-forming enzyme purified as explained in the aforementioned section (3). In addition, since the base sequences of peptide-forming enzyme gene (SEQ ID NO: 5, SEQ ID NO: 11, SEQ ID NO: 22, SEQ ID NO: 24 and SEQ ID NO: 26) have been clearly determined by the present invention, primers or probes for hybridization can be designed on the basis of these base sequences, and the gene can also be isolated using a probe. If primers having sequences corresponding to the 5'-non-translated region and 3'-non-translated region are used as PCR primers, the entire length of the coding region of the present enzyme can be amplified. For example, in amplifying the region containing both the leader sequence and mature protein coding region described in SEQ ID NO: 5, specifically, an example of the 5'-side primer is a primer having the base sequence of the region upstream of base number 61 in SEQ ID NO: 5, while an example of the 3'-side primer is a primer having a sequence complementary to the base sequence of the region downstream of base number 1908.

Primers can be synthesized by the phosphoamidite method (see Tetrahedron Letters (1981), 22, 1859) using, for example, the Model 380B DNA Synthesizer manufactured by Applied Biosystems in accordance with routine methods. The PCR reaction can be carried out, for example, in accordance with the method specified by the supplier such as the manufacturer using the Gene Amp PCR System 9600 (manufactured by Perkin-Elmer) and the Takara LA PCR In Vitro Cloning Kit (manufactured by Takara Shuzo).

Regardless of whether a leader sequence is contained or not, a DNA substantially identical to a DNA consisting of the CDS described in SEQ ID NO: 5 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 5 of the Sequence Listing, or with a probe prepared from the same base sequence, and encodes a protein having peptide-forming activity, from DNAs encoding the present enzyme having a mutation or cells possessing that DNA.

Regardless of whether a leader sequence is contained or not, a DNA substantially identical to a DNA consisting of the CDS described in SEQ ID NO: 11 of the Sequence Listing is also included in the DNA of the present invention. Namely, a DNA substantially identical to the DNA of the present invention can be obtained by isolating a DNA that hybridizes, under stringent conditions, with a DNA having a base sequence complementary to the CDS described in SEQ ID NO: 11 of the Sequence Listing, or with a probe prepared from the same base sequence, and encodes a protein that has peptide-forming activity, from DNAs encoding the present enzyme having a mutation or cells possessing the DNA.

Regardless of whether a leader sequence is contained or not, a DNA substantially identical to a DNA consisting of the CDS described in SEQ ID NO: 17 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 17 of the Sequence Listing, or with a probe prepared from the same base sequence, and encodes a protein having peptide-forming activity, from DNAs encoding the present enzyme having a mutation or cells possessing that DNA.

Regardless of whether a leader sequence is contained or not, a DNA substantially identical to a DNA consisting of the CDS described in SEQ ID NO: 22 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 22 of the Sequence Listing, or with a probe prepared from the same base sequence, and encodes a protein having peptide-forming activity, from DNAs encoding the present enzyme having a mutation or cells possessing that DNA.

Regardless of whether a leader sequence is contained or not, a DNA substantially identical to a DNA consisting of the CDS described in SEQ ID NO: 24 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 24 of the Sequence Listing, or with a probe prepared from the same base sequence, and encodes a protein having peptide-forming activity, from DNAs encoding the present enzyme having a mutation or cells possessing that DNA.

Regardless of whether a leader sequence is contained or not, a DNA substantially identical to a DNA consisting of the CDS described in SEQ ID NO: 26 of the Sequence Listing is also included in the DNA of the present invention. Namely, a DNA substantially identical to the DNA of the present invention can be obtained by isolating a DNA that hybridizes under stringent conditions with a DNA having a base sequence complementary to the CDS described in SEQ ID NO: 26 of the Sequence Listing, or with a probe prepared from the same base sequence, and encodes a protein having peptide-forming activity, from DNAs encoding the present enzyme having a mutation or cells possessing that DNA.

A probe can be produced, for example, in accordance with established methods based on, for example, the base sequence described in SEQ ID NO: 5 of the Sequence Listing. In addition, a method for isolating a target DNA by using a probe to find a DNA that hybridizes with the probe may also be carried out in accordance with established methods. For example, a DNA probe can be produced by amplifying a base sequence cloned in a plasmid or phage vector, cleaving the base sequence desired to be used as a probe with a restriction enzyme and then extracting the desired base sequence. The portion to be cleaved out can be adjusted depending on the target DNA.

The term "under a stringent condition" as used herein refers to a condition under which a so-called specific hybrid is formed but no non-specific hybrid is formed. It is difficult to precisely express this condition in numerical values. For example, mention may be made of a condition under which DNAs having high homologies, for example, 50% or more, preferably 80% or more, more preferably 90% or more, hybridize with each other and DNAs having lower homologies than these do not hybridize with each other, or ordinary conditions for rinse in Southern hybridization under which hybridization is performed at 60° C. in a salt concentration corresponding to 60° C., 1×SSC and 0.1% SDS, preferably 0.1×SSC and 0.1% SDS. Although the genes that hybridize under such conditions include those genes in which stop codons have occurred at certain locations along their sequences or which have lost activity due to a mutation in the active center, these can be easily removed by ligating them to a commercially available expression vector, expressing them in a suitable host, and assaying the enzyme activity of the expression product using a method to be described later.

However, in the case of a base sequence that hybridizes under stringent conditions as described above, it is preferable that the protein encoded by that base sequence retains about a half or more, preferably 80% or more, and more preferably 90% or more, of the enzyme activity of the protein having the amino acid sequence encoded by the original base sequence serving as the base be retained under conditions of 50° C. and pH 8. For example, when explained for on the case of, for example, a base sequence that hybridizes under stringent conditions with a DNA that has a base sequence complementary to the base sequence consisting of bases numbers 127 to 1908 of the base sequence described in SEQ ID NO: 5, it is preferable that the protein encoded by that base sequence retains about a half or more, preferably 80% or more, and more preferably 90% or more, of the enzyme activity of the protein having an amino acid sequence that consists of amino acid residues numbers 23 to 616 of the amino acid sequence described in SEQ ID NO: 6 under conditions of 50° C. and pH 8.

An amino acid sequence encoded by the CDS described in SEQ ID NO: 5 of the Sequence Listing is shown in SEQ ID NO: 6 of the Sequence Listing. An amino acid sequence encoded by the CDS described in SEQ ID NO: 11 of the Sequence Listing is shown in SEQ ID NO: 12 of the Sequence Listing. An amino acid sequence encoded by the CDS described in SEQ ID NO.: 17 of the Sequence Listing is shown in SEQ ID NO: 18 of the Sequence Listing. An amino acid sequence encoded by the CDS described in SEQ ID NO: 22 of the Sequence Listing is shown in SEQ ID NO: 23 of the Sequence Listing. An amino acid sequence encoded by the CDS described in SEQ ID NO: 24 of the Sequence Listing is shown in SEQ ID NO: 25 of the Sequence Listing. An amino acid sequence encoded by the CDS described in SEQ ID NO: 26 of the Sequence Listing is shown in SEQ ID NO: 27 of the Sequence Listing.

The entire amino acid sequence described in SEQ ID NO: 6 contains a leader peptide and a mature protein region, with amino acid residues numbers 1 to 22 constituting the leader peptide, and amino acid residues numbers 23 to 616 constituting the mature protein region. In addition, the entire amino acid sequence described in SEQ ID NO: 11 includes a leader peptide and a mature protein region, with amino acid residues numbers 1 to 20 constituting the leader peptide, and amino acid residues numbers 21 to 619 constituting the mature protein region.

The entire amino acid sequence described in SEQ ID NO: 18 contains a leader peptide and a mature protein region, with amino acid residues numbers 1 to 22 constituting the leader peptide, and amino acid residues numbers 23 to 625 constituting the mature protein region.

The entire amino acid sequence described in SEQ ID NO: 23 contains a leader peptide and a mature protein region, with amino acid residues numbers 1 to 22 constituting the leader peptide, and amino acid residues numbers 23 to 645 constituting the mature protein region.

The entire amino acid sequence described in SEQ ID NO: 25 contains a leader peptide and a mature protein region, with amino acid residues numbers 1 to 25 constituting the leader peptide, and amino acid residues numbers 26 to 620 constituting the mature protein region.

The entire amino acid sequence described in SEQ ID NO: 27 contains a leader peptide and a mature protein region, with amino acid residues numbers 1 to 17 constituting the leader peptide, and amino acid residues numbers 18 to 644 constituting the mature protein region.

The protein encoded by the DNA of the present invention is a protein in which the mature protein has peptide-forming activity, and a DNA that encodes a protein substantially identical to a protein having the amino acid sequence described in SEQ ID NO: 6, SEQ ID NO: 12, SEQ ID NO: 18, SEQ ID NO: 23, SEQ ID NO: 25, or SEQ ID NO: 27 of the Sequence Listing, regardless of whether it contains a leader peptide or not, is also included in the DNA of the present invention. (Note that, base sequences are specified from amino acid sequences in accordance with the codes of the universal codons.) Namely, the present invention provides DNAs that encode proteins indicated in (A) to (X) below:

(A) a protein having an amino acid sequence consisting of amino acid residues numbers 23 to 616 of an amino acid sequence described in SEQ ID NO: 6 of the Sequence Listing,
(B) a protein having an amino acid sequence including substitution, deletion, insertion, addition, and/or inversion of one or a plurality of amino acids in amino acid residues numbers 23 to 616 of the amino acid sequence described in SEQ ID NO: 6 of the Sequence Listing, and having peptide-forming activity,
(C) a protein having the amino acid sequence consisting of amino acid residue numbers 21 to 619 of an amino acid sequence described in SEQ ID NO: 12 of the Sequence Listing,
(D) a protein having an amino acid sequence including substitution, deletion, insertion, addition, and/or inversion of one or a plurality of amino acids in amino acid residue numbers 21 to 619 of the amino acid sequence described in SEQ ID NO: 12 of the Sequence Listing, and having peptide-forming activity,
(E) a protein having an amino acid sequence consisting of amino acid residues numbers 23 to 625 of an amino acid sequence described in SEQ ID NO: 18 of the Sequence Listing,
(F) a protein having an amino acid sequence including substitution, deletion, insertion, addition, and/or inversion of one or a plurality of amino acids in amino acid residues numbers 23 to 625 of the amino acid sequence described in SEQ ID NO: 18 of the Sequence Listing, and having peptide-forming activity,
(G) a protein having an amino acid sequence consisting of amino acid residues numbers 23 to 645 of an amino acid sequence described in SEQ ID NO: 23 of the Sequence Listing,
(H) a protein having an amino acid sequence including substitution, deletion, insertion, addition, and/or inversion of one or a plurality of amino acids in amino acid residues numbers 23 to 645 of the amino acid sequence described in SEQ ID NO: 23 of the Sequence Listing, and having peptide-forming activity,
(I) a protein having an amino acid sequence consisting of amino acid residues numbers 26 to 620 of an amino acid sequence described in SEQ ID NO: 25 of the Sequence Listing,
(J) a protein having an amino acid sequence including substitution, deletion, insertion, addition, and/or inversion of one or a plurality of amino acids in amino acid residues numbers 26 to 620 of the amino acid sequence described in SEQ ID NO: 25 of the Sequence Listing, and having peptide-forming activity,
(K) a protein having an amino acid sequence consisting of amino acid residues numbers 18 to 644 of an amino acid sequence described in SEQ ID NO: 27 of the Sequence Listing,
(L) a protein having an amino acid sequence including substitution, deletion, insertion, addition, and/or inversion of one or a plurality of amino acids in amino acid residues numbers 18 to 644 of the amino acid sequence described in SEQ ID NO: 27 of the Sequence Listing, and having peptide-forming activity,
(M) a protein having an amino acid sequence described in SEQ ID NO: 6 of the Sequence Listing,
(N) a protein containing a mature protein region, having an amino acid sequence including substitution, deletion, insertion, addition, and/or inversion of one or a plurality of amino acids in the amino acid sequence described in SEQ ID NO: 6 of the Sequence Listing, and having peptide-forming activity,
(O) a protein having the amino acid sequence described in SEQ ID NO: 12 of the Sequence Listing,
(P) a protein containing a mature protein region, having an amino acid sequence including substitution, deletion, insertion, addition, and/or inversion of one or a plurality of amino acids in an amino acid sequence described in SEQ ID NO: 12 of the Sequence Listing, and having peptide-forming activity,
(Q) a protein having an amino acid sequence described in SEQ ID NO: 18 of the Sequence Listing,
(R) a protein containing a mature protein region, having an amino acid sequence including substitution, deletion, insertion, addition, and/or inversion of one or a plurality of amino acids in the amino acid sequence described in SEQ ID NO: 18 of the Sequence Listing, and having peptide-forming activity,
(S) a protein having an amino acid sequence described in SEQ ID NO: 23 of the Sequence Listing,
(T) a protein containing a mature protein region, having an amino acid sequence including substitution, deletion, insertion, addition, and/or inversion of one or a plurality of amino acids in the amino acid sequence described in SEQ ID NO: 23 of the Sequence Listing, and having peptide-forming activity,
(U) a protein having an amino acid sequence described in SEQ ID NO: 25 of the Sequence Listing,
(V) a protein containing a mature protein region, having an amino acid sequence including substitution, deletion, insertion, addition, and/or inversion of one or a plurality of amino acids in the amino acid sequence described in SEQ ID NO: 25 of the Sequence Listing, and having peptide-forming activity;
(W) a protein having an amino acid sequence described in SEQ ID NO: 27 of the Sequence Listing, and
(X) a protein containing a mature protein region, having an amino acid sequence in the amino acid sequence described in SEQ ID NO: 27 of the Sequence Listing, and having peptide-forming activity.

Here, although the meaning of the term "a plurality of" varies depending on the locations and types of the amino acid residues in the three-dimensional structure of the protein, it is within a range that does not significantly impair the three-dimensional structure and activity of the protein of the amino acid residues, and is specifically 2 to 50, preferably 2 to 30, and more preferably 2 to 10. However, in the case of amino acid sequences including substitution, deletion, insertion, addition, and/or inversion of one or a plurality of amino acids in amino acid sequences of the proteins of (B), (D), (F), (H), (J), (L), (N), (P), (R), (T), (V) or (X), it is preferable that the proteins retain about half or more, more preferably 80% or more, and even more preferably 90% or more of the enzyme activity of the proteins in the state where no mutation is included, under conditions of 50° C. and pH 8. For example, explanation will be made in the case of (B); in the case of the amino acid sequence (B) including substitution, deletion, insertion, addition, and/or inversion of one or a plurality of amino acids in the amino acid sequence described in SEQ ID NO: 6 of the Sequence Listing, it is preferable that this protein retains about half or more, more preferably 80% or more, and even more preferably 90% or more of the enzyme activity of the protein having the amino acid sequence described in SEQ ID NO: 6 of the Sequence Listing, under conditions of 50° C. and pH 8.

A mutation of an amino acid like that indicated in the aforementioned (B) and so forth is obtained by modifying the base sequence so that an amino acid of a specific site in the present enzyme gene is substituted, deleted, inserted or added by, for example, site-directed mutagenesis. In addition, a modified DNA that described above can also be obtained by mutagenesis treatment known in the art. Mutagenesis treatment refers to, for example, a method in which a DNA encoding the present enzyme is treated in vitro with hydroxylamine and so forth, as well as a method in which bacteria belonging to the genus *Escherichia* that possess a DNA encoding the present enzyme are treated by a mutagen normally used in artificial mutagenesis, such as ultraviolet irradiation, N-methyl-N'-nitro-N-nitrosoguanidine (NTG) or nitrous acid.

In addition, naturally-occurring mutations such as differences attributable to a microbe species or strain are also included in the base substitution, deletion, insertion, addition and/or inversion described above. By expressing a DNA having such a mutation in suitable cells and investigating the enzyme activity of the expression product, a DNA can be obtained that encodes a protein substantially identical to the protein described in SEQ ID NO: 6 or 12 of the Sequence Listing.

(4-2) Preparation of Transformants and Production of Peptide-Forming Enzymes

Peptide-forming enzymes can be produced by introducing a DNA of the present invention into a suitable host and expressing the DNA in that host.

Examples of hosts for expressing a protein specified by a DNA of the present invention that can be used include various prokaryotic cells such as bacteria belonging to the genus *Escherichia* such as *Escherichia coli, Empedobacter, Sphingobacterium, Flavobacterium* and *Bacillus* such as *Bacillus subtilis*, as well as various eukaryotic cells such as *Saccharomyces cerevisiae, Pichia stipitis* and *Aspergillus oryzae*.

A recombinant DNA used to introduce a DNA into a host can be prepared by inserting the DNA to be introduced into a vector corresponding to the type of host in which the DNA is to be expressed, in such a form that the protein encoded by that DNA can be expressed. In the case where a promoter unique to a peptide-forming enzyme gene of *Empedobacter brevis* and so forth functions in the host cells, the promoter can be used as a promoter for expressing the DNA of the present invention. In addition, another promoter that acts on in the host cells may be ligated to the DNA of the present invention and the DNA may be expressed under the control of the promoter as necessary.

Examples of transformation methods for introducing a recombinant DNA into host cells include the method of D. M. Morrison (see Methods in Enzymology, 68, 326 (1979)) or the method in which DNA permeability is increased by treating receptor microbial cells with calcium chloride (see Mandel, H. and Higa, A., J. Mol. Biol., 53, 159 (1970)).

In the case of mass production of a protein using recombinant DNA technology, conjugating the protein within a transformant that produces the protein to form an inclusion body of protein is also a preferable mode for carrying out the present invention. Advantages of this expression and production method include protection of the target protein from digestion by proteases present in the microbial cells, and simple and easy purification of the target protein by disrupting the microbial cells, followed by centrifugation and so forth.

The inclusion bodies of protein obtained in this manner are solubilized with a protein denaturant and the solubilized protein is converted to a properly folded, physiologically active protein by going through an activity regeneration procedure that consists primarily of lysing the protein with a protein denaturant followed by removal of the denaturant. There are numerous examples of this, including regeneration of the activity of human interleukin-2 (see Japanese Patent Application Laid-open Publication No. S61-257931).

To obtain an active protein from inclusion bodies of protein, a series of operations including solubilization and activity regeneration are required, and the procedure is more complex than in the case of producing the active protein directly. However, in the case of producing a large volume of protein that has a detrimental effect on microbial growth in microbial cells, that effect can be suppressed by accumulating the proteins in the form of inclusion bodies of inactive protein in the microbial cells.

Examples of mass production methods for producing a large volume of target protein in the form of inclusion bodies include a method in which a target protein is expressed independently under the control of a powerful promoter, and a method in which a target protein is expressed in the form of a fused protein with a protein that is known to be expressed in a large volume.

Hereinafter, the present invention will be explained more specifically taking as an example of a method for producing transformed *Escherichia coli* and using the transformed microbe to produce a peptide-forming enzyme. Furthermore, in the case of producing a peptide-forming enzyme in a microbe such as *Escherichia coli*, a DNA may be incorporated that encodes a precursor protein containing a leader sequence or a DNA may be incorporated that consists only of a mature protein region that does not contain a leader sequence, and the DNA can be suitably selected for the protein encoding sequence depending on the production conditions, form, usage conditions and so forth of the enzyme to be produced.

Promoters normally used in the production of heterogeneous proteins in *Escherichia coli* can be used as promoters for expressing a DNA encoding a peptide-forming enzyme. Examples of such promoters include T7 promoter, lac promoter, trp promoter, trc promoter, tac promoter, lambda phage PR promoter, PL promoter and other powerful promoters. In addition, examples of vectors that can be used include pUC19, pUC18, pBR322, pHSG299, pHSG298, pHSG399, pHSG398, RSF1010, pMW119, pMW118, pMW219, and pMW218. Besides, vectors of phage DNA can also be used. Moreover, expression vectors can be used that contain promoters and are capable of expressing an inserted DNA sequence, including the promoter can be used.

In order to produce a peptide-forming enzyme in the form of an inclusion body of fused protein, a gene that encodes another protein, and preferably a hydrophilic peptide is ligated upstream or downstream of the peptide-forming enzyme gene to obtain a fused protein gene. The gene that encodes another protein in this manner may be any gene that increases the amount of the fused protein accumulated, and enhances the solubility of the fused protein after the denaturation and regeneration steps. Examples of candidates for such genes include T7 gene 10, β-galactosidase gene, dehydrofolate reductase gene, γ-interferon gene, interleukin-2 gene and prochymosin gene.

When these genes are ligated to a gene that encodes a peptide-forming enzymes, the both genes are ligated so that their reading frames of codons are consistent. The genes may be ligated at a proper restriction enzyme site or a synthetic DNA having a proper sequence may be utilized.

Further, to increase a production amount of the peptide-forming enzyme, it is preferable in some cases that a terminator, which is a transcription terminating sequence, be ligated to downstream of the fusion protein gene. The terminator includes, for example, a T7 terminator, an fd phage terminator, a T4 terminator, a tetracycline resistant gene terminator, and an *Escherichia coli* trpA gene terminator.

As the vectors for introducing a gene that encodes a peptide-forming enzyme or a fused protein between the peptide-forming enzyme and another protein in *Escherichia coli* are preferred so-called multi-copy type vectors, examples of which include a plasmid having a replication origin derived from ColE1, for example, a pUC-based plasmid, and a pBR322-based plasmid or derivatives thereof. The "derivatives" as used herein refer to those plasmids that are subjected to modification by substitution, deletion, insertion, addition and/or inversion of bases. Note that the modification as used herein includes modifications by a mutagenesis treatment with a mutagen or UV irradiation, or modifications by spontaneous mutation.

To screen transformants, it is preferable that the vectors have markers such as an ampicillin resistant gene. Such plasmids include commercially available expression vectors having potent promoters (a pUC-based vector (manufactured by Takara Shuzo, Co., Ltd.), pRROK-based vector (manufactured by Clonetech Laboratories, Inc.), pKK233-2 (manufactured by Clonetech Laboratories, Inc.) and so forth.

A recombinant DNA is obtained by ligating a DNA fragment to a vector DNA; in the DNA fragment, a promoter, a gene encoding L-amino acid amide hydrolase or a fused protein consisting of an L-amino acid amide hydrolase and another protein, and depending on the case, a terminator are ligated in that order.

When *E. coli* is transformed using the recombinant DNA and the resulting *E. coli* is cultured, a peptide-forming enzyme or a fused protein consisting of the peptide-forming enzyme and another protein is expressed and produced. Although a strain that is normally used in the expression of a heterogeneous gene can be used as a host to be transformed, *Escherichia coli* strain JM109, for example, is preferable. Methods for carrying out transformation and methods for screening out transformants are described in Molecular Cloning, 2nd Edition, Cold Spring Harbor Press (1989) and other publications.

In the case of expressing a peptide-forming enzyme in the form of a fusion protein, the peptide-forming enzyme may be cleaved out using a restriction protease that uses a sequence not present in the peptide-forming enzyme, such as blood coagulation factor Xa or kallikrein, as the recognition sequence.

A medium normally used for culturing *E. coli*, such as M9-casamino acid medium or LB medium, may be used for as the a production medium. In addition, culturing conditions and production induction conditions are suitably selected according to the marker of the vector used, promoter, type of host microbe and so forth.

The following method can be used to recover the peptide-forming enzyme or fused protein consisting of the peptide-forming enzyme and another protein. If the peptide-forming enzyme or its fused protein has been solubilized in the microbial cells, the microbial cells are recovered and then disrupted or lysed so that they can be used as a crude enzyme liquid. Moreover, the peptide-forming enzyme or its fused protein can be purified prior to use by ordinary techniques such as precipitation, filtration or column chromatography as necessary. In this case, a purification method can also be used that uses an antibody of the peptide-forming enzyme or its fused protein.

In the case where inclusion bodies of protein are formed, the inclusion bodies are solubilized with a denaturant. Although they may be solubilized together with the microbial cell protein, it is preferable in consideration of the subsequent purification procedure that the inclusion bodies are taken out and then solubilized. Conventionally known methods may be used to recover the inclusion bodies from the microbial cells. For example, the inclusion bodies can be recovered by disrupting the microbial cells followed by centrifugation. Examples of denaturants capable of solubilizing the inclusion bodies include guanidine hydrochloride (for example, 6 M, pH 5 to 8) and urea (for example, 8 M) and the like.

A protein that has activity is regenerated by removing these denaturants by dialysis or the like. A Tris-HCl buffer solution, a phosphate buffer solution or the like may be used as a dialysis solution to be used in dialysis, and its concentration may be, for example, 20 mM to 0.5 M, while its pH may be, for example, 5 to 8.

The protein concentration during the regeneration step is preferably held to about 500 μg/ml or less. The dialysis temperature is preferably 5° C. or lower to prevent the regenerated peptide-forming enzyme from undergoing self-crosslinking. Moreover, the method for removing the denaturants includes dilution or ultrafiltration in addition to dialysis, and it is expected the activity can be regenerated whichever denaturant is used.

(5) Properties of Enzyme Encoded by DNA of the Present Invention

The activity of the enzyme encoded by the DNA of the present invention can be assayed by, for example, allowing the enzyme to react in a borate buffer solution containing an amino acid ester and an amine as substrates, and then quantifying the peptide formed. In a more concrete example, the reaction is carried out at 25° C. for several minutes using a borate buffer solution (pH 9.0) containing 100 mM L-alanine methyl ester and 200 mM L-glutamine.

The activity unit of the enzyme used in the present invention is defined such that 1 unit (U) is the amount of enzyme that produces 1 micromole (1 mole) of peptide in 1 minute under the condition of reacting at 25° C. using a 100 mM borate buffer solution (pH 9.0) containing 100 mM L-alanine methyl ester and 200 mM L-glutamine.

A protein encoded by the DNA of the present invention is a peptide-forming enzyme protein. Peptide-forming activity refers to the activity that forms a peptide from a carboxy component and an amine component. Hereinafter, a preferable mode of the enzyme encoded by the DNA of the present invention will be explained on its properties.

One preferable mode of the enzyme encoded by the DNA of the present invention includes an enzyme that has the abilities described below, for which the dipeptide production rate is used as an indicator. Namely, one preferable mode of the enzyme of the present invention includes an enzyme that has the ability to form a peptide from a carboxy component and an amino component, and has a production rate of L-alanyl-L-glutamine in the dipeptide formation reaction under the conditions of (i) to (iv) below of preferably 0.03 mM/min or more, more preferably 0.3 mM/min or more, and particularly preferably 1.0 mM/min or more. The conditions of the dipeptide formation reaction are as follows:

(i) the carboxy component is L-alanine methyl ester hydrochloride (100 mM);
(ii) the amine component is L-glutamine (200 mM);
(iii) the pH is 9.0; and,
(iv) the amount of homogenously purified enzyme added is less than 0.61 mg/ml as a protein amount.

The aforementioned production rate far exceeds the conventional production rate for peptide synthesis using an enzyme, and the enzyme of the present invention has the ability to catalyze peptide synthesis at an extremely rapid rate.

The aforementioned amount of enzyme added indicates a final amount of the enzyme that is added to the reaction system, and addition of the enzyme of 0.01 mg/ml or more, and preferably 0.02 mg/ml or more, as protein amount is desirable. The term "protein amount" refers to the value indicated by a colorimetric method with Coomassie brilliant blue using a protein assay CBB solution (manufactured by Nakarai) and bovine serum albumin as a standard substance.

In a specific example of the procedure for assaying the enzyme activity, the enzyme activity can be assayed by allowing the enzyme to react in a borate buffer solution containing an amino acid ester and an amine as substrates and quantifying the resulting peptide. In a more specific example, mention may be made of a method in which the enzyme is allowed to react for several minutes at 25° C. using a 100 mM borate buffer solution (pH 9.0) containing 100 mM L-alanine methyl ester and 200 mM L-glutamine.

In addition, a preferable mode of the enzyme encoded by the DNA of the present invention includes an enzyme having the property by which both an amino acid ester and an amino acid amide can be used as a substrate for the carboxy component. The words "both an amino acid ester and an amino acid amide can be used as a substrate" mean that at least one type or more of amino acid ester and at least one type or more of amino acid amide can be used as a substrate. In addition, one preferable mode of the enzyme of the present invention includes an enzyme that has the property by which all of an amino acid, a C-protected amino acid and an amine can be used as a substrate for the amine component. The words "an amino acid, a C-protected amino acid, and an amine can be used as a substrate" mean that at least one type or more of amino acid, at least one type or more of C-protected amino acid, and at least one type or more of amine can be used as a substrate. Having a wide range of substrate specificity with respect to the carboxy component or the amino component, the enzyme of the present invention is preferable in that a wide range of raw materials can be selected, which in turn is favorable in terms of cost and production equipment in the case of industrial production.

Specific examples of the carboxy component include L-amino acid esters, D-amino acid esters, L-amino acid amides and D-amino acid amides. In addition, the amino acid esters include not only amino acid esters corresponding to naturally-occurring amino acids, but also amino acid esters corresponding to non-naturally-occurring amino acids or their derivatives. Furthermore, examples of the amino acid esters include α-amino acid esters as well as β-, γ-, and ω-amino acid esters and the like, which have different amino group bonding sites. Typical examples of amino acid esters include methyl esters, ethyl esters, n-propyl esters, iso-propyl esters, n-butyl esters, iso-butyl esters, and tert-butyl esters of amino acids.

Specific examples of the amine component include L-amino acids, C-protected L-amino acids, D-amino acids, C-protected D-amino acids and amines. In addition, examples of the amines include not only naturally-occurring amines, but also non-naturally-occurring amines or their derivatives. In addition, examples of the amino acids include not only naturally-occurring amino acids, but also non-naturally-occurring amino acids or their derivatives. These include α-amino acids as well as β-, γ- and ω-amino acids and the like, which have different amino group bonding sites.

Further, in another aspect, one preferable mode of the enzyme encoded by the DNA of the present invention includes an enzyme in which the pH range over which the peptide-forming reaction can be catalyzed is 6.5 to 10.5. The ability of the enzyme of the present invention to catalyze this reaction over such a wide pH range as stated above is preferable in that it allows flexible accommodation of industrial production that could be subject to the occurrence of various restrictions. However, in the actual production of peptides, it is preferable to use the enzyme by further adjusting to an optimum pH corresponding to the obtained enzyme so as to maximize the catalytic performance of the enzyme.

Moreover, in another aspect, one preferable mode of the enzyme encoded by the DNA of the present invention includes an enzyme for which the temperature range over which the enzyme is capable of catalyzing the peptide-forming reaction is within the range of 0 to 60° C. Since the enzyme of the present invention is able to catalyze the reaction over a wide temperature range, it is preferable in that it allows flexible accommodation of industrial production that could be subject to the occurrence of various restrictions. However, in the actual production of peptides, it is preferable to use the enzyme by further adjusting to an optimum temperature corresponding to the obtained enzyme so as to maximize the catalytic performance of the enzyme.

(6) Dipeptide Production Method

The method for producing dipeptide of the present invention includes reaction between a carboxy component and an amine component in the presence of the predetermined enzyme. The dipeptide production method of the present invention includes allowing an enzyme, or enzyme-containing substance, having the ability to form a peptide from a carboxy component and an amine component, to act on the carboxy component and the amine component to synthesize a dipeptide.

The method of allowing the enzyme or enzyme-containing substance used in the present invention to act on the carboxy component and the amine component may be mixing the enzyme or enzyme-containing substance, the carboxy component, and the amine component with each other. More specifically, a method of adding the enzyme or enzyme-containing substance to a solution containing a carboxy component and an amine component and allowing them to react may be used. Alternatively, in the case of using a microbe that produces that enzyme, a method may be used that includes culturing the microbe that forms that enzyme, producing and accumulating the enzyme in the microbe or microbial culture broth, and then adding the carboxy component and amine component to the culture broth. The produced dipeptide can then be collected by established methods and purified as necessary.

The term "enzyme-containing substance" means any substance so far as it contains the enzyme, and examples of specific forms thereof include a culture of microbes that produce the enzyme, microbial cells isolated from the culture, and a product obtained by treating the microbial cells (hereinafter, "treated microbial cell product"). A culture of microbes refers to what is obtained by culturing a microbe, and more specifically, to a mixture of microbial cells, the medium used for culturing the microbe, and substances produced by the cultured microbe, and so forth. In addition, the microbial cells may be washed and used in the form of washed microbial cells. In addition, the treated microbial cell product includes the products of disrupted, lysed or freeze-dried microbial cells, and the like, and also includes a crude enzyme recovered by treating microbial cells, and so forth, as well as a purified enzyme obtained by purification of the crude enzyme, and so forth. A partially purified enzyme obtained by various types of purification methods may be used for the purified enzyme, or immobilized enzymes may be used that have been immobilized by a covalent bonding method, an adsorption method, an entrapment method, or the like. In addition, since some microbes are partially lysed during culturing depending on the microbes used, the culture supernatant may also be used as the enzyme-containing substance in such cases.

In addition, wild strains may be used as the microbes that contain the enzyme, or gene recombinant strains that express the enzyme may also be used. The microbes are not limited to intact microbial cells, but rather acetone-treated microbial cells, freeze-dried microbial cells or other treated microbial cells may also be used. Immobilized microbial cells and an immobilized treated microbial cell product obtained by immobilizing the microbial cells or treated microbial cell product by covalent bonding, adsorption, entrapment or other methods, as well as treated immobilized microbial cells, may also be used.

Furthermore, when using cultures, cultured microbial cells, washed microbial cells or a treated microbial cell product that has been obtained by disrupted or lysing microbial cells, it is often the case that an enzyme exists therein that decomposes the formed peptides without being involved in peptide formation. In this situation, it may be rather preferable in some cases to add a metal protease inhibitor like ethylene diamine tetraacetic acid (EDTA). The addition amount is within the range of 0.1 millimolar (mM) to 300 mM, and preferably 1 mM to 100 mM.

A preferable mode of the dipeptide production method of the present invention is a method in which the transformed cells described in the previously described section (4-2) are cultured in a medium, and a peptide-forming enzyme is allowed to accumulate in the medium and/or transformed cells. Since the peptide-forming enzyme can be easily produced in large volumes by using a transformant, dipeptides can be produced in large amounts and rapidly.

The amount of enzyme or enzyme-containing substance used may be enough if it is an amount at which the target effect is demonstrated (effective amount), and this effective amount can be easily determined through simple, preliminary experimentation by a person with ordinary skill in the art. In the case of using the enzyme, for example, the amount used is about 0.01 U to about 100 U, while in the case of using washed microbial cells, the amount used is about 1 g/L to about 500 g/L.

Any carboxy component may be used as far as it can form a peptide by condensation with the other substrate in the form of the amine component. Examples of carboxy component include L-amino acid esters, D-amino acid esters, L-amino acid amides and D-amino acid amides as well as organic acid esters not having an amino group. In addition, examples of amino acid esters include not only amino acid esters corresponding to naturally-occurring amino acids, but also amino acid esters corresponding to non-naturally-occurring amino acids or their derivatives. In addition, examples of amino acid esters include α-amino acid esters as well as β-, γ- and ω-amino acid esters and the like having different amino group bonding sites. Typical examples of amino acid esters include methyl esters, ethyl esters, n-propyl esters, iso-propyl esters, n-butyl esters, iso-butyl esters and tert-butyl esters of amino acids.

Any amine component may be used as far as it can form a peptide by condensation with the other substrate in the form of the carboxy component. Examples of the amine component include L-amino acids, C-protected L-amino acids, D-amino acids, C-protected D-amino acids and amines. In addition, examples of the amines include not only naturally-occurring amines, but also non-naturally-occurring amines or their derivatives. In addition, examples of the amino acids include not only naturally-occurring amino acids, but also non-naturally-occurring amino acids or their derivatives. These include α-amino acids as well as β-, γ- or ω-amino acids and the like having different amino group bonding sites.

The concentrations of the carboxy component and amine component serving as starting materials are 1 mM to 10 M, and preferably 0.05 M to 2 M, respectively; however, there are cases where it is preferable to add amine component in an amount equimolar or excess molar with respect to the carboxy component. In addition, in cases where high concentrations of substrates inhibit the reaction, these can be added stepwise during the reaction after they are adjusted to concentrations that do not cause inhibition.

The reaction temperature that allows synthesis of peptide is 0 to 60° C., and preferably 5 to 40° C. In addition, the reaction pH that allows synthesis of peptide is 6.5 to 10.5, and preferably 7.0 to 10.0.

EXAMPLES

Hereinafter, the present invention will be explained by examples. However, the present invention is not limited to these examples. In addition to confirmation by ninhydrin coloring of thin-film chromatograms (qualitative), quantitative determinations were made by the following high-performance liquid chromatography in order to assay products. Column: InertsiL ODS-2 (manufactured by GL Science, Inc.), eluate: an aqueous phosphate solution containing 5.0 mM sodium 1-octanesulfonate (pH 2.1):methanol=100:15 to 50, flow rate: 1.0 mL/min, detection: 210 nanometers (hereinafter, "nm").

Example 1

Microbe Culturing (*Empedobacter brevis* Strain FERM BP-8113)

A 50 mL medium (pH 6.2) containing 5 grams (g) of glucose, 5 g of ammonium sulfate, 1 g of monopotassium phosphate, 3 g of dipotassium phosphate, 0.5 g of magnesium sulfate, 10 g of yeast extract and 10 g of peptone in 1 liter (L) was transferred to a 500 mL Sakaguchi flask and sterilized at 115° C. for 15 minutes. This medium was then inoculated with one loopful cells of *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) that had been cultured at 30° C. for 16 hours in the same medium, followed by shake culturing at 30° C. for 16 hours and 120 strokes/min.

Example 2

Production of Peptide Using Microbial Cells

Microbial cells were collected by centrifuging (10,000 rounds per minute (rpm), 15 minutes) the culture broth obtained in Example 1, followed by suspending them to a concentration of 100 g/L in 100 mM borate buffer (pH 9.0) containing 10 mM EDTA. After respectively adding 1 mL of the suspension to 1 mL each of 100 mM borate buffer solutions (pH 9.0) containing 10 mM EDTA, 200 mM of the following carboxy components, and 400 mM of the following amino acids to make a final volume of 2 mL, the reaction was carried out at 18° C. for 2 hours. The peptides that were formed as a result of this reaction are shown in Table 1.

TABLE 1

| Carboxy component | Amine component | Formed peptide | (mM) |
|---|---|---|---|
| L-Ala-OMe | L-Leu | L-Ala-L-Leu | 38.2 |
| | L-Met | L-Ala-L-Met | 68.3 |
| | L-Phe | L-Ala-L-Phe | 62.4 |
| | L-Ser | L-Ala-L-Ser | 51.3 |
| | L-His | L-Ala-L-His | 52.1 |
| | L-Arg | L-Ala-L-Arg | 72.1 |
| | L-Gln | L-Ala-L-Gln | 68.0 |
| Gly-OMe | L-His | L-Gly-L-His | 22.1 |
| L-Ser-OMe | L-Ser | L-Ser-L-Ser | 29.0 |
| L-Val-OMe | L-Met | L-Val-L-Met | 10.5 |
| L-Met-OMe | L-Phe | L-Met-L-Phe | 28.5 |
| L-Thr-OMe | L-Leu | L-Thr-L-Leu | 23.0 |
| L-Ile-OMe | L-Met | L-Ile-L-Met | 8.3 |

Hydrochloride salts were used for all the carboxy components.

Example 3

Purification of Enzyme

The procedure after centrifugation was carried out either on ice or at 4° C. *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was cultured in the same manner in as Example 1, and the microbial cells were collected by centrifugation (10,000 rpm, 15 minutes). After washing 16 g of microbial cells with 50 mM Tris-HCl buffer (pH 8.0), they were suspended in 40 milliliters (ml or mL) of the same buffer and subjected to ultrasonic disrupting treatment for 45 minutes at 195 watts. This ultrasonically disrupted liquid was then centrifuged (10,000 rpm, 30 minutes) to remove the cell debris and obtain an ultrasonically disrupted liquid supernatant. This ultrasonically disrupted liquid supernatant was dialyzed overnight against 50 mM Tris-HCl buffer (pH 8.0) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 8.0), and the active fraction was collected from the non-adsorbed fraction. This active fraction was dialyzed overnight against 50 mM acetate buffer (pH 4.5) followed by removal of the insoluble fraction by centrifugation (10,000 rpm, 30 minutes) to obtain a dialyzed fraction in the form of the supernatant liquid. This dialyzed fraction was then applied to a Mono S column (manufactured by Amersham) pre-equilibrated with 50 mM acetate buffer (pH 4.5) to elute enzyme at a linear concentration gradient of the same buffer containing 0 to 1 M NaCl. The fraction that had the lowest level of contaminating protein among the active fractions was applied to a Superdex 200pg column (manufactured by Amersham) pre-equilibrated with 50 mM acetate buffer (pH 4.5) containing 1 M NaCl, and gel filtration was performed by allowing the same buffer (pH 4.5) containing 1 M NaCl to flow through the column to obtain an active fraction solution. As a result of performing these operations, the peptide-forming enzyme used in the present invention was confirmed to have been uniformly purified based on the experimental results of electrophoresis. The enzyme recovery rate in the aforementioned purification process was 12.2% and the degree of purification was 707 folds.

Example 4

Measurement of Molecular Weight of Enzyme

SDS-Gel Electrophoresis

A 0.3 microgram (4) equivalent of the purified enzyme fraction obtained by the method of Example 3 was applied to polyacrylamide electrophoresis. 0.3% (w/v) Tris, 1.44% (w/v) glycine and 0.1% (w/v) sodium laurylsulfate were used for the electrophoresis buffer solution, a gel having a concentration gradient of a gel concentration of 10 to 20% (Multigel 10 to 20, manufactured by Daiichi Pure Chemicals) was used for the polyacrylamide gel, and Pharmacia molecular weight markers were used as the molecular weight markers. Following completion of electrophoresis, the gel was stained with Coomassie brilliant blue R-250, and a uniform band was detected at the location of a molecular weight of about 75 kilodaltons (kDa).

Gel Filtration

The purified enzyme fraction obtained by the method of Example 3 was applied to a Superdex 200pg column (manufactured by Amersham) pre-equilibrated with 50 mM acetate buffer (pH 4.5) containing 1 M NaCl, and gel filtration was carried out by allowing the same buffer (pH 4.5) containing 1 M NaCl to flow through the column to measure the molecular weight. Pharmacia molecular weight markers were used as standard proteins having known molecular weights to prepare a calibration curve. As a result, the molecular weight of the enzyme was about 150 kDa.

Based on the results of SDS-gel electrophoresis and gel filtration, the enzyme was suggested to be a homodimer having a molecular weight of about 75 kDa.

Example 5

Optimum pH for Enzyme Reaction

The effects of pH were examined in the reaction in which L-alanyl-L-glutamine is formed from L-alanine methyl ester hydrochloride and L-glutamine. Acetate buffer (pH 3.9 to 5.4), MES buffer (pH 5.4 to 6.4), phosphate buffer (pH 6.0 to 7.9), borate buffer (pH 7.8 to 9.3), CAPS buffer (pH 9.3 to 10.7), and $K_2HPO_4$—NaOH buffer (pH 10.8 to 11.6) were used as buffers. 1 microliter (μl) of the Mono S fraction enzyme obtained in Example 3 (about 180 U/ml) was added to 100 μl of each buffer (100 mM) containing 100 mM L-alanine methyl ester, 200 mM L-glutamine and 10 mM EDTA and allowed to react at 18° C. for 5 minutes to measure the effects of pH on the reaction. The results expressed by assigning a value of 100% to the case of using borate buffer (pH 9.3) are shown in FIG. 1. As a result, the optimum pH was found to be 8 to 9.5.

Example 6

Optimum Temperature for Enzyme Reaction

Figure 2:
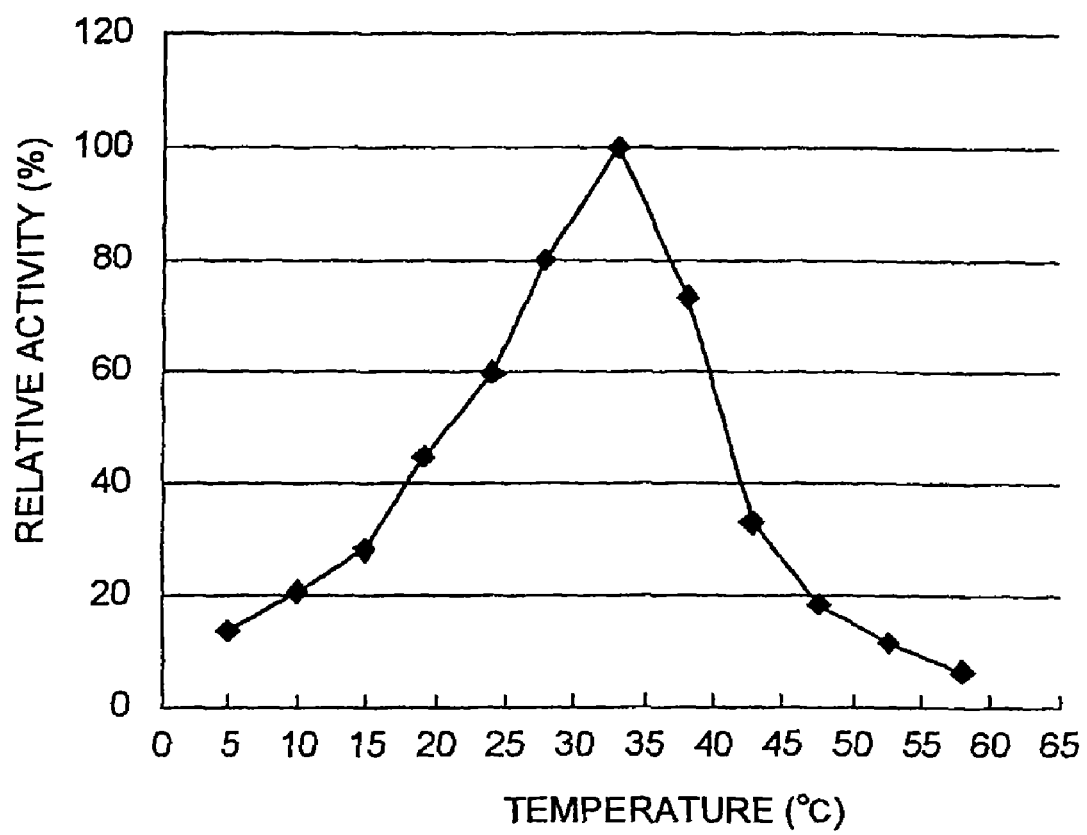
FIG. 2 is a graph illustrating the optimum temperature of the enzyme of *Empedobacter* of the present invention.

The effects of temperature were examined on the reaction in which L-alanyl-L-glutamine is formed from L-alanine methyl ester hydrochloride and L-glutamine. 1 µl of the same enzyme fraction used in Example 5 was added to 100 µl of 100 mM borate buffer (pH 9.0) containing 100 mM L-alanine methyl ester, 200 mM L-glutamine and 10 mM EDTA and allowed to react for 5 minutes at each temperature to measure the effects of temperature on the reaction. The results based on assigning a value of 100% to the activity at 34° C. are shown in FIG. 2. As a result, the optimum temperature was 30 to 40° C.

Example 7

Enzyme Inhibitors

The effects of inhibitors on the production of L-alanyl-L-glutamine were examined using L-alanine methyl ester hydrochloride and L-glutamine as substrates. 2 µl of the same enzyme fraction used in Example 5 was added to 50 µl of 100 mM borate buffer (pH 9.0) containing each of the enzyme inhibitors shown in Table 2 at 10 mM, and allowed to react at 25° C. for 5 minutes. Note that, o-phenanthroline, phenylmethylsulfonyl fluoride and p-nitrophenyl-p'-guanidinobenzoate were dissolved in methanol to a concentration of 50 mM before use. The enzyme activity under each condition was indicated as the relative activity in the case of assigning a value of 100 to the production of L-alanyl-L-glutamine in the absence of enzyme inhibitor. Those results are shown in Table 2. As a result, among the serine enzyme inhibitors tested, the enzyme was not inhibited by phenylmethylsulfonyl fluoride, but it was inhibited by p-nitrophenyl-p'-guanidinobenzoate.

TABLE 2

| | Enzyme inhibitor | Relative activity of L-Ala-L-Gln production (%) |
|---|---|---|
| | None | 100 |
| Metal enzyme inhibitor | EDTA | 96 |
| | o-Phenanthroline | 96 |
| SH enzyme inhibitor | N-Ethyl maleimide | 110 |
| | Monoiodoacetate | 101 |
| Serine enzyme inhibitor | Phenylmethylsulfonyl fluoride | 115 |
| | 4-(2-Aminoethyl)benzene sulfonyl fluoride | 75 |
| | p-Nitrophenyl-p'-guanidino benzoate | 0.1 |

Example 8

Production of L-Alanyl-L-Glutamine from L-Alanine Methyl Ester and L-Glutamine

Figure 3:
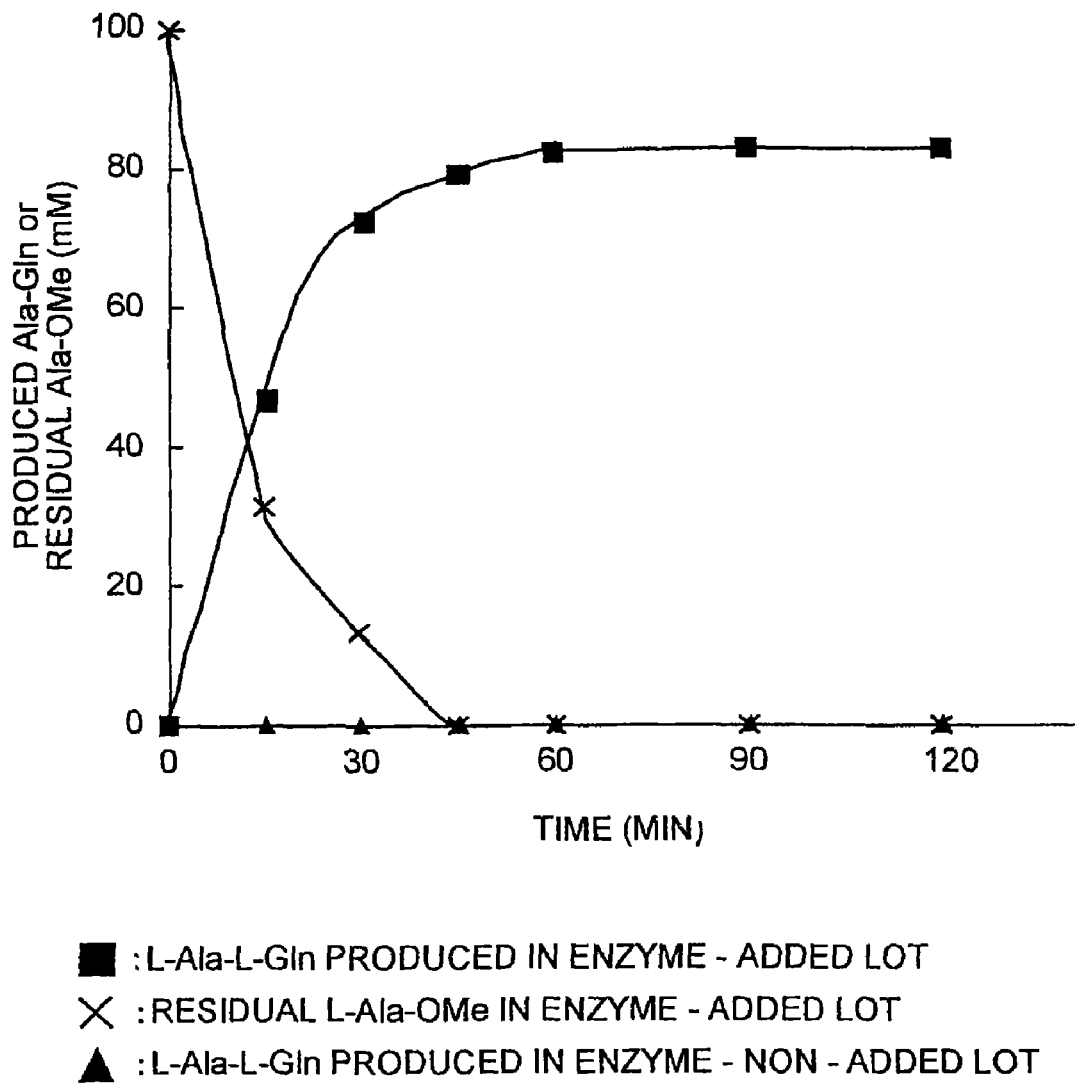
FIG. 3 is a graph illustrating the time course of L-alanyl-L-glutamine production from L-alanine methyl ester and L-glutamine.

3 µl of the same enzyme fraction as used in Example 5 was added to 100 µl of 100 mM borate buffer (pH 9.0) containing 100 mM L-alanine methyl ester hydrochloride, 200 mM L-glutamine and 10 mM EDTA, and allowed to react at 18° C. As a result, as shown in FIG. 3, 83 mM L-alanyl-L-glutamine (L-Ala-L-Gln) was formed in the case of an enzyme-added lot, and the concentration of by-product L-Ala-L-Ala-L-Gln was 1.3 mM. On the other hand, there was scarcely any production of L-Ala-L-Gln observed in an enzyme-non-added lot, and the enzyme concentration was only about 0.07 mM after reacting for 120 minutes.

Example 9

Effects of L-Glutamine Concentration on Production of L-Alanyl-L-Glutamine

1 µl of the same enzyme fraction as used in Example 5 was added to 100 µl of 100 mM borate buffer (pH 9.0) containing 100 mM L-alanine methyl ester hydrochloride, L-glutamine at the concentrations shown in Table 3 and 10 mM EDTA, and allowed to react at 18° C. for 2 hours. Those results are shown in Table 3.

TABLE 3

| L-Alanine methyl ester hydrochloride (mM) | L-Glutamine (mM) | L-Ala-L-Gln (mM) |
|---|---|---|
| 100 | 100 | 68.2 |
| | 110 | 72.1 |
| | 120 | 73.3 |
| | 130 | 75.1 |
| | 150 | 75.5 |
| | 200 | 82.0 |

Example 10

Substrate Specificity of Enzyme (1)

Ester specificity was examined in the case of using L-amino acid ester for the carboxy component. 2 µl of the same enzyme fraction as used in Example 5 was added to 100 µl of 100 mM borate buffer (pH 9.0) containing the carboxy components indicated in Table 4 at 100 mM, 200 mM L-glutamine and 10 mM EDTA, and allowed to react at 25° C. for 2 hours. The amounts of L-Ala-L-Gln formed in this reaction are shown in Table 4. HCl represents hydrochloride in Table 4.

TABLE 4

| Carboxy component | L-Ala-L-Gln formed (mM) |
|---|---|
| L-Alanine methyl ester•HCl | 84.3 |
| L-Alanine ethyl ester•HCl | 91.5 |
| L-Alanine isopropyl ester•HCl | 78.9 |
| L-Alanine-t-butyl ester•HCl | 7.5 |

Example 11

Substrate Specificity of Enzyme (2)

Peptide production was examined in the case of using L-alanine methyl ester for the carboxy component and using various L-amino acids for the amine component. 2 µl of the same enzyme fraction as used in Example 5 was added to 100 µl of 100 mM borate buffer (pH 9.0) containing 100 mM L-alanine methyl ester hydrochloride, the L-amino acids shown in Table 5 at 150 mM and 10 mM EDTA, and allowed to react at 25° C. for 3 hours. The amounts of various peptides formed in this reaction are shown in Table 5. The "+" mark indicates those peptides for which production was confirmed but which were unable to be quantified due to the absence of a standard, while "tr" indicates a trace amount.

TABLE 5

| Amine component | Formed peptide | (mM) |
|---|---|---|
| Gly | L-Ala-Gly | 13.7 |
| L-Ala | L-Ala-L-Ala | 25.4 |
| L-Val | L-Ala-L-Val | 20.8 |
| L-Leu | L-Ala-L-Leu | 45.3 |
| L-Ile | L-Ala-L-Ile | 33.9 |
| L-Met | L-Ala-L-Met | 83.3 |
| L-Phe | L-Ala-L-Phe | 74.4 |
| L-Trp | L-Ala-L-Trp | 53.9 |
| L-Ser | L-Ala-L-Ser | 62.5 |
| L-Thr | L-Ala-L-Thr | 53.9 |
| L-Asn | L-Ala-L-Asn | 65.5 |
| L-Gln | L-Ala-L-Gln | 79.3 |
| L-Tyr | L-Ala-L-Tyr | 17.6 |
| L-CySH | L-Ala-L-CySH | + |
| L-Lys | L-Ala-L-Lys | 71.8 |
| L-Arg | L-Ala-L-Arg | 88.0 |
| L-His | L-Ala-L-His | 66.9 |
| L-Asp | L-Ala-L-Asp | 2.1 |
| L-Glu | L-Ala-L-Glu | 42.9 |
| L-Pro | L-Ala-L-Pro | tr |

Example 12

Substrate Specificity of Enzyme (3)

Peptide production was examined in the case of using various types of L-amino acid methyl esters for the carboxy component and using L-glutamine for the amine component. 2 µl of the same enzyme fraction as used in Example 5 was added to 100 µl of 100 mM borate buffer (pH 9.0) containing the L-amino acid methyl ester hydrochloride salts (AA-OMe-.HCl) shown in Table 6 at 100 mM, 150 mM L-glutamine and 10 mM EDTA, and allowed to react at 25° C. for 3 hours. The amounts of various peptides formed in this reaction are shown in Table 6. The "+" mark indicates those peptides for which production was confirmed but which were unable to be quantified due to the absence of a standard, while "tr" indicates a trace amount. Furthermore, Tween-80 was added to the reaction system to a final concentration of 0.1% in the case of using L-Trp-OMe and L-Tyr-OMe.

TABLE 6

| Carboxy component | Formed peptide | (mM) | Carboxy component | Formed peptide | (mM) |
|---|---|---|---|---|---|
| Gly-OMe | Gly-L-Gln | 54.7 | L-Tyr-OMe | L-Tyr-L-Gln | 3.4 |
| L-Ala-OMe | L-Ala-L-Gln | 74.6 | CySH-OMe | L-CySH-L-Gln | + |
| L-Val-OMe | L-Val-L-Gln | 15.4 | L-Lys-OMe | L-Lys-L-Gln | + |
| L-Leu-OMe | L-Leu-L-Gln | + | L-Arg-OMe | L-Arg-L-Gln | 7.1 |
| L-Ile-OMe | L-Ile-L-Gln | 8.4 | L-His-OMe | L-His-L-Gln | + |
| L-Met-OMe | L-Met-L-Gln | 12.0 | L-Asp-α-OMe | α-L-Asp-L-Gln | tr |
| L-Phe-OMe | L-Phe-L-Gln | 0.9 | L-Asp-β-OMe | β-L-Asp-L-Gln | tr |
| L-Trp-OMe | L-Trp-L-Gln | + | L-Glu-α-OMe | α-L-Glu-L-Gln | + |
| L-Ser-OMe | L-Ser-L-Gln | 24.0 | L-Glu-γ-OMe | γ-L-Glu-L-Gln | + |
| L-Thr-OMe | L-Thr-L-Gln | 81.9 | L-Pro-OMe | L-Pro-L-Gln | 2.2 |
| L-Asn-OMe | L-Asn-L-Gln | + | | | |
| L-Gln-OMe | L-Gln-L-Gln | 0.3 | | | |

Hydrochloride salts were used for all the carboxy components.

Example 13

Substrate Specificity of Enzyme (4)

Peptide production was examined in the case of using various L-amino acid methyl esters for the carboxy component and various L-amino acids for the amine component. 2 µl of the same enzyme fraction as used in Example 5 was added to 100 µl of 100 mM borate buffer (pH 9.0) containing the L-amino acid methyl ester hydrochloride salts (AA-OMe-.HCl) shown in Table 7 at 100 mM, the L-amino acids shown in Table 7 at 150 mM and 10 mM EDTA, and allowed to react at 25° C. for 3 hours. The amounts formed of each of the peptides formed in this reaction are shown in Table 7. The "tr" indicates a trace amount. Furthermore, Tween-80 was added to the reaction system to a final concentration of 0.1% in the case of using L-Trp-OMe. The "+" mark indicates those peptides for which production was confirmed but which were unable to be quantified due to the absence of a standard.

TABLE 7

| Carboxy component | Amine component | Formed peptide | (mM) |
|---|---|---|---|
| Gly-OMe | L-CySH | Gly-L-CySH | 45.6 |
| | L-Arg | Gly-L-Arg | 25.5 |
| | L-Phe | Gly-L-Phe | 44.0 |
| | L-His | Gly-L-His | 31.6 |
| | L-Lys | Gly-L-Lys | 9.8 |
| | L-Ser | Gly-L-Ser | 44.2 |
| L-Thr-OMe | Gly | L-Thr-Gly | 9.4 |
| | L-Ala | L-Thr-L-Ala | 9.4 |
| | L-Val | L-Thr-L-Val | 0.7 |
| | L-Leu | L-Thr-L-Leu | 28.4 |
| | L-Met | L-Thr-L-Met | 38.6 |
| | L-Ser | L-Thr-L-Ser | 58.2 |
| L-Ser-OMe | L-Ser | L-Ser-L-Ser | 38.0 |
| | L-Met | L-Ser-L-Met | 12.5 |
| | L-Phe | L-Ser-L-Phe | 20.3 |
| L-Val-OMe | L-Ser | L-Val-L-Ser | 30.8 |
| | L-Met | L-Val-L-Met | 10.3 |
| | L-Phe | L-Val-L-Phe | 6.1 |
| L-Met-OMe | L-Ser | L-Met-L-Ser | 12.8 |
| | L-Met | L-Met-L-Met | 25.0 |
| | L-Phe | L-Met-L-Phe | 34.0 |
| L-Ile-OMe | L-Ser | L-Ile-L-Ser | 17.2 |
| | L-Met | L-Ile-L-Met | 10.0 |
| | L-Phe | L-Ile-L-Phe | 5.2 |
| L-Arg-OMe | L-Ser | L-Arg-L-Ser | 3.6 |
| | L-Met | L-Arg-L-Met | 0.7 |
| | L-Phe | L-Arg-L-Phe | 1.9 |
| L-Leu-OMe | L-Met | L-Leu-L-Met | 12.2 |
| L-Trp-OMe | L-Met | L-Trp-L-Met | 4.1 |
| L-Lys-OMe | L-Met | L-Lys-L-Met | 6.8 |
| L-His-OMe | L-Met | L-His-L-Met | 6.5 |
| L-Asn-OMe | L-Glu | L-Asn-L-Glu | 10.2 |

Hydrochloride salts were used for all the carboxy components.

Example 14

Substrate Specificity of Enzyme (5)

Peptide production was examined in the case of using the L or D forms of various amino acid methyl esters for the carboxy component, and the L or D forms of various amino acids for the amine component. 2 µl of the same enzyme fraction as used in Example 5 was added to 100 µl of 100 mM borate buffer (pH 9.0) containing the various amino acid methyl ester hydrochloride salts (AA-OMe.HCl) shown in Table 8 at 100 mM, the various amino acids shown in Table 8 at 150 mM and 10 mM EDTA, and allowed to react at 25° C. for 3 hours.

The amounts of various peptides formed in this reaction are shown in Table 8. The "tr" indicates a trace amount.

TABLE 8

| Carboxy component | Amine component | Formed peptide | (mM) |
|---|---|---|---|
| D-Ala-OMe | L-Gln | D-Ala-L-Gln | 69.3 |
| D-Ala-OMe |  | D-Ala-L-Ser | 20.3 |
| D-Thr-OMe |  | D-Thr-L-Ser | 1.0 |
| D-Ser-OMe | L-Ser | D-Ser-L-Ser | 3.3 |
| D-Val-OMe |  | D-Val-L-Ser | 0.6 |
| D-Met-OMe |  | D-Met-L-Ser | 5.1 |
| L-Ala-OMe | D-Gln | L-Ala-D-Gln | 0.3 |
| L-Ala-OMe |  | L-Ala-D-Ser | 5.4 |
| L-Thr-OMe |  | L-Thr-D-Ser | 6.9 |
| L-Ser-OMe | D-Ser | L-Ser-D-Ser | 16.2 |
| L-Val-OMe |  | L-Val-D-Ser | 1.4 |
| L-Met-OMe |  | L-Met-D-Ser | 1.9 |
| D-Ala-OMe | D-Gln | D-Ala-D-Gln | tr |
| D-Ala-OMe |  | D-Ala-D-Ser | 0.2 |
| D-Thr-OMe |  | D-Thr-D-Ser | 1.1 |
| D-Ser-OMe | D-Ser | D-Ser-D-Ser | 2.5 |
| D-Val-OMe |  | D-Val-D-Ser | 0.5 |
| D-Met-OMe |  | D-Met-D-Ser | 2.7 |

Hydrochloride salts were used for all the carboxy components.

Example 15

Substrate Specificity of Enzyme (6)

Peptide production was examined using various L-amino acid amides for the carboxy component, and various L-amino acids for the amine component. 2 µl of the same enzyme fraction as that used in Example 5 was added to 100 µl of 100 mM borate buffer (pH 9.0) containing the L-amino acid amide hydrochloride salts ($AA-NH_2.HCl$) shown in Table 9 at 100 mM, the L-amino acids shown in Table 9 at 150 mM and 10 mM EDTA, and allowed to react at 25° C. for 3 hours. The amounts of various peptides formed in this reaction are shown in Table 9.

TABLE 9

| Carboxy component | Amine component | Formed peptide | (mM) |
|---|---|---|---|
| L-Phe-$NH_2$ | L-Gln | L-Phe-L-Gln | 0.2 |
| L-Phe-$NH_2$ | L-Ser | L-Phe-L-Ser | 0.6 |
| L-Ala-$NH_2$ | L-Gln | L-Ala-L-Gln | 7.6 |
| L-Ala-$NH_2$ | L-Met | L-Ala-L-Met | 3.4 |
| L-Ala-$NH_2$ | L-His | L-Ala-L-His | 3.9 |
| L-Thr-$NH_2$ | L-Gln | L-Thr-L-Gln | 0.3 |

Example 16

Substrate Specificity of Enzyme (7)

Peptide production was examined in the case of using various L-alanine methyl esters for the carboxy component and C-protected L-amino acids for the amine component. 2 µl of the same enzyme fraction as used in Example 5 was added to 100 µl of 100 mM borate buffer (pH 9.0) containing the L-alanine methyl ester hydrochloride salt (Ala-OMe.HCl) shown in Table 10 at 100 mM, the L-amino acid amide hydrochloride salts shown in Table 10 at 150 mM and 10 mM EDTA, and allowed to react at 25° C. for 3 hours. The amounts of various peptides formed in this reaction are shown in Table 10.

TABLE 10

| Carboxy component | Amine component | Formed peptide | (mM) |
|---|---|---|---|
| L-Ala-OMe | Gly-$NH_2$ | L-Ala-Gly-$NH_2$ | 7.4 |
|  | L-Ala-$NH_2$ | L-Ala-L-Ala-$NH_2$ | 8.3 |
|  | L-Phe-$NH_2$ | L-Ala-L-Phe-$NH_2$ | 12.2 |

Example 17

Substrate Specificity of Enzyme (8)

Peptide production was examined in the case of using various amino acid methyl esters for the carboxy component and methylamine for the amine component. 2 µl of the same enzyme fraction as used in Example 5 was added to 100 µl of 100 mM borate buffer (pH 9.0) containing the amino acid methyl ester hydrochloride salts (AA-OMe.HCl) shown in Table 11 at 100 mM, the methylamine shown in Table 11 at 150 mM and 10 mM EDTA, and allowed to react at 25° C. for 3 hours. The amounts of various peptides formed in this reaction are shown in Table 11.

TABLE 11

| Carboxy component | Amine component | Formed peptide (mM) | |
|---|---|---|---|
| Gly-OMe | Methylamine | Gly-methylamine | 1.1 |
| L-Thr-OMe |  | L-Thr-methylamine | 0.2 |
| L-Ala-OMe |  | L-Ala-methylamine | 0.3 |

Example 18

Substrate Specificity of Enzyme (9)

Peptide production was examined in the case of using β-amino acid ester for the carboxy component or β-amino acid for the amine component. 2 µl of the same enzyme fraction as used in Example 5 was added to 100 µl of 100 mM borate buffer (pH 9.0) containing the carboxy components shown in Table 12 at 100 mM, the amine components shown in Table 12 at 150 mM and 10 mM EDTA, and allowed to react at 25° C. for 3 hours. The amounts of various peptides formed in this reaction are shown in Table 12. The "tr" indicates a trace amount.

TABLE 12

| Carboxy component | Amine component | Formed peptide (mM) | |
|---|---|---|---|
| Gly-OMe | β-Ala | Gly-β-Ala | 2.2 |
| Gly-OMe | β-Phe | Gly-β-Phe | 0.4 |
| L-Ala-OMe | β-Ala | Ala-β-Ala | 7.7 |
| L-Ala-OMe | β-Phe | Ala-β-Phe | 1.4 |
| L-Thr-OMe | β-Ala | Thr-β-Ala | 3.2 |
| L-Thr-OMe | β-Phe | Thr-β-Phe | 1.4 |
| p-Ala-OMe | L-α-Ala | β-Ala-L-α-Ala | tr |
| p-Ala-OMe | β-Ala | β-Ala-β-Ala | 0.2 |
| 13-Ala-OMe | L-Gln | β-Ala-L-Gln | 0.6 |
| p-Ala-OMe | L-Ser | β-Ala-L-Ser | 3.2 |

Hydrochloride salts were used for all of the carboxy components.

Example 19

Substrate Specificity of Enzyme (10)

Oligopeptide production was examined in the case of using L-amino acid ester for the carboxy component and peptide for the amine component. 2 μl of the same enzyme fraction as used in Example 5 was added to 100 μl of 100 mM borate buffer (pH 9.0) containing the carboxy components shown in Table 13 at 100 mM, the amine components shown in Table 13 at 150 mM and 10 mM EDTA, and allowed to react at 25° C. for 3 hours. The amounts of various peptides formed in this reaction are shown in Table 13. As a result, it was clearly demonstrated that the present enzyme can form not only dipeptide, but also long-chain peptides by using a peptide for the amine component.

As has been indicated in the aforementioned Examples 9 to 20, the present enzyme obtained from *Empedobacter brevis* strain FERM BP-18545 was determined to have extremely broad substrate specificity.

TABLE 13

| Carboxy component | Amine component | Produced peptide (mM) | |
|---|---|---|---|
| L-Ala-OMe | L-Ala | L-Ala-L-Ala | 28.7 |
| | L-Ala-L-Ala | L-Ala-L-Ala-L-Ala | 57.5 |
| | L-Ala-L-Ala-L-Ala | L-Ala-L-Ala-L-Ala-L-Ala | 44.5 |
| | L-Ala-L-Ala-L-Ala-L-Ala | L-Ala-L-Ala-L-Ala-L-Ala-L-Ala | 34.8 |
| | L-Ala-L-Ala-L-Ala-L-Ala-L-Ala-L-Ala | L-Ala-L-Ala-L-Ala-L-Ala-L-Ala-L-Ala-L-Ala | 1.4* |
| | L-Ala-L-Gln | L-Ala-L-Ala-L-Gln | 15.2 |
| | Gly-L-Ala | L-Ala-Gly-L-Ala | 25.9 |
| | Gly-Gly | L-Ala-Gly-Gly | 41.7 |
| | L-His-L-Ala | L-Ala-L-His-L-Ala | 55.9 |
| | L-Leu-L-Ala | L-Ala-L-Leu-L-Ala | 48.3 |
| | L-Phe-L-Ala | L-Ala-L-Phe-L-Ala | 49.7 |
| | L-Phe-Gly | L-Ala-L-Phe-Gly | 43.7 |
| Gly-OMe | L-Ala-L-Tyr | Gly-L-Ala-L-Tyr | 1.7 |
| | Gly-L-Gln | Gly-Gly-L-Gln | 7.2 |
| | Gly-L-Tyr-L-Ala | Gly-Gly-L-Tyr-L-Ala | 44.2 |
| L-Thr-OMe | Gly-Gly | L-Thr-Gly-Gly | 83.0 |

*Since the solubility of L-Ala-L-Ala-L-Ala-L-Ala-L-Ala-L-Ala was low, the carboxy component was used at 15 mM in this reaction system. The other conditions were the same as those explained in the example. Hydrochloride salts were used for all the carboxy components.

component was used at a concentration of 10 mM and the amine component was used at 15 mM in this reaction system. The other conditions were the same as those explained in the example. Hydrochloride salts were used for all the carboxy components.

Example 20

Comparison of Ability to Catalyze Peptide Formation with Known Enzymes

The peptide-forming ability of the present enzyme was compared with that of known enzymes. Carboxypeptidase Y described in EP 278787A1 and the thiol endopeptidases (ficin, papain, bromelain, and chymopapain) described in EP 359399B1 were used as the known enzymes, and they were used in the form of purified enzymes (manufactured by Sigma). The enzyme uniformly purified in Example 3 was used as a source of the present enzyme of the present invention. These enzymes were added to a reaction system in the protein amounts shown in Table 14. The reaction was carried out by adding the enzyme to 100 μl of borate buffer (pH 9.0) containing 100 mM L-alanine methyl ester hydrochloride and 200 mM L-glutamine and allowing the resultant to react at 25° C. Note that the carboxypeptidase used was one dissolved in 10 mM acetate buffer (pH 5.0) containing 1 mM EDTA, while the thiol endopeptidase used was one dissolved in 10 mM acetate buffer (pH 5.0) containing 2 mM EDTA, 0.1 M KCl, and 5 mM dithiothreitol. The ratios of the production rates of L-alanyl-L-glutamine by these enzymes are shown in Table 14.

As a result, the production of an extremely trace small amount of L-alanyl-L-glutamine was observed even in the absence of enzymes, while a slight increase in the production rate was observed in the section where carboxypeptidase- or thiol endopeptidase-added lot as compared with the enzyme-non-added lot. In contrast, an overwhelmingly higher rate of production of L-alanyl-L-glutamine was observed in the enzyme-added lot, and that rate of production was about 5,000 to 100,000 times higher than those of carboxypeptidase Y and of thiol endopeptidase. As has been described above, the present enzyme was verified to have an extremely high peptide production rate unlike any known enzyme in the prior art. Furthermore, the enzyme of the present invention is a dimer having a molecular weight of about 75,000. In contrast, the molecular weight of the carboxypeptidase Y has been reported to be about 61,000, while the molecular weight of thiol endopeptidase has been reported to be about 23,000 to 36,000. Thus, the L-alanyl-L-glutamine production rate of the enzyme of the present invention as compared to those of the carboxypeptidase Y and the thiol endopeptidase is even greater when the rate is expressed per molecular weight than when it is expressed per unit weight as indicated in the examples.

TABLE 14

| Enzyme | Amount of enzyme added (protein mg/ml) | L-Ala-L-Gln production rate (mM/min) | Ratio of L-Ala-L-Gln production rate per enzyme unit weight |
|---|---|---|---|
| No enzyme | 0 | 0.0006 | |
| Carboxy-peptidase Y | 0.61 | 0.0257 | 0.0191 |
| Ficin | 2.60 | 0.0096 | 0.0017 |
| Papain | 2.30 | 0.0106 | 0.0021 |
| Bromelain | 2.80 | 0.0062 | 0.0010 |
| Chymopapain | 3.60 | 0.0100 | 0.0013 |
| Enzyme of present invention | 0.02 | 4.4000 | 100.0 |

Example 21

Production of L-Alanyl-L-Glutamine Using Microbial Cell of *Sphingobacterium* sp.

A 50 ml medium (pH 7.0) containing 5 g of glucose, 5 g of ammonium sulfate, 1 g of monopotassium phosphate, 3 g of dipotassium phosphate, 0.5 g of magnesium sulfate, 10 g of yeast extract, and 10 g of peptone in 1 L was transferred to a 500 mL Sakaguchi flask and sterilized at 115° C. for 15 minutes for culturing *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). This was then inoculated with one loopful cells of *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) cultured at 30° C. for 24 hours in a slant agar medium (agar: 20 g/L, pH 7.0) containing 5 g of glucose, 10 g of yeast extract, 10 g of peptone and 5 g of NaCl in 1 L, followed by shake culturing at 30° C. for 20 hours and 120 strokes/minute. 1 ml of this culture broth was then added to the aforementioned medium (50 ml/500 mL Sakaguchi flask) and cultured at 30° C. for 18 hours. Following completion of the culturing, the microbial cells were separated from the culture broth by centrifugation and suspended in 0.1 M borate buffer (pH 9.0) containing 10 mM EDTA at a concentration of 100 g/L as wet microbial cells. 0.1 mL of 100 mM borate buffer (pH 9.0) containing 10 mM EDTA, 200 mM L-alanyl methyl ester hydrochloride and 400 mM L-glutamine was then added to 0.1 mL of this microbial cell suspension. The resulting 0.2 mL of mixture was allowed to react at 25° C. for 120 minutes. The concentration of L-alanyl-L-glutamine formed at this time was 62 mM.

Example 22

Purification of Enzyme from *Sphingobacterium* sp.

The following procedure after centrifugation was carried out either on ice or at 4° C. *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultured in the same manner as Example 21, and the microbial cells were collected by centrifugation (10,000 rpm, 15 minutes). After washing 2 g of microbial cells with 20 mM Tris-HCl buffer (pH 7.6), they were suspended in 8 ml of the same buffer and subjected to ultrasonic disrupting treatment for 45 minutes at 195 W. This ultrasonically disrupted liquid was then centrifuged (10,000 rpm, 30 minutes) to remove the cell debris and obtain an ultrasonically disrupted liquid supernatant. This ultrasonically disrupted liquid supernatant was dialyzed overnight against 20 mM Tris-HCl buffer (pH 7.6) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 7.6), and the active fraction was collected from the non-adsorbed fraction. This active fraction was dialyzed overnight against 20 mM acetate buffer (pH 5.0) followed by removal of the insoluble fraction by centrifugation (10,000 rpm, 30 minutes) to obtain a dialyzed fraction in the form of the supernatant liquid. This dialyzed fraction was then applied to an SP-Sepharose HP column (manufactured by Amersham) pre-equilibrated with 20 mM acetate buffer (pH 5.0) to obtain the active fraction in which enzyme was eluted at a linear concentration gradient of the same buffer containing 0 to 1 M NaCl.

Example 23

Production of L-Alanyl-L-Glutamine Using Enzyme Fraction

10 µl of the SP-Sepharose HP fraction (about 27 U/ml) purified in Example 22 was added to 90 µl of 111 mM borate buffer (pH 9.0) containing 111 mM L-alanine methyl ester hydrochloride, 222 mM L-glutamine and 11 mM EDTA, and allowed to react at 25° C. for 120 minutes. As a result, 73 mM of L-alanyl-L-glutamine was formed in the enzyme-added lot. On the other hand, there was scarcely any production of L-Ala-L-Glu observed in the enzyme-non-added lot, and the production amount was only about 0.07 mM after reacting for 120 minutes.

Example 24

Substrate Specificity of Enzyme (11)

Substrate specificity was examined for enzyme derived from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). 100 µl of 100 mM borate buffer (pH 9.0) containing the various carboxy components at a final concentration of 100 mM and the various amine components at a final concentration of 150 mM shown in Tables 15-1 to 15-4, the SP-Sepharose HP fraction enzyme purified in Example 22 (addition of 0.33 units in the reaction liquid) and 10 mM EDTA were allowed to react at 25° C. for 1.5 hours. The amounts of various peptides formed in this reaction are shown in Table 15. The "+" mark indicates those peptides for which production was confirmed but which were unable to be quantified due to the absence of a standard, while "tr" indicates a trace amount. Furthermore, Tween-80 was added to the reaction system to a final concentration of 0.1% in the case of using L-Tyr-OMe. In addition, hydrochloride salts were used for all carboxy components.

TABLE 15-1

| Carboxy component | Amine component | Produced peptide | (mM) |
|---|---|---|---|
| L-Ala-OMe | Gly | L-Ala-Gly | 11.1 |
| | L-Ala | L-Ala-L-Ala | 13.1 |
| | L-Val | L-Ala-L-Val | 10.9 |
| | L-Leu | L-Ala-L-Leu | 33.0 |
| | L-Ile | L-Ala-L-Ile | 24.7 |
| | L-Met | L-Ala-L-Met | 86.9 |
| | L-Pro | L-Ala-L-Pro | 1.5 |
| | L-Phe | L-Ala-L-Phe | 69.5 |
| | L-Trp | L-Ala-L-Trp | 46.0 |
| | L-Thr | L-Ala-L-Thr | 47.3 |
| | L-Asn | L-Ala-L-Asn | 52.3 |
| | L-Tyr | L-Ala-L-Tyr | 11.1 |
| | L-CySH | L-Ala-L-CySH | + |
| | L-Lys | L-Ala-L-Lys | 71.2 |
| | L-Arg | L-Ala-L-Arg | 72.2 |
| | L-His | L-Ala-L-His | 73.6 |
| | L-Asp | L-Ala-L-Asp | 2.3 |
| | L-Glu | L-Ala-L-Glu | 39.1 |
| | L-Ser | L-Ala-L-Ser | 43.8 |
| | D-Ser | L-Ala-D-Ser | 3.3 |
| D-Ala-OMe | L-Ser | D-Ala-L-Ser | 24.1 |
| | D-Ser | D-Ala-D-Ser | 5.5 |

TABLE 15-2

| Carboxy component | Amine component | Produced peptide | (mM) |
|---|---|---|---|
| L-Thr-OMe | L-Gln | L-Thr-L-Gln | 36.1 |
| Gly-OMe | | Gly-L-Gln | 61.1 |
| L-Ser-OMe | | L-Ser-L-Gln | 12.9 |

TABLE 15-2-continued

| Carboxy component | Amine component | Produced peptide | (mM) |
|---|---|---|---|
| L-Val-OMe | L-Val-L-Gln | | 8.2 |
| L-Met-OMe | L-Met-L-Gln | | 32.6 |
| L-Ile-OMe | L-Ile-L-Gln | | 6.4 |
| L-Arg-OMe | L-Arg-L-Gln | | 17.2 |
| L-Tyr-OMe | L-Tyr-L-Gln | | 0.6 |
| L-Pro-OMe | L-Pro-L-Gln | | 1.8 |
| L-Phe-OMe | L-Phe-L-Gln | | 0.8 |
| L-Gln-OMe | L-Gln-L-Gln | | 0.1 |
| Asp-a-OMe | α-L-Asp-L-Gln | | 0.05 |

TABLE 15-3

| Carboxy component | Amine component | Produced peptide | (mM) |
|---|---|---|---|
| L-Thr-OMe | Gly | L-Thr-Gly | 0.4 |
| | L-Ala | L-Thr-L-Ala | 5.8 |
| | L-Val | L-Thr-L-Val | 1.3 |
| | L-Leu | L-Thr-L-Leu | 15.3 |
| | L-Met | L-Thr-L-Met | 28.9 |
| Gly-OMe | L-Arg | Gly-L-Arg | 17.9 |
| | L-Phe | Gly-L-Phe | 20.0 |
| | L-His | Gly-L-His | 36.2 |
| | L-Lys | Gly-L-Lys | 48.2 |
| | L-Ser | Gly-L-Ser | 53.8 |
| L-Ser-OMe | L-Ser | L-Ser-L-Ser | 9.9 |
| | L-Met | L-Ser-L-Met | 7.6 |
| | L-Phe | L-Ser-L-Phe | 4.3 |
| L-Val-OMe | L-Ser | L-Val-L-Ser | 31.9 |
| | L-Met | L-Val-L-Met | 6.8 |
| | L-Phe | L-Val-L-Phe | 1.0 |
| L-Met-OMe | L-Ser | L-Met-L-Ser | 25.3 |
| | L-Met | L-Met-L-Met | 28.4 |
| | L-Phe | L-Met-L-Phe | 8.9 |
| L-Ile-OMe | L-Ser | L-Ile-L-Ser | 17.3 |
| | L-Met | L-Ile-L-Met | 5.1 |
| | L-Phe | L-Ile-L-Phe | 1.5 |
| L-Arg-OMe | L-Ser | L-Arg-L-Ser | 2.2 |
| | L-Met | L-Arg-L-Met | tr |
| | L-Phe | L-Arg-L-Phe | tr |

TABLE 15-4

| Carboxy component | Amine component | Produced peptide (mM) | |
|---|---|---|---|
| L-Ala-OMe | Gly amide | L-Ala-Gly amide | 15.1 |
| | L-Ala amide | L-Ala-L-Ala amide | 9.2 |
| | L-Phe amide | L-Ala-Phe amide | 27.1 |
| L-Ala-OMe | Methylamine | L-Ala-methylamine | 0.6 |
| L-Thr-OMe | | L-Thr-methylamine | 0.3 |
| Gly-OMe | | Gly-methylamine | 1.0 |
| L-Ala amide | L-Gln | L-Ala-L-Gln | 0.3 |
| | L-Met | L-Ala-L-Met | tr |
| | L-His | L-Ala-L-His | tr |

Hydrochloride salts were used for all the amino acid amides.

Example 25

Substrate Specificity of Enzyme (12)

Substrate specificity with respect to oligopeptide production was examined for enzyme derived from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). 100 μl of 100 mM borate buffer (pH 9.0) containing the various carboxy components at a final concentration of 100 mM and the various amine components at a final concentration of 150 mM shown in Table 16, the SP-Sepharose HP fraction enzyme purified in Example 22 (addition of 0.33 units in the reaction liquid) and 10 mM EDTA were allowed to react for 1.5 hours at 25° C. The amounts of each oligopeptide formed in this reaction are shown in Table 16. Furthermore, hydrochloride salts were used for all carboxy components.

TABLE 16

| Carboxy component | Amine component | Produced peptide (mM) | |
|---|---|---|---|
| L-Ala-OMe | L-Ala | L-Ala-L-Ala | 25.6 |
| | L-Ala-L-Ala | L-Ala-L-Ala-L-Ala | 41.1 |
| | L-Ala-L-Ala-L-Ala | L-Ala-L-Ala-L-Ala-L-Ala | 30.1 |
| | L-Ala-L-Ala-L-Ala-L-Ala | L-Ala-L-Ala-L-Ala-L-Ala-L-Ala | 22.8 |
| | Gly-Gly | L-Ala-Gly-Gly | 33.7 |
| | Gly-Ala | L-Ala-Gly-L-Ala | 35.1 |
| | L-His-L-Ala | L-Ala-L-His-L-Ala | 58.0 |
| | L-Phe-Gly | L-Ala-L-Phe-Gly | 34.0 |
| | L-Leu-L-Ala | L-Ala-L-Leu-L-Ala | 40.7 |
| | L-Phe-L-Ala | L-Ala-L-Phe-L-Ala | 24.8 |
| L-Thr-OMe | Gly-Gly | L-Thr-Gly-Gly | 8.4 |
| Gly-OMe | L-Ala-L-Tyr | Gly-L-Ala-L-Tyr | 0.6 |

Example 26

Substrate Specificity of Enzyme (13)

Substrate specificity was additionally assessed using the same enzyme fraction as that used in Example 5.

TABLE 17

| Carboxy component (mM) | Amine component (mM) | Produced peptide (mM) | Reaction time (hr) |
|---|---|---|---|
| H-Ala-OMe 50 mM | H-p-F-Phe-OH 50 mM | H-Ala-p-F-Phe-OH 21.9 mM | 3 |
| H-Ala-OMe 40 mM | H-Cl-F-Phe-OH 40 mM | H-Ala-Cl-F-Phe-OH 20.8 mM | 3 |
| H-Ala-OMe 40 mM | H-p-NO$_2$-Phe-OH 40 mM | H-Ala-p-NO$_2$-Phe-OH 27.5 mM | 3 |
| H-Ala-OMe 100 mM | H-t-Leu-OH 150 mM | H-Ala-t-Leu-OH 0.4 mM | 3 |
| H-Ala-OMe 20 mM | H-2-Nal-OH 20 mM | H-Ala-2-Nal-OH + | 3 |
| H-p-F-Phe-OMe 100 mM | H-Gln-OH 150 mM | H-p-F-Phe-H-Gln-OH tr | 3 |

TABLE 17-continued

| Carboxy component (mM) | Amine component (mM) | Produced peptide (mM) | Reaction time (hr) |
|---|---|---|---|
| H-Cl-F-Phe-OMe 25 mM | H-Gln-OH 50 mM | H-Cl-F-Phe-H-Gln-OH tr | 3 |
| H-p-NO$_2$-Phe-OMe 40 mM | H-Gln-OH 40 mM | H-p-NO$_2$-Phe-H-Gln-OH 1.1 mM | 3 |
| H-t-Leu-OMe 100 mM | H-Gln-OH 150 mM | H-t-Leu-H-Gln-OH tr | 3 |
| H-2-Nal-OMe 40 mM | H-Gln-OH 40 mM | H-2-Nal-H-Gln-OH tr | 3 |
| H-Aib-OMe 100 mM | H-Gln-OH 150 mM | H-Aib-H-Gln-OH 18.8 mM | 3 |
| H-N-Me-Ala-OMe 100 mM | H-Gln-OH 150 mM | H-N-Me-Ala-H-Gln-OH 0.5 mM | 3 |
| H-Aib-OMe 100 mM | H-Phe-OH 150 mM | H-Aib-Phe-OH 17.2 mM | 3 |
| H-CHA-OMe 40 mM | H-Phe-OH 40 mM | H-CHA-Phe-OH + | 3 |
| H-N-Me-Ala-OMe 100 mM | H-Phe-OH 150 mM | H-N-Me-Ala-Phe-OH tr | 3 |
| H-Ala-OMe 100 mM | H-Ser(tBu)-OH 150 mM | H-Ala-Ser(tBu)-OH 48.8 mM | 2 |
| H-Ser(tBu)-OMe 100 mM | H-Gln-OH 150 mM | H-Ser(tBu)-Gln-OH tr | 2 |
| H-Ala-OMe 100 mM | H-Asp(OtBu)-OH 150 mM | H-Ala-Asp(OtBu)-OH 62.6 mM | 2 |
| H-Asp(OtBu)-OMe 100mM | H-Gln-OH 150 mM | H-Asp(OtBu)-Gln-OH 0.9 mM | 2 |
| H-Ala-OMe 100 mM | H-Lys(Boc)-OH 150 mM | H-Ala-Lys(Boc)-OH 51.0 mM | 2 |
| H-Lys(Boc)-OMe 100 mM | H-Gln-OH 150 mM | H-Lys(Boc)-Gln-OH + | 2 |

100 μl of reaction solutions consisting of 100 mM borate buffer (pH 9.0) containing each of the carboxy components and amine components at the final concentrations shown in Table 17, enzyme (addition of 0.1 unit in reaction solution) and 10 mM EDTA were allowed to react at 25° C. for the reaction times shown in Table 17. The amounts of various peptides formed in the reactions are shown in Table 17. The "+" mark indicates those for which production was confirmed but which were unable to be quantified due to the absence of a standard, while "tr" indicates a trace amount.

Abbreviations

H-Ala-OMe: L-alanine methyl ester hydrochloride
H-p-F-Phe-OMe: p-fluoro-L-phenylalanine methyl ester hydrochloride
H—Cl—F-Phe-OMe: p-chloro-L-phenylalanine methyl ester hydrochloride
H-p-NO$_2$-Phe-OMe: p-nitro-L-phenylalanine methyl ester hydrochloride
H-t-Leu-OMe: tert-L-leucine methyl ester hydrochloride
H-2-Nal-OMe: 3-(2-naphthyl)-L-alanine methyl ester hydrochloride
H-Aib-OMe: α-aminoisobutyric acid methyl ester hydrochloride
H—N-Me-Ala-OMe: N-methyl-L-alanine methyl ester hydrochloride
H—CHA-OMe: β-cyclohexyl-L-alanine methyl ester hydrochloride
H-Ser(tBu)-OMe: O-tert-butyl-L-serine methyl ester hydrochloride
H-Asp(OtBu)-OMe: L-aspartic acid β-tert-butyl ester α-methyl ester hydrochloride
H-Lys(Boc)-OMe: N-ε-tert-butoxycarbonyl-L-lysine methyl ester hydrochloride
H-p-F-Phe-OH: p-fluoro-L-phenylalanine
H-Cl—F-Phe-OH: p-chloro-L-phenylalanine
H-p-NO$_2$-Phe-OH: p-nitro-L-phenylalanine
H-t-Leu-OH: tert-L-leucine
H-2-Nal-OH: 3-(2-naphthyl)-L-alanine
H-Gln-OH: L-glutamine
H-Phe-OH: L-phenylalanine
H-Ser(tBu)-OH: O-tert-butyl-L-serine
H-Asp(OtBu)-OH: L-aspartic acid β-tert-butyl ester
H-Lys(Boc)-OH: N-c-tert-butoxycarbonyl-L-lysine Example 27

Substrate Specificity of Enzyme (14)

Substrate specificity with respect to oligopeptide production was assessed using the same enzyme fraction as Example 5 (derived from *Empedobacter brevis*). 100 μl of reaction solutions consisting of 100 mM borate buffer (pH 9.0) containing each of the carboxy components and amine components at the final concentrations shown in Table 18, enzyme (the numbers of units added to the reaction solution are described in Table 18) and 10 mM EDTA were allowed to react at 25° C. for 3 hours. The amounts of various oligopeptides formed in the reactions are shown in Table 18. A "+" mark indicates those for which production was confirmed but which were unable to be quantified due to the absence of a standard, while "tr" indicates a trace amount. It should be noted that hydrochloride salts were used for all the carboxy components.

TABLE 18

| Carboxy component | Amine component | Amount of enzyme (unit) | Produced peptide | (mM) |
|---|---|---|---|---|
| Gly-OMe | L-Phe-L-Met | 1.0 | Gly-Phe-Met | 13.3 |
| L-Ala-OMe | L-Phe-L-Met | 0.2 | L-Ala-L-Phe-L-Met | + |
| L-Tyr-OMe | Gly-Gly-L-Phe-L-Met | 1.0 | L-Tyr-Gly-Gly-L-Phe-L-Met | 2.7 |
| L-Ala-OMe | Gly-Gly-L-Phe-L-Met | 0.2 | L-Ala-Gly-Gly-L-Phe-L-Met | + |
| Gly-OMe | Gly-L-Phe | 0.1 | Gly-L-Phe | 17.3 |
| L-Ala-OMe | Gly-L-Phe | 0.1 | L-Ala-Gly-L-Phe | + |
| D-Ala-OMe | Gly-L-Phe | 0.1 | D-Ala-Gly-L-Phe | Tr |

Example 28

Isolation of Peptide-Forming Enzyme Gene Derived from *Empedobacter brevis*

Hereinafter, although the following provides a description of the isolation of a peptide-forming enzyme gene, will be explained. As the microbe was used *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was used as the microbe. In isolating the gene, *Escherichia coli* JM-109 was used as a host while pUC118 was used as a vector.

(1) Production of PCR Primer Based on Determined Internal Amino Acid Sequence

A mixed primer having the base sequences indicated in SEQ ID NO.: 3 and SEQ ID NO: 4, respectively, was produced based on the amino acid sequences (SEQ ID NOs: 1 and 2) determined according to the Edman's decomposition method from the a digestion product of lysyl endopeptidase of a peptide-forming enzyme derived from the *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) digested by a lysyl endopeptidase.

(2) Preparation of Microbial Cells

*Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was cultured at 30° C. for 24 hours on a CM2G agar medium (containing glucose at 50 g/l, yeast extract at 10 g/l, peptone at 10 g/l, sodium chloride at 5 g/l, and agar at 20 g/l, pH 7.0). One loopful of the resulting microbial cells was inoculated into a 500 ml Sakaguchi flask containing 50 ml of a CM2G liquid medium (the aforementioned medium excluding agar) followed by shake culturing at 30° C.

(3) Preparation of Chromosomal DNA from Microbial Cells

First, 50 ml of culture broth was centrifuged (12,000 rpm, 4° C., 15 minutes) to collect the microbial cells. Then, a chromosomal DNA was obtained from the microbial cells using the QIAGEN Genomic-Tip System (Qiagen) based on the procedure described in the manual therefor.

(4) Preparation of DNA Fragment Containing Part of Peptide-Forming Enzyme Gene by PCR A DNA fragment containing a portion of the peptide-forming enzyme gene derived from *Empedobacter brevis* strain FERM BP-8113 (Depositary institution: the independent administrative corporation, National Institute of Advanced Industrial Science and Technology, International Patent Organism Depositary, Address of depositary institution: Dai-6, 1-1 Higashi 1-Chome, Tsukuba-shi, Ibaraki-ken, Japan, International deposit transfer date: Jul. 8, 2002) was obtained by the PCR method using LA-Taq (manufactured by Takara Shuzo). A PCR reaction was then carried out on a chromosomal DNA obtained from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) using the primers having the base sequences of SEQ ID NOs: 3 and 4.

The PCR reaction was carried out for 30 cycles under the following conditions using the Takara PCR Thermal Cycler PERSONAL (manufactured by Takara Shuzo).

94° C. 30 seconds
52° C. 1 minute
72° C. 1 minute

After the reaction, 3 µl of the reaction liquid was applied to 0.8% agarose electrophoresis. As a result, it was verified that a DNA fragment of about 1.5 kilobases (kb) was confirmed to be amplified.

(5) Cloning of Peptide-Forming Enzyme Gene from Gene Library

In order to obtain the entire length of peptide-forming enzyme gene in full-length, Southern hybridization was carried out using the DNA fragment amplified in the PCR procedure as a probe. The procedure for Southern hybridization is explained in Molecular Cloning, 2nd edition, Cold Spring Harbor Press (1989).

The approximately 1.5 kb DNA fragment amplified by the PCR procedure was isolated by 0.8% agarose electrophoresis. The target band was then cut out and the DNA fragment was purified. The DNA fragment was labeled with probe digoxinigen using DIG High Prime (manufactured by Boehringer-Mannheim) based on the procedure described in the manual of the kit.

After completely digesting the chromosomal DNA of *Empedobacter brevis* obtained in the step (3) of the present Example 28(3) by reacting at 37° C. for 16 hours with restriction enzyme HindIII, the resultant DNA was electrophoresed with on 0.8% agarose gel. The electrophoresed chromosomal DNA was blotted onto a positively charged Nylon membrane filter (manufactured by Roche Diagnostics) from the agarose gel after the electrophoresis, followed by treatments consisting of alkaline denaturation, neutralization and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed for 20 minutes at room temperature with 2×SSC containing 0.1% SDS. Moreover, the filter was additionally washed twice at 65° C. for 15 minutes with 0.1×SSC.

Detection of bands that hybridized with the probe was carried out using the DIG Nucleotide Detection Kit (manufactured by Boehringer-Mannheim) based on the procedure described in the manual of the kit. As a result, a roughly 4 kb band was able to be detected that hybridized with the probe.

Then, the chromosomal DNA prepared in the step (3) of the present Example 28(3) was completely digested with HindIII. A roughly 4 kb of DNA was separated by 0.8% agarose gel electrophoresis, followed by purification of the DNA using the Gene Clean II Kit (manufactured by Funakoshi) and dissolving the DNA in 10 µl of TE. 4 µl of this product was then mixed with pUC118 HindIII/BAP (manufactured by Takara Shuzo) and a ligation reaction was carried out using the DNA Ligation Kit Ver. 2 (manufactured by Takara Shuzo). 5 µl of the ligation reaction mixture and 100 µl of competent cells of *Escherichia coli* JM109 (manufactured by Toyobo) were mixed to transform the *Escherichia coli*. Thus obtained transformants were then applied to a suitable solid medium to produce a chromosomal DNA library.

To obtain the entire full-length of peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter (Nylon Membrane for Colony and Plaque Hybridization, (manufactured by Roche Diagnostics) followed by treatments consisting of alkali denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added, followed by hybridization at 50° C. for 16 hours. Subsequently, the filter was washed for 20 minutes at room temperature with 2×SSC containing 0.1% SDS. Moreover, the filter was additionally washed twice at 65° C. for 15 minutes with 0.1×SSC.

Detection of colonies that hybridized with the labeled probe was carried out using the DIG Nucleotide Detection Kit (manufactured by Boehringer-Mannheim) based on the explanation described in the manual of the kit. As a result, two colonies were verified to hybridize with the labeled probe.

(6) Base Sequence of Peptide-Forming Enzyme Gene Derived from *Empedobacter brevis*

Plasmids possessed by *Escherichia coli* JM109 were prepared from the aforementioned two colonies that were verified to hybridize with the labeled probe using the Wizard Plus Minipreps DNA Purification System (manufactured by Promega) to and the base sequence of a portion where hybridization with the probe occurred and nearby was determined. The sequencing reaction was carried out using the CEQ DTCS-Quick Start Kit (manufactured by Beckman-Coulter) based on the procedure described in the manual of the kit. In addition, electrophoresis was carried out using the CEQ 2000-XL (manufactured by Beckman-Coulter).

As a result, it was verified that an open reading frame that encodes a protein containing the internal amino acid sequences of the peptide-forming enzyme (SEQ ID NOs: 1 and 2) did exist. Thus, the open reading frame was confirmed to be a gene encoding the peptide-forming enzyme. The base sequence of the full-length of the peptide-forming enzyme genes along with the corresponding amino acid sequences is shown in SEQ ID NO: 5. As a result of analysis on the homology of the resulting open reading frame with the BLASTP program, homology was discovered between the two enzymes; it showed with a homology of 34% as at the amino acid sequence level exhibited with the α-amino acid ester hydrolase of *Acetobacter pasteurianus* (see Appl. Environ. Microbiol., 68(1), 211-218 (2002), and a homology of 26% at the amino acid sequence level exhibited with the glutaryl-7ACA acylase of *Brevibacillus laterosporum* (see J. Bacteriol., 173(24), 7848-7855 (1991).

Example 29

Expression of Peptide-Forming Enzyme Gene Derived from *Empedobacter brevis* in *Escherichia coli*

A target gene region on the promoter region of the trp operon on the chromosomal DNA of *Escherichia coli* W3110 was amplified by carrying out PCR using the oligonucleotides indicated in SEQ ID NOs: 7 and 8 as primers, and the resulting DNA fragments were ligated to a pGEM-Teasy vector (manufactured by Promega). *E. coli* JM109 was then transformed in this ligation solution, and those strains having the target plasmid in which the direction of the inserted trp promoter is inserted in the opposite to the orientation from of the lac promoter were selected from ampicillin-resistant strains. Next, a DNA fragment containing the trp promoter obtained by treating this plasmid with EcoO109I/EcoRI was ligated to an EcoO109I/EcoRI treatment product of pUC19 (manufactured by Takara). *Escherichia coli* JM109 was then transformed with this ligation solution and those strains having the target plasmid were selected from ampicillin-resistant strains. Next, a DNA fragment obtained by treating this plasmid with HindIII/PvuII was ligated with to a DNA fragment containing an rrnB terminator obtained by treating pKK223-3 (manufactured by Amersham Pharmacia) with HindIII/HincII. *E. coli* JM109 was then transformed with this ligation solution, strains having the target plasmid were selected from ampicillin-resistant strains, and the plasmid was designated as pTrpT.

The target gene was amplified by PCR using the chromosomal DNA of *Empedobacter brevis* strain FERM BP-8113 (Depositary institution: the independent administrative corporation, National Institute of Advanced Industrial Science and Technology, International Patent Organism Depositary, Address of depositary institution: Chuo No Chuo Dai-6, 1-1 Higashi 1-Chome, Tsukuba-shi, Ibaraki-ken, Japan, International deposit transfer date: Jul. 8, 2002) as a template and the oligonucleotides indicated in SEQ ID NO: 9 and 10 as primers. This DNA fragment was then treated with NdeI/PstI, and the resulting DNA fragment was ligated with the NdeI/PstI treatment product of pTrpT. *Escherichia coli* JM109 was then transformed with this ligation solution, those strains having the target plasmid were selected from ampicillin-resistant strains, and this plasmid was designated as pTrpT_Gtg2.

*Escherichia coli* JM109 having pTrpT_Gtg2 was pre-cultured at 30° C. for 24 hours in LB medium containing 100 mg/l of ampicillin. 1 ml of the resulting culture broth was inoculated into a 500 ml Sakaguchi flask containing 50 ml of a medium (D glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l, and ampicillin at 100 mg/l), followed by culturing at 25° C. for 24 hours. The culture broth had an L-alanyl-L-glutamine forming activity of 0.44 U per 1 ml of culture broth and it was verified that the cloned gene was expressed by *E. coli*. Furthermore, no activity was detected for a transformant in which only pTrpT had been introduced as a control.

Prediction of Signal Sequence

When the amino acid sequence of SEQ ID NO: 6 described in the Sequence Listing was analyzed with the Signal P v 1.1 program (see Protein Engineering, Vol. 12, No. 1, pp. 3-9, 1999), it was predicted that amino acids numbers 1 to 22 function as a signal for secretion of peptide into the periplasm, while the mature protein was estimated to be downstream of amino acid number 23.

Verification of Secretion

*Escherichia coli* JM109, having pTrpT_Gtg2, was pre-cultured at 30° C. for 24 hours in LB medium containing 100 mg/l of ampicillin. 1 ml of the resulting culture broth was inoculated into a 500 ml Sakaguchi flask containing 50 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l, and ampicillin at 100 mg/l), followed by final culturing at 25° C. for 24 hours to obtain microbial cells.

The cultured microbial cells were fractionated into a periplasm fraction and a cytoplasm fraction after disruption of cells by an osmotic pressure shock method using a 20 grams/deciliter (g/dl) sucrose solution. The disrupted microbial cells immersed in the 20 g/dl sucrose solution were immersed in a 5 mM aqueous MgSO$_4$ solution. The centrifuged supernatant was named a periplasm fraction ("Pe"). In addition, the centrifuged sediment was re-suspended and subjected to ultrasonic disruption. The resultant was named a cytoplasm fraction ("Cy"). The activity of glucose 6-phosphate dehydrogenase, which is known to be present in the cytoplasm, was used as an indicator to verify that the cytoplasm had been separated. This measurement was carried out by adding a suitable amount of enzyme to a reaction solution at 30° C. containing 1 mM glucose 6-phosphate, 0.4 mM NADP, 10 mM $MgSO_4$, and 50 mM Tris-Cl (pH 8), followed by measurement of absorbance at 340 nm to measure production of NADPH.

Figure 4:
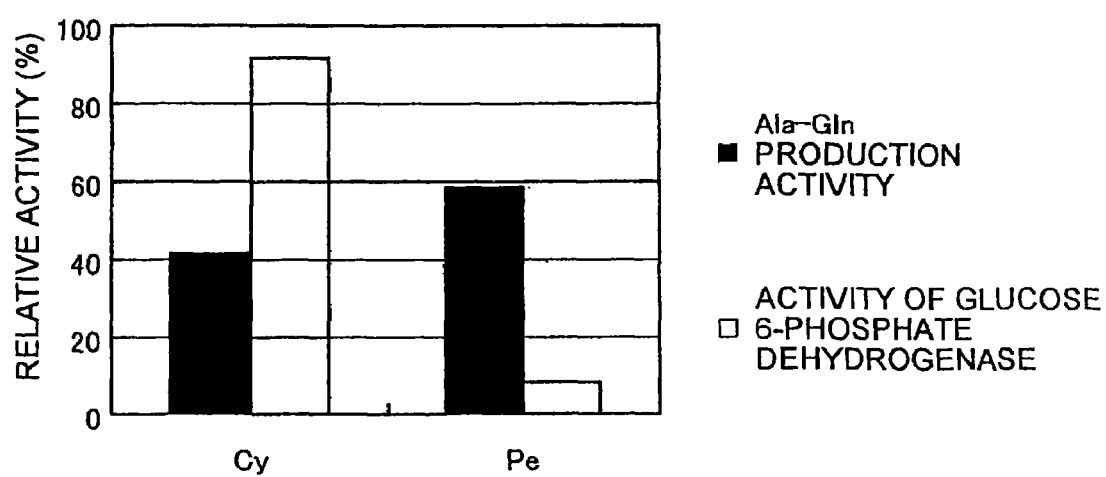
FIG. 4 is a bar graph illustrating the amount of enzyme present in a cytoplasm fraction (Cy) and a periplasm fraction (Pe).

FIG. 4 demonstrates that the amounts of enzymes of in the periplasm fraction and the cytoplasm fraction when the activity of a separately prepared cell-free extract was assigned a value of 100%. The glucose 6-phosphate dehydrogenase activity was not detected in the periplasm fraction. This indicates that the periplasm fraction did not mix in the cytoplasm fraction. About 60% of the Ala-Gln forming activity was recovered in the periplasm fraction, and it was verified that the Ala-Gln forming enzyme was secreted into the periplasm as predicted from the amino acid sequence using the Signal P v 1.1 program.

Example 30

Production of L-Alanyl-L-Glutamine Using Microbial Cells of *Sphingobacterium* sp.

A 50 ml medium (pH 7.0) containing 5 g of glucose, 5 g of ammonium sulfate, 1 g of monopotassium phosphate, 3 g of dipotassium phosphate, 0.5 g of magnesium sulfate, 10 g of yeast extract, and 10 g of peptone in 1 L was transferred to a 500 mL Sakaguchi flask and sterilized at 115° C. for 15 minutes for culturing *Sphingobacterium* sp. strain FERM BP-8124 (Depositary institution: the independent administrative corporation, National Institute of Advanced Industrial Science and Technology, International Patent Organism Depository, Address of depositary institution: Chuo Dai-6, 1-1 Higashi 1-Chome, Tsukuba-shi, Ibaraki-ken, Japan, International deposit date: Jul. 22, 2002). This was then inoculated with one loopful cells of *Sphingobacterium* sp. strain FERM BP-8124 (Depositary institution: National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) cultured at 30° C. for 24 hours in slant agar medium (agar: 20 g/L, pH 7.0) containing 5 g of glucose, 10 g of yeast extract, 10 g of peptone and 5 g of NaCl in 1 L, followed by shake culturing at 30° C. for 20 hours and 120 strokes/minute. 1 ml of this culture broth was then added to the aforementioned medium (50 ml/500 mL Sakaguchi flask) and cultured at 30° C. for 18 hours. After completion of the culture, the microbial cells were separated from the culture broth by centrifugation and suspended in 0.1 M borate buffer (pH 9.0) containing 10 mM EDTA at a concentration of 100 g/L as wet microbial cells. 0.1 mL of 100 mM borate buffer (pH 9.0) containing 10 mM EDTA, 200 mM L-alanine methyl ester hydrochloride and 400 mM L-glutamine was then added to 0.1 mL of this microbial cell suspension. The resulting 0.2 mL of mixture was allowed to react at 25° C. for 120 minutes. The concentration of L-alanyl-L-glutamine produced at this time was 62 mM.

Example 31

Purification of Enzyme from *Sphingobacterium* sp.

The following procedure after centrifugation was carried out either on ice or at 4° C. *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultured in the same manner as Example 21, and the microbial cells were collected by centrifugation (10,000 rpm, 15 minutes). After washing 2 g of microbial cells with 20 mM Tris-HCl buffer (pH 7.6), they were suspended in 8 ml of the same buffer and subjected to ultrasonic disrupting treatment for 45 minutes at 195 W. This ultrasonically disrupted suspension was then centrifuged (10,000 rpm, 30 minutes) to remove the cell debris and obtain a supernatant. This supernatant was dialyzed overnight against 20 mM Tris-HCl buffer (pH 7.6) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 7.6), and the active fraction was collected from the non-adsorbed fraction. This active fraction was dialyzed overnight against 20 mM acetate buffer (pH 5.0), followed by removal of the insoluble fraction by centrifugation (10,000 rpm, 30 minutes) to obtain a dialyzed fraction in the form of the supernatant liquid. This dialyzed fraction was then applied to an SP-Sepharose HP column (manufactured by Amersham) pre-equilibrated with 20 mM acetate buffer (pH 5.0) to obtain the active fraction in which enzyme was eluted at a linear concentration gradient of the same buffer containing 0 to 1 M NaCl.

Example 32

Production of L-Alanyl-L-Glutamine Using Active Fraction

10 µl of the SP-Sepharose HP fraction (about 27 U/ml) purified in Example 31 was added to 90 µl of borate buffer (pH 9.0) containing 111 mM L-alanine methyl ester hydrochloride, 222 mM L-glutamine and 11 mM EDTA, and allowed to react at 25° C. for 120 minutes. As a result, 73 mM of L-alanyl-L-glutamine was produced in the section to which enzyme was added. On the other hand, there was scarcely any production of L-Ala-L-Glu observed in the lot to which enzyme was not added, and the amount produced was only about 0.07 mM after reacting for 120 minutes.

Example 33

Isolation of Peptide-Forming Enzyme Gene Derived from *Sphingobacterium* sp.

Although the following provides a description of the isolation of a peptide-forming enzyme gene, *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was used as the microbe. Gene isolation was carried out using *Escherichia coli* DH5α as the host, and pUC118 as the vector.
(1) Preparation of Microbe

*Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultured at 25° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 25° C.

(2) Preparation of Chromosomal DNA from Microbial Cells 50 ml of culture broth was centrifuged (12,000 rpm, 4° C., 15 minutes) to collect the microbial cells. A chromosomal DNA was then obtained from the microbial cells using the Qiagen Genomic-Tip System (Qiagen) therefor.

(3) Preparation of Probe DNA Fragment by PCR

A DNA fragment containing a portion of the peptide-forming enzyme gene derived from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was obtained by the PCR method using LA-Taq (manufactured by Takara Shuzo). A PCR reaction was then carried out on a chromosomal DNA obtained from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki 1-Chome, Japan, International deposit transfer date: Jul. 8, 2002) using primers having the base sequences of SEQ ID NOs: 3 and 4.

The PCR reaction was carried out for 30 cycles under the following conditions using the Takara PCR Thermal Cycler PERSONAL (manufactured by Takara Shuzo).

94° C. 30 seconds
52° C. 1 minute
72° C. 1 minute

After the reaction, 3 µl of reaction mixture was applied to 0.8% agarose electrophoresis. As a result, a DNA fragment of about 1.5 kb was confirmed to be amplified.

(4) Cloning of Peptide-Forming Enzyme Gene from Gene Library

In order to obtain the entire length of peptide-forming enzyme gene, Southern hybridization was carried out using the DNA fragment amplified in the aforementioned PCR procedure as a probe. The procedure for Southern hybridization is explained in Molecular Cloning, 2nd edition, Cold Spring Harbor Press (1989).

The approximately 1.5 kb DNA fragment amplified by the aforementioned PCR procedure was separated by 0.8% agarose electrophoresis. The target band was then cut out and the DNA fragment was purified. This DNA fragment was labeled with probe digoxinigen using DIG High Prime (manufactured by Boehringer-Mannheim) based on the procedure described in the manual of the kit.

After completely digesting the chromosomal DNA of *Sphingobacterium* sp. obtained in the step (2) of the present Example 33 by reacting at 37° C. for 16 hours with restriction enzyme SacI, it was electrophoresed with 0.8% agarose gel. The electrophoresed chromosomal DNA was blotted onto a positively charged Nylon membrane filter (manufactured by Roche Diagnostics) from the agarose gel following electrophoresis followed by treatment consisting of alkaline denaturation, neutralization and immobilization. Hybridization was carried out using EASY HYB (manufactured by Boehringer-Mannheim). After pre-hybridizing the filter at 37° C. for 1 hour, the probe labeled with digoxinigen prepared as described above was added and hybridization was carried out at 37° C. for 16 hours. Subsequently, the filter was washed twice at 60° C. with 1×SSC containing 0.1% SDS.

Detection of bands that hybridized with the probe was carried out using the DIG Nucleotide Detection Kit (manufactured by Boehringer-Mannheim) based on the procedure described in the manual of the kit. As a result, a roughly 3 kb band was able to be detected that hybridized with the probe.

The chromosomal DNA prepared in the step (2) of the present Example 33 was completely digested with SacI. Roughly 3 kb of DNA was separated by 0.8% agarose gel electrophoresis, followed by purification of the DNA using the Gene Clean II Kit (manufactured by Funakoshi) and dissolving in 10 µl of TE. After allowing 4 µl of this product to react with SacI at 37° C. for 16 hours to completely digest, it was mixed with pUC118 treated with alkaline phosphatase (*E. coli* C75) at 37° C. for 30 minutes and at 50° C. for 30 minutes, and a ligation reaction was carried out using the DNA Ligation Kit Ver. 2 (manufactured by Takara Shuzo). 5 µl of this ligation reaction liquid and 100 µl of competent cells of *Escherichia coli* DH5α (manufactured by Takara Shuzo) were mixed to transform the *Escherichia coli*. Thus obtained transformants were then applied to a suitable solid medium to produce a chromosomal DNA library.

In order to obtain the entire length of peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter—Nylon Membrane for Colony and Plaque Hybridization (manufactured by Roche Diagnostics), followed by treatment consisting of alkaline denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 1% SDS.

Detection of colonies that hybridized with the labeled probe was carried out using the DIG Nucleotide Detection Kit (manufactured by Boehringer-Mannheim) based on the explanation described in the manual of the kit. As a result, six strains of colonies were confirmed to hybridize with the labeled probe.

(5) Base Sequence of Peptide-Forming Enzyme Gene Derived from *Sphingobacterium* sp.

Plasmids possessed by *Escherichia coli* DH5α were prepared from the aforementioned six strains of microbial cells which were confirmed to hybridize with the labeled probe using the Wizard Plus Minipreps DNA Purification System (manufactured by Promega) to determine the nearby base sequences that hybridized with the probe. The sequencing reaction was carried out using the CEQ DTCS-Quick Start Kit (manufactured by Beckman-Coulter) based on the procedure described in the manual of the kit. In addition, electrophoresis was carried out using the CEQ 2000-XL (manufactured by Beckman-Coulter).

As a result, an open reading frame that encodes peptide-forming enzyme was found to exist. The base sequence of the full-length peptide-forming enzyme gene derived from *Sphingobacterium* sp. along with the corresponding amino acid sequence is shown in SEQ ID NO: 11. The peptide-forming enzyme derived from *Sphingobacterium* sp. exhibited homology of 63.5% at the amino acid sequence level with the peptide-forming enzyme derived from the aforementioned *Empedobacter brevis* (as determined using the BLASTP program).

Example 34

Expression of Peptide-Forming Enzyme Gene Derived from *Sphingobacterium* sp. in *Escherichia coli*

The target gene was amplified by carrying out PCR using a chromosomal DNA of *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) as template and the oligonucleotides shown in SEQ ID NOs: 13 and 14 as primers. This DNA fragment was treated with NdeI/XbaI, and the resulting DNA fragment and NdeI/XbaI treatment product of pTrpT were ligated. *Escherichia coli* JM109 was then transformed with this ligation solution, strains having the target plasmid were selected from ampicillin-resistant strains, and the plasmid was designated as pTrpT_Sm_aet.

*Escherichia coli* JM109 having pTrpT_Sm_aet was cultured at 25° C. for 20 hours by inoculating one loopful cells of the strain into an ordinary test tube containing 3 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l). Cloned gene having L-alanyl-L-glutamine production activity of 2.1 U per 1 ml of culture liquid was confirmed to be expressed by *E. coli*. Furthermore, activity was not detected for a transformant containing only pTrpT used as a control.
Prediction of Signal Sequence When the amino acid sequence of SEQ ID NO: 12 described in the Sequence Listing was analyzed with the Signal P v1.1 program (see Protein Engineering, Vol. 12, No. 1, pp. 3-9, 1999), it was predicted that amino acids numbers 1 to 20 function as a signal for secretion of peptide into the periplasm, while the mature protein was estimated to be downstream of amino acid number 21.
Confirmation of Signal Sequence

*Escherichia coli* JM109, having pTrpT_Sm_aet, was cultured at 25° C. for 20 hours by inoculating one loopful cells of the strain into an ordinary test tube containing 50 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l).

The following procedure after centrifugation was carried out either on ice or at 4° C. Following completion of culturing, the microbial cells were separated from the culture broth by centrifugation, and after washing with 100 mM phosphate buffer (pH 7), were suspended in the same buffer. The microbial cells were then subjected to ultrasonic disruption for 20 minutes at 195 W, the ultrasonically disrupted liquid was centrifuged (12,000 rpm, 30 minutes) to remove the cell debris and obtain a soluble fraction. The resulting soluble fraction was applied to a CHT-II column (manufactured by Biorad) pre-equilibrated with 100 mM phosphate buffer (pH 7), and enzyme was eluted at a linear concentration gradient by 500 mM phosphate buffer. A solution obtained by mixing the active fraction with a 5-fold volume of 2 M ammonium sulfate and 100 mM phosphate buffer was applied to a Resource-PHE column (Amersham) pre-equilibrated with 2 M ammonium sulfate and 100 mM phosphate buffer, and enzyme was eluted at a linear concentration gradient by 2 to 0 M ammonium sulfate to obtain an active fraction solution. As a result of these procedures, the peptide-forming enzyme was confirmed to be uniformly purified in terms of electrophoresis.

When the amino acid sequence of the aforementioned peptide-forming enzyme was determined by Edman's decomposition method, the amino acid sequence of SEQ ID NO: 15 was obtained, and the mature protein was confirmed to be downstream from amino acid number 21 as was predicted by the SignalP v 1.1 program.

Example 35

Isolation of Peptide-Forming Enzyme Gene Derived from *Pedobacter heparinus* IFO 12017

Hereinafter, the isolation of a peptide-forming enzyme gene will be described. The microbe used is *Pedobacter heparinus* strain IFO 12017 (Depositary institution: Institute of Fermentation, Address of depositary institution: 2-17-85 Jusanbon-cho, Yodogawa-ku, Osaka-shi, Japan). *Escherichia coli* JM-109 was used as a host while pUC118 was used as a vector in isolating the gene.
(1) Preparation of Microbe

*Pedobacter heparinus* strain IFO-12017 (Depositary institution: Institute of Fermentation, Address of depositary institution: 2-17-85 Jusanbon-cho, Yodogawa-ku, Osaka-shi, Japan) was cultured at 25° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells were inoculated into a 500 ml Sakaguchi flask containing 50 ml of CM2G liquid medium (the aforementioned medium excluding agar) followed by shake culturing at 25° C.
(2) Preparation of Chromosomal DNA from Microbial Cells 50 ml of culture broth was centrifuged (12,000 rpm, 4° C., 15 minutes) to collect the microbial cells. A chromosomal DNA was then obtained from the microbial cells using the Qiagen Genomic-Tip System (Qiagen) based on the procedure described in the manual therefor.
(3) Preparation of Probe DNA Fragment by PCR A DNA fragment containing a portion of the peptide-forming enzyme gene derived from Pedobacter heparinus strain IFO-12017 (Depositary institution: Institute of Fermentation, Address of depositary institution: 2-17-85 Jusanbon-cho, Yodogawa-ku, Osaka-shi, Japan) was obtained by the PCR method using LA-Taq (manufactured by Takara Shuzo). A PCR reaction was then carried out on a chromosomal DNA obtained from Pedobacter heparinus strain IFO-12017 (Depositary institution: Institute of Fermentation, Address of depositary institution: 2-17-85 Jusanbon-cho, Yodogawa-ku, Osaka-shi, Japan) using primers having the base sequences of SEQ ID NOs: 15 and 16. A DNA fragment of about 1 kb amplified by PCR was separated by 0.8% agarose electrophoresis. The target band was then cut out and thus obtained DNA fragment was purified. This DNA fragment was labeled with probe digoxinigen using DIG High Prime based on the procedure described in the manual (manufactured by Boehringer-Mannheim).
(4) Cloning of Peptide-Forming Enzyme Gene from Gene Library To obtain the full-length peptide-forming enzyme gene, Southern hybridization was carried out using the DNA fragment amplified in the aforementioned PCR procedure as a probe. The procedure for Southern hybridization is explained in Molecular Cloning, 2nd edition, Cold Spring Harbor Press (1989).

After completely digesting the chromosomal DNA of Pedobacter heparinus strain IFO-12017 (Depositary institution: Institute of Fermentation, Address of depositary institution: 2-17-85 Jusanbon-cho, Yodogawa-ku, Osaka-shi, Japan) by reacting at 37° C. for 16 hours with restriction enzyme HindIII, it was electrophoresed with 0.8% agarose gel. The electrophoresed chromosomal DNA was blotted onto a positively charged Nylon membrane filter (manufactured by Roche Diagnostics) from the agarose gel after the electrophoresis, followed by treatment consisting of alkali denaturation, neutralization, and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed twice at 60° C. with 1×SSC containing 0.1% SDS.

Detection of bands that hybridized with the probe was carried out based on the procedure described in the manual using the DIG Nucleotide Detection Kit (manufactured by Boehringer-Mannheim). As a result, a roughly 5 kb band was able to be detected that hybridized with the probe.

The chromosomal DNA of Pedobacter heparinus strain IFO-12017 (Depositary institution: Institute of Fermentation, Address of depositary institution: 2-17-85 Jusanbon-cho, Yodogawa-ku, Osaka-shi, Japan) were completely digested with HindIII. Roughly 5 kb of DNA were separated by 0.8% agarose gel electrophoresis followed by purification of the DNA using the Gene Clean II Kit (manufactured by Funakoshi) and dissolving in 10 μl of TE. 4 μl of this product was then mixed with pUC118 HindIII/BAP (manufactured by Takara Shuzo) and a ligation reaction was carried out using the DNA Ligation Kit Ver. 2 (manufactured by Takara Shuzo). 5 μl of this ligation reaction liquid and 100 μl of competent cells of Escherichia coli JM109 (manufactured by Takara Shuzo) were mixed to transform the Escherichia coli. The obtained transformants were then applied to a suitable solid medium to produce a chromosomal DNA library.

In order to obtain the full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization, (manufactured by Roche Diagnostics), followed by treatment consisting of alkali denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 1% SDS.

Detection of colonies that hybridized with the labeled probe was carried out based on the explanation described in the manual using the DIG Nucleotide Detection Kit (manufactured by Boehringer-Mannheim). As a result, 1 strain of colonies was confirmed to hybridize with the labeled probe.
(5) Base Sequence of Peptide-Forming Enzyme Gene Derived from *Pedobacter heparinus* Strain IFO-12017

Plasmids retained by Escherichia coli JM109 were prepared from the aforementioned strain of microbial cells which were confirmed to hybridize with the labeled probe, and the nearby base sequence that hybridized with the probe was determined. The sequencing reaction was carried out using the CEQ DTCS-Quick Start Kit (manufactured by Beckman-Coulter) based on the procedure described in the manual. In addition, electrophoresis was carried out using the CEQ 2000-XL (Beckman-Coulter).

As a result, an open reading frame that encodes peptide-forming enzyme was found to exist. The base sequence of the full-length peptide-forming enzyme gene derived from *Pedobacter heparinus* strain IFO-12017 (Depositary institution: Institute of Fermentation, Address of depositary institution: 2-17-85 Jusanbon-cho, Yodogawa-ku, Osaka-shi, Japan), along with the corresponding amino acid sequence, is shown in SEQ ID NO: 17 of the Sequence Listing.

Example 36

Expression of Peptide-Forming Enzyme Gene Derived from *Pedobacter heparinus* strain IFO-12017 in *E. coli*

The target gene was amplified by carrying out PCR using a chromosomal DNA of *Pedobacter heparinus* strain IFO-12017 (Depositary institution: Institute of Fermentation, Osaka, Address of depositary institution: 2-17-85 Jusanbon-cho, Yodogawa-ku, Osaka-shi, Japan) as template and the oligonucleotides shown in SEQ ID NOs: 19 and 20 as primers. This DNA fragment was treated with NdeI/HindIII, and the resulting DNA fragment and NdeI/HindIII treatment product of pTrpT were ligated. *Escherichia coli* JM109 was then transformed with this ligation solution, strains having the target plasmid were selected from ampicillin-resistant strains, and the plasmid was designated as pTrpT_Ph_aet.

*Escherichia coli* JM109 having pTrpT_Ph_aet was cultured at 25° C. for 20 hours by inoculating one loopful cells of the strain into an ordinary test tube containing 3 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l). A cloned gene having L-alanyl-L-glutamine production activity of 0.3 U per ml of culture liquid was confirmed to be expressed in *E. coli*. Furthermore, no activity was detected for a transformant containing only pTrpT used as a control.

Example 37

Isolation of Peptide-Forming Enzyme Gene Derived from *Taxeobacter gelupurpurascens* strain DSMZ 11116

Hereinafter, the isolation of peptide-forming enzyme gene will be described. The microbe used is *Taxeobacter gelupurpurascens* strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany) was used for the microbe. *Escherichia coli* JM-109 was used as a host while pUC118 was used as a vector in isolating the gene.
(1) Preparation of Microbe

*Taxeobacter gelupurpurascens* strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany)

was cultured at 25° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells were inoculated into a 500 ml Sakaguchi flask containing 50 ml of CM2G liquid medium (the aforementioned medium excluding agar) followed by shake culturing at 25° C.

(2) Preparation of Chromosomal DNA from Microbial Cells 50 ml of culture liquid were centrifuged (12,000 rpm, 4° C., 15 minutes) to collect the microbial cells. A chromosomal DNA was then obtained from the microbial cells using the Qiagen Genomic-Tip System (Qiagen) based on the procedure described in the manual therefor.

(3) Preparation of Probe DNA Fragment by PCR

A DNA fragment containing a portion of the peptide-forming enzyme gene derived from Taxeobacter gelupurpurascens strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany) was obtained by the PCR method using LA-Taq (manufactured by Takara Shuzo). A PCR reaction was then carried out on a chromosomal DNA obtained from Taxeobacter gelupurpurascens strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany) using primers having the base sequences of SEQ ID NOs: 21 and 16. A DNA fragment of about 1 kb amplified by PCR was separated by 0.8% agarose electrophoresis. The target band was then cut out and the DNA fragment was purified. This DNA fragment was labeled with probe digoxinigen using DIG High Prime (manufactured by Boehringer-Mannheim) based on the procedure described in the manual.

(4) Cloning of Peptide-Forming Enzyme Gene from Gene Library

To obtain the full-length peptide-forming enzyme gene, Southern hybridization was carried out using the DNA fragment amplified in the aforementioned PCR procedure as a probe. The procedure for Southern hybridization is explained in Molecular Cloning, 2nd edition, Cold Spring Harbor Press (1989).

After completely digesting the chromosomal DNA of Taxeobacter gelupurpurascens strain DSMZ 11116 (Depositary institution: Deutche Sammlung von Mikroorganismen und Zellkulturen GmbH (German Collection of Microbes and Cell Cultures), Address of depositary institution: Mascheroder Weg 1b, 38124 Braunschweig, Germany) by reacting at 37° C. for 16 hours with restriction enzyme PstI, it was electrophoresed with 0.8% agarose gel. The electrophoresed chromosomal DNA was blotted onto a positively charged Nylon membrane filter (manufactured by Roche Diagnostics) from the agarose gel following electrophoresis followed by treatment consisting of alkali denaturation, neutralization and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed twice at 60° C. with 1×SSC containing 0.1% SDS.

Detection of bands that hybridized with the probe was carried out based on the procedure described in the manual using the DIG Nucleotide Detection Kit (manufactured by Boehringer-Mannheim). As a result, a roughly 5 kb band was able to be detected that hybridized with the probe.

The chromosomal DNA of Taxeobacter gelupurpurascens strain DSMZ 11116 (Depositary institution: Deutche Sammlung von Mikroorganismen and Zellkulturen GmbH (German Collection of Microbes and Cell Cultures), Address of depositary institution: Mascheroder Weg 1b, 38124 Braunschweig, Germany) were completely digested with HindIII. Roughly 5 kb of DNA were separated by 0.8% agarose gel electrophoresis followed by purification of the DNA using the Gene Clean II Kit (manufactured by Funakoshi) and dissolving in 10 μl of TE. 4 μl of this product were then mixed with pUC118 PstI/BAP (manufactured by Takara Shuzo) and a ligation reaction was carried out using the DNA Ligation Kit Ver. 2 (manufactured by Takara Shuzo). 5 μl of this ligation reaction liquid and 100 μl of competent cells of Escherichia coli JM109 (manufactured by Takara Shuzo) were mixed to transform the Escherichia coli. Thus obtained transformants were then applied to a suitable solid medium to produce a chromosomal DNA library.

In order to obtain the entire length of peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization, (manufactured by Roche Diagnostics) followed by treatment consisting of alkaline denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 0.1% SDS.

Detection of colonies that hybridized with the labeled probe was carried out based on the manual using the DIG Nucleotide Detection Kit (manufactured by Boehringer-Mannheim). As a result, 1 strain of colonies was confirmed to hybridize with the labeled probe.

(5) Base Sequence of Peptide-Forming Enzyme Gene Derived from Taxeobacter gelupurpurascens Strain DSMZ 11116

Plasmids retained by Escherichia coli JM109 were prepared from the aforementioned strain of microbial cells which were confirmed to hybridize with the labeled probe, and the nearby base sequence that hybridized with the probe was determined. The sequencing reaction was carried out using the CEQ DTCS-Quick Start Kit (manufactured by Beckman-Coulter) based on the procedure described in the manual. In addition, electrophoresis was carried out using the CEQ 2000-XL (manufactured by Beckman-Coulter).

As a result, an open reading frame that encodes peptide-forming enzyme was found to exist. The base sequence of the entire length of the peptide-forming enzyme gene derived from Taxeobacter gelupurpurascens strain DSMZ 11116 (Depositary institution: Deutche Sammlung von Mikroorganismen and Zellkulturen GmbH (German Collection of Microbes and Cell Cultures), Address of depositary institution: Mascheroder Weg 1b, 38124 Braunschweig, Germany), along with the corresponding amino acid sequence, are shown in SEQ ID NO: 22 of the Sequence Listing.

Example 38

Isolation of Peptide-Forming Enzyme Gene Derived from Cyclobacterium marinum Strain ATCC 25205

Hereinafter, the isolation of peptide-forming enzyme gene will be described. The microbe used is Cyclobacterium mari-

*num* strain ATCC 25205 (Depositary institution: American Type Culture Collection, Address of depositary institution: P.O. Box 1549, Manassas, Va. 20110, the United States of America). *Escherichia coli* JM-109 was used as a host while pUC118 was used for the vector in isolating the gene.

(1) Preparation of Microbial Cells

*Cyclobacterium marinum* strain ATCC 25205 (Depositary institution: American Type Culture Collection, Address of depositary institution: P.O. Box 1549, Manassas, Va. 20110, the United States of America) was cultured at 25° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells was inoculated into a 500 ml Sakaguchi flask containing 50 ml of CM2G liquid medium (the aforementioned medium excluding agar), followed by shake culturing at 25° C.

(2) Preparation of Chromosomal DNA from Microbial Cells 50 ml of culture broth were centrifuged (12,000 rpm, 4° C., 15 minutes) to collect the microbial cells. A chromosomal DNA was then obtained from the microbial cells based on the procedure described in the manual using the Qiagen Genomic-Tip System (Qiagen).

(3) Preparation of Probe DNA Fragment by PCR

A DNA fragment containing a portion of the peptide-forming enzyme gene derived from Cyclobacterium marinum strain ATCC 25205 (Depositary institution: American Type Culture Collection, Address of depositary institution: P.O. Box 1549, Manassas, Va. 20110, the United States of America) was obtained by the PCR method using LA-Taq (manufactured by Takara Shuzo). A PCR reaction was then carried out on a chromosomal DNA obtained from Cyclobacterium marinum strain ATCC 25205 (Depositary institution: American Type Culture Collection, Address of depositary institution: P.O. Box 1549, Manassas, Va. 20110, the United States of America) using primers having the base sequences of SEQ ID NOs: 15 and 16. A DNA fragment of about 1 kb amplified by PCR was separated by 0.8% agarose electrophoresis. The target band was then cut out and the DNA fragment was purified. This DNA fragment was labeled with probe digoxinigen based on the procedure described in the manual using DIG High Prime (manufactured by Boehringer-Mannheim).

(4) Cloning of Peptide-Forming Enzyme Gene from Gene Library

In order to obtain the full-length peptide-forming enzyme gene, Southern hybridization was first carried out using the DNA fragment amplified in the aforementioned PCR procedure as a probe. The procedure for Southern hybridization is explained in Molecular Cloning, 2nd edition, Cold Spring Harbor Press (1989).

After completely digesting the chromosomal DNA of *Cyclobacterium marinum* strain ATCC 25205 (Depositary institution: American Type Culture Collection, Address of depositary institution: P.O. Box 1549, Manassas, Va. 20110, the United States of America) by reacting at 37° C. for 16 hours with restriction enzyme HincII, each was electrophoresed with 0.8% agarose gel. The electrophoresed chromosomal DNA was blotted onto a positively charged Nylon membrane filter (manufactured by Roche Diagnostics) from the agarose gel following electrophoresis followed by treatment consisting of alkali denaturation, neutralization and immobilization. Hybridization was carried out using EASY HYB (manufactured Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed twice at 60° C. with 1×SSC containing 0.1% SDS.

Detection of bands that hybridized with the probe was carried out based on the procedure described in the manual using the DIG Nucleotide Detection Kit (manufactured by Boehringer-Mannheim). As a result, a roughly 7 k band was able to be detected that hybridized with the probe in the PstI digestion product, while a 2 k band was able to be detected that hybridized with the probe in the HincII digestion product.

The chromosomal DNA of Cyclobacterium marinum strain ATCC 25205 (Depositary institution: American Type Culture Collection, Address of depositary institution: P.O. Box 1549, Manassas, Va. 20110, the United States of America) were completely digested with PstI or HincII. Roughly 7 kb or 2 kb of DNA were respectively separated by 0.8% agarose gel electrophoresis, followed by purification of the DNA using the Gene Clean II Kit (Funakoshi) and dissolving in 10 µl of TE. 4 µl of this product were then mixed with pUC118 PstI/BAP (manufactured by Takara Shuzo) or pUC118 HincII/BAP (manufactured by Takara Shuzo) and a ligation reaction was carried out using the DNA Ligation Kit Ver. 2 (manufactured by Takara Shuzo). 5 µl of this ligation reaction liquid and 100 µl of competent cells of *Escherichia coli* JM109 (manufactured by Takara Shuzo) were respectively mixed to transform the *Escherichia coli*. Thus obtained transformants were then applied to a suitable solid medium to produce a chromosomal DNA library.

To obtain the full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization, (manufactured by Roche Diagnostics), followed by treatment consisting of alkali denaturation, neutralization, and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 0.1% SDS. Detection of colonies that hybridized with the labeled probe was carried out based on the manual using the DIG Nucleotide Detection Kit (manufactured by Boehringer-Mannheim). As a result, 1 strain of colonies each was confirmed to hybridize with the labeled probe.

(5) Base Sequence of Peptide-Forming Enzyme Gene Derived from *Cyclobacterium marinum* Strain ATCC 25205

Plasmids retained by *Escherichia coli* JM109 were prepared from each of the aforementioned strains of microbial cells which were confirmed to hybridize with the labeled probe, and the nearby base sequence that hybridized with the probe was determined. The sequencing reaction was carried out using the CEQ DTCS-Quick Start Kit (manufactured by Beckman-Coulter) based on the procedure described in the manual of the kit. In addition, electrophoresis was carried out using the CEQ 2000-XL (manufactured by Beckman-Coulter).

As a result, an open reading frame that encodes peptide-forming enzyme was found to exist. The base sequence of the full-length peptide-forming enzyme gene derived from *Cyclobacterium marinum* strain ATCC 25205 (Depositary institution: American Type Culture Collection, Address of depositary institution: P.O. Box 1549, Manassas, Va. 20110, the United States of America), along with the corresponding amino acid sequence, is shown in SEQ ID NO: 24 of the Sequence Listing.

Example 39

Isolation of Peptide-Forming Enzyme Gene Derived from *Psycloserpens burtonensis* Strain ATCC 700359

Hereinafter, the isolation of a peptide-forming enzyme gene will be explained. The microbe used is *Psycloserpens burtonensis* strain ATCC 700359 (Depositary institution: American Type Culture Collection, Address of depositary institution: P.O. Box 1549, Manassas, Va. 20110, the United States of America). *Escherichia coli* JM-109 was used for the host while pUC118 was used for the vector in isolating the gene.

(1) Preparation of Microbe

*Psycloserpens burtonensis* strain ATCC 700359 (Depositary institution: American Type Culture Collection, Address of depositary institution: P.O. Box 1549, Manassas, Va. 20110, the United States of America) was cultured at 10° C. for 24 hours on CM2G agar medium (containing glucose at 50 g/l, yeast extract at 10 g/l, peptone at 10 g/l, sodium chloride at 5 g/l and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 10° C.

(2) Preparation of Chromosomal DNA from Microbial Cells 50 ml of culture liquid were centrifuged (12,000 rpm, 4° C., 15 minutes) to collect the microbial cells. A chromosomal DNA was then obtained from the microbial cells using the Qiagen Genomic-Tip System (Qiagen) based on the procedure described in the manual therefor.

(3) Preparation of Probe DNA Fragment by PCR

A DNA fragment containing a portion of the peptide-forming enzyme gene derived from *Psycloserpens burtonensis* strain ATCC 700359 (Depositary institution: American Type Culture Collection, Address of depositary institution: P.O. Box 1549, Manassas, Va. 20110, the United States of America) was obtained by the PCR method using LA-Taq (manufactured by Takara Shuzo). A PCR reaction was then carried out on a chromosomal DNA obtained from *Psycloserpens burtonensis* strain ATCC 700359 (Depositary institution: American Type Culture Collection, Address of depositary institution: P.O. Box 1549, Manassas, Va. 20110, the United States of America) using primers having the base sequences of SEQ ID NOs: 15 and 16. A DNA fragment of about 1 kb amplified by PCR was separated by 0.8% agarose electrophoresis. The target band was then cut out and the DNA fragment was purified. This DNA fragment was labeled with probe digoxinigen based on the procedure described in the manual using DIG High Prime (manufactured by Boehringer-Mannheim).

(4) Cloning of Peptide-Forming Enzyme Gene from Gene Library

In order to obtain the entire length of peptide-forming enzyme gene, Southern hybridization was carried out using the DNA fragment amplified in the aforementioned PCR procedure as a probe. The procedure for Southern hybridization is explained in Molecular Cloning, 2nd edition, Cold Spring Harbor Press (1989).

After completely digesting the chromosomal DNA of *Psycloserpens burtonensis* strain ATCC 700359 (Depositary institution: American Type Culture Collection, Address of depositary institution: P.O. Box 1549, Manassas, Va. 20110, the United States of America) by reacting at 37° C. for 16 hours with restriction enzyme EcoRI, it was electrophoresed with 0.8% agarose gel. The electrophoresed chromosomal DNA was blotted onto a positively charged Nylon membrane filter (manufactured by Roche Diagnostics) from the agarose gel following electrophoresis followed by treatment consisting of alkaline denaturation, neutralization and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed twice at 60° C. with 1×SSC containing 0.1% SDS.

Detection of bands that hybridized with the probe was carried out using the DIG Nucleotide Detection Kit (manufactured by Boehringer-Mannheim) based on the procedure described in the manual of the kit. As a result, a roughly 7 kb band was able to be detected that hybridized with the probe.

The chromosomal DNA of *Psycloserpens burtonensis* strain ATCC 700359 (Depositary institution: American Type Culture Collection, Address of depositary institution: P.O. Box 1549, Manassas, Va. 20110, the United States of America) were completely digested with EcoRI. Roughly 7 kb of DNA were separated by 0.8% agarose gel electrophoresis followed by purification of the DNA using the Gene Clean II Kit (manufactured by Funakoshi) and dissolving in 10 µl of TE. 4 µl of this product were then mixed with pUC118 EcoRI/BAP (manufactured by Takara Shuzo) and a ligation reaction was carried out using the DNA Ligation Kit Ver. 2 (manufactured by Takara Shuzo). 5 µl of this ligation reaction liquid and 100 µl of competent cells of *Escherichia coli* JM109 (manufactured by Takara Shuzo) were mixed to transform the *Escherichia coli*. Thus obtained transformants were then applied to a suitable solid medium to produce a chromosomal DNA library.

To obtain the full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization, (manufactured by Roche Diagnostics), followed by treatment consisting of alkali denaturation, neutralization, and immobilization. Hybridization was carried out using EASY HYB (manufactured by Boehringer-Mannheim). After pre-hybridizing the filter at 37° C. for 1 hour, the aforementioned probe labeled with digoxinigen was added followed by hybridizing at 37° C. for 16 hours. Subsequently, the filter was washed twice at 60° C. with 1×SSC containing 0.1% SDS.

Detection of colonies that hybridized with the labeled probe was carried out based on the manual using the DIG Nucleotide Detection Kit (manufactured by Boehringer-Mannheim). As a result, 1 strain of colonies was confirmed to hybridize with the labeled probe.

(5) Base Sequence of Peptide-Forming Enzyme Gene Derived from *Psycloserpens burtonensis* Strain ATCC 700359

Plasmids retained by *Escherichia coli* JM109 were prepared from the aforementioned strain of microbial cells which were confirmed to hybridize with the labeled probe, and the nearby base sequence that hybridized with the probe was determined. The sequencing reaction was carried out using the CEQ DTCS-Quick Start Kit (manufactured by Beckman-Coulter) based on the procedure described in the manual. In addition, electrophoresis was carried out using the CEQ 2000-XL (manufactured by Beckman-Coulter).

As a result, an open reading frame that encodes peptide-forming enzyme was found to exist. The base sequence of the full-length peptide-forming enzyme gene derived from *Psycloserpens burtonensis* strain ATCC 700359 (Depositary institution: American Type Culture Collection, Address of depositary institution: P.O. Box 1549, Manassas, Va. 20110, the United States of America), along with the corresponding amino acid sequence, are shown in SEQ ID NO: 26 of the Sequence Listing.

INDUSTRIAL APPLICABILITY

According to the present invention, a novel enzyme is provided that can produce a peptide easily, at high yield and inexpensively by reducing complex synthetic methods such as introduction and elimination of protecting groups. The use of the enzyme of the present invention enables efficient industrial production of a peptide.

SEQUENCE LISTING

SEQ ID NO: 3: Synthetic primer 1
SEQ ID NO: 4: Synthetic primer 2
SEQ ID NO: 5: Gene encoding a peptide-forming enzyme
SEQ ID NO: 7: Synthetic primer for preparing pTrpT
SEQ ID NO: 8: Synthetic primer for preparing pTrpT
SEQ ID NO: 9: Synthetic primer for preparing pTrpT_Gtg2
SEQ ID NO: 10: Synthetic primer for preparing pTrpT_Gtg2
SEQ ID NO: 11: Gene encoding peptide-forming enzyme
SEQ ID NO: 13: Synthetic primer for preparing pTrpT_Sm_aet
SEQ ID NO: 14: Synthetic primer for preparing pTrpT_Sm_aet
SEQ ID NO: 15: Mix primer 1 for Aet
SEQ ID NO: 16: Mix primer 2 for Aet
SEQ ID NO: 19: Primer 1 for constructing aet expression vectors derived from *Pedobacter*.
SEQ ID NO: 20: Primer 2 for constructing aet expression vectors derived from *Pedobacter*.
SEQ ID NO: 21: Mix primer 3 for Aet

What we claim is:

1. An isolated DNA encoding a protein selected from the group consisting of (I), (J), (U), and (V), wherein said protein has an amino acid sequence defined as follows:

(I) the amino acid sequence consisting of amino acid residues numbers 26 to 620 of SEQ ID NO:25, (J) an amino acid sequence which includes substitution, deletion, insertion, and/or addition, of one to 30 amino acids in the amino acid sequence consisting of amino acid residues numbers 26 to 620 of SEQ ID NO:25, and has at least 50% of the peptide-forming activity of a protein corresponding to unmutated amino acid residue numbers 26 to 620 of SEQ ID NO:25 at 50° C. and a pH of 8, (U) the amino acid sequence consisting of SEQ ID NO:25, and (V) an amino acid sequence which includes substitution, deletion, insertion, and/or addition, of one to 30 amino acids in the amino acid sequence consisting of SEQ ID NO:25, and has at least 50% of the peptide-forming activity of a protein corresponding to unmutated SEQ ID NO:25 at 50° C. and a pH of 8, or an isolated DNA selected from the group consisting of (i), (i2), and (u), wherein said DNA has a nucleotide sequence defined as follows:

(i) a nucleotide sequence consisting of nucleotide numbers 104 to 1888 of SEQ ID NO:24, (i2) a nucleotide sequence that hybridizes under stringent conditions with a DNA having a nucleotide sequence complementary to a nucleotide sequence consisting of nucleotide numbers 104 to 1888 of SEQ ID NO:24 under stringent conditions, wherein said stringent conditions are 0.1×SSC and 0.1% SDS at 65° C., and encodes a protein that has at least 50% of the peptide-forming activity at 50° C. and a pH of 8 of a protein encoded by unmutated nucleotide numbers 104 to 1888 of SEQ ID NO:24, (s) a nucleotide sequence consisting of nucleotide numbers 29 to 1888 of SEQ ID NO:24.

2. The isolated DNA of claim 1, wherein said DNA encodes a protein having an amino acid sequence defined as follows:

(I) the amino acid sequence consisting of amino acid residues numbers 26 to 620 of SEQ ID NO:25, or (U) the amino acid sequence consisting of SEQ ID NO:25.

3. The isolated DNA of claim 1, wherein, in the protein of (J) and (V) the number of substitution, deletion, insertion and/or addition is 1 to 10 amino acid residues.

4. The isolated DNA of claim 1, wherein said DNA has a nucleotide sequence defined as follows:
   (i) a nucleotide sequence consisting of nucleotide numbers 104 to 1888 of SEQ ID NO:24, or
   (u) a nucleotide sequence consisting of nucleotide numbers 29 to 1888 of SEQ ID NO:24.

5. A recombinant DNA comprising the DNA according to claim 1.

6. A transformed cell comprising the recombinant DNA according to claim 5.

7. A method for producing a peptide-forming enzyme comprising:
   culturing the transformed cell according to claim 6 in a medium for a time and under conditions suitable to produce the peptide-forming enzyme, and
   accumulating the peptide-forming enzyme in the medium and/or transformed cell.

8. A method for producing a dipeptide comprising:
   culturing the transformed cell according to claim 6 in a medium for a time and under conditions suitable to produce a peptide-forming enzyme in a culture, and
   mixing the culture with a carboxy component and an amine component to synthesize a dipeptide by enzymatic catalysis facilitated by a peptide-forming enzyme encoded by said DNA;
   wherein said carboxy component is an amino acid ester or an amino acid amide; and
   wherein said amine component is selected from the group consisting of an amino acid and a C-protected amino acid.

9. The method for producing a dipeptide according to claim 8, wherein said transformed cell is a microbe belonging to the genus *Escherichia* that has an ability to form the dipeptide from the carboxy component and the amine component.

10. A method for producing a dipeptide comprising:
    culturing the transformed cell according to claim 6 in a medium for a time and under conditions suitable to produce a peptide-forming enzyme,
    recovering said transformed cell from said culture, and
    mixing the recovered transformed cell with a carboxy component and an amine component to synthesize a dipeptide by enzymatic catalysis facilitated by a peptide-forming enzyme encoded by said DNA;
    wherein said carboxy component is an amino acid ester or an amino acid amide; and
    wherein said amine component is selected from the group consisting of an amino acid and a C-protected amino acid.

11. A method for producing a dipeptide comprising:
    culturing the transformed cell according to claim 6 in a medium for a time and under conditions suitable to produce a peptide-forming enzyme;
    recovering said transformed cell from said culture;
    treating said transformed cell to produce a microbial cell product
    wherein said treating is selected from the group consisting of acetone treating, freeze-drying, disrupting, and lysing; and
    mixing said microbial cell product with a carboxy component and an amine component to synthesize a dipeptide by enzymatic catalysis facilitated by a peptide-forming enzyme encoded by said DNA;
    wherein said carboxy component is an amino acid ester or an amino acid amide; and
    wherein said amine component is selected from the group consisting of an amino acid and a C-protected amino acid.

* * * * *

```
                              SEQUENCE LISTING

<160> NUMBER OF SEQ ID NOS: 27

<210> SEQ ID NO 1
<211> LENGTH: 9
<212> TYPE: PRT
<213> ORGANISM: Empedobacter brevis

<400> SEQUENCE: 1

Leu Phe Thr Ala Ile Tyr Gln Pro Lys
1               5

<210> SEQ ID NO 2
<211> LENGTH: 9
<212> TYPE: PRT
<213> ORGANISM: Empedobacter brevis

<400> SEQUENCE: 2

Thr Asn Val Thr Tyr Thr Met Pro Asp
1               5

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = a, c, g, or t
<220> FEATURE:
<221> NAME/KEY: misc_feature
<222> LOCATION: (9)..(9)
<223> OTHER INFORMATION: n = a, c, g, or t

<400> SEQUENCE: 3
ttyacngcna thtaycarcc                                                    20

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA
```

```
<220> FEATURE:
<221> NAME/KEY: misc_feature
<222> LOCATION: (3)..(3)
<223> OTHER INFORMATION: n = a, c, g, or t
<220> FEATURE:
<221> NAME/KEY: misc_feature
<222> LOCATION: (9)..(9)
<223> OTHER INFORMATION: n = a, c, g, or t
<220> FEATURE:
<221> NAME/KEY: misc_feature
<222> LOCATION: (15)..(15)
<223> OTHER INFORMATION: n = a, c, g, or t
<220> FEATURE:
<221> NAME/KEY: misc_feature
<222> LOCATION: (18)..(18)
<223> OTHER INFORMATION: n = a, c, g, or t

<400> SEQUENCE: 4
tcnggcatng trtangtnac rtt                                              23

<210> SEQ ID NO 5
<211> LENGTH: 2024
<212> TYPE: DNA
<213> ORGANISM: Empedobacter brevis
<220> FEATURE:
<221> NAME/KEY: CDS
<222> LOCATION: (61)..(1908)
<223> OTHER INFORMATION:

<400> SEQUENCE: 5
atttcttaat aaaaactgaa atcttaatac atttatacta tcgtaaaatt tattgaacac      60 gtg aaa aaa tta aca tta aaa gta act cta ctt aca ctt ttg ttg gga      108
Val Lys Lys Leu Thr Leu Lys Val Thr Leu Leu Thr Leu Leu Leu Gly
1               5                  10                  15 agt aca gtt gga ttt gcg caa gat gca aaa gca gat tct gct tat gtg      156
Ser Thr Val Gly Phe Ala Gln Asp Ala Lys Ala Asp Ser Ala Tyr Val
                20                  25                  30 cgc gac aat tac gaa aaa ata gaa caa gta att ccg atg cgc gat ggt      204
Arg Asp Asn Tyr Glu Lys Ile Glu Gln Val Ile Pro Met Arg Asp Gly
            35                  40                  45 aca aag tta ttt aca gct att tat cag cca aaa gat aaa aca aaa caa      252
Thr Lys Leu Phe Thr Ala Ile Tyr Gln Pro Lys Asp Lys Thr Lys Gln
        50                  55                  60 tat ccc gtt ttg tta aat cgt acg cct tat aca gtt gcg cct tat ggt      300
Tyr Pro Val Leu Leu Asn Arg Thr Pro Tyr Thr Val Ala Pro Tyr Gly
65                  70                  75                  80 gta aat gaa tac aag aaa tcg tta gga aat ttt cct aca gaa atg cgc      348
Val Asn Glu Tyr Lys Lys Ser Leu Gly Asn Phe Pro Thr Glu Met Arg
                85                  90                  95 gaa ggt ttt att ttt gtt tac caa gat gtg aga gga aaa tgg atg agc      396
Glu Gly Phe Ile Phe Val Tyr Gln Asp Val Arg Gly Lys Trp Met Ser
                100                 105                 110 gaa ggc gaa ttt gaa gat gtt cga cct ata aat cct tca aaa agt aaa      444
Glu Gly Glu Phe Glu Asp Val Arg Pro Ile Asn Pro Ser Lys Ser Lys
            115                 120                 125 aag gca att gac gaa agc aca gat aca ttt gat acg cta gaa tgg ctt      492
Lys Ala Ile Asp Glu Ser Thr Asp Thr Phe Asp Thr Leu Glu Trp Leu
        130                 135                 140 gct aaa aac ttg aag aat tac acg aaa aaa gct gga att tat gga att      540
Ala Lys Asn Leu Lys Asn Tyr Thr Lys Lys Ala Gly Ile Tyr Gly Ile
145                 150                 155                 160 tcg tat cct ggt ttt tat tcg aca atg agt ttg gtt aat tcg cat cca      588
Ser Tyr Pro Gly Phe Tyr Ser Thr Met Ser Leu Val Asn Ser His Pro
                165                 170                 175 act cta aaa gcc gtt tcg cca caa gcg ccc gtt acc aat tgg ttt tta      636
```

```
                Thr Leu Lys Ala Val Ser Pro Gln Ala Pro Val Thr Asn Trp Phe Leu
                            180                 185                 190 ggt gac gat ttt cat cat aat gga gtt tta ttc ttg aat gat tct ttc           684
Gly Asp Asp Phe His His Asn Gly Val Leu Phe Leu Asn Asp Ser Phe
            195                 200                 205 tca ttt atg act ttt ttt ggt gta aaa cgt ccg caa cca att acg cca           732
Ser Phe Met Thr Phe Phe Gly Val Lys Arg Pro Gln Pro Ile Thr Pro
    210                 215                 220 gat aaa ggt ccg aaa cgt ttt gaa tat cca ata aaa gat aat tat aga           780
Asp Lys Gly Pro Lys Arg Phe Glu Tyr Pro Ile Lys Asp Asn Tyr Arg
225                 230                 235                 240 ttt tat gca agt ggc tct gta aaa gag ttg aaa gat aaa tat ttg caa           828
Phe Tyr Ala Ser Gly Ser Val Lys Glu Leu Lys Asp Lys Tyr Leu Gln
                245                 250                 255 gat aat atc aag ttt tac aat gat tta ttt gcg cat cca gat tac gat           876
Asp Asn Ile Lys Phe Tyr Asn Asp Leu Phe Ala His Pro Asp Tyr Asp
            260                 265                 270 caa ttt tgg caa gat cgt aat gtt tta cca cat tta act aac gtg caa           924
Gln Phe Trp Gln Asp Arg Asn Val Leu Pro His Leu Thr Asn Val Gln
    275                 280                 285 cct gct gta atg acg gtt gga ggt ttt ttt gat gca gaa gat gtc tac           972
Pro Ala Val Met Thr Val Gly Gly Phe Phe Asp Ala Glu Asp Val Tyr
290                 295                 300 ggc gct ttc gaa acg tat aaa gca att gag aaa caa aat ccg aaa gca          1020
Gly Ala Phe Glu Thr Tyr Lys Ala Ile Glu Lys Gln Asn Pro Lys Ala
305                 310                 315                 320 aca aat att atg gtt gcc gga cct tgg ttt cat ggt ggt tgg gtt cgt          1068
Thr Asn Ile Met Val Ala Gly Pro Trp Phe His Gly Gly Trp Val Arg
                325                 330                 335 agc aac gga agt act ttt gga gat atg caa ttt gca tcg aat aca agt          1116
Ser Asn Gly Ser Thr Phe Gly Asp Met Gln Phe Ala Ser Asn Thr Ser
            340                 345                 350 gag cat tat cag caa gaa ata gaa ttg cct ttt ttt aat tat tac tta          1164
Glu His Tyr Gln Gln Glu Ile Glu Leu Pro Phe Phe Asn Tyr Tyr Leu
    355                 360                 365 aaa gat aaa ggt aat ttt aaa cca acc gaa gct aca att ttt att acg          1212
Lys Asp Lys Gly Asn Phe Lys Pro Thr Glu Ala Thr Ile Phe Ile Thr
370                 375                 380 gga tct aac gaa tgg aaa caa ttt gat gct tgg cca cca aaa aat gta          1260
Gly Ser Asn Glu Trp Lys Gln Phe Asp Ala Trp Pro Pro Lys Asn Val
385                 390                 395                 400 aca aca caa aaa att tat ttg caa caa aat ggt aaa ata gct ttt aat          1308
Thr Thr Gln Lys Ile Tyr Leu Gln Gln Asn Gly Lys Ile Ala Phe Asn
                405                 410                 415 aaa acc aat aca aca act act ttt gac gaa tat gtt gca gat cca aat          1356
Lys Thr Asn Thr Thr Thr Thr Phe Asp Glu Tyr Val Ala Asp Pro Asn
            420                 425                 430 tct cca gtt cct tat tca gga gga gtt tta gaa act cgt tca aga gaa          1404
Ser Pro Val Pro Tyr Ser Gly Gly Val Leu Glu Thr Arg Ser Arg Glu
    435                 440                 445 tat atg gtc gat gat caa cgc ttt gct tct act cgt cct gat gtt atg          1452
Tyr Met Val Asp Asp Gln Arg Phe Ala Ser Thr Arg Pro Asp Val Met
450                 455                 460 gtg tat caa tct gat att ttg aca gaa gat att acg ctt gct ggt cct          1500
Val Tyr Gln Ser Asp Ile Leu Thr Glu Asp Ile Thr Leu Ala Gly Pro
465                 470                 475                 480 gtt atc aat cat tta gtg gtt tct act cgg aca gac gct gat tat          1548
Val Ile Asn His Leu Val Val Ser Thr Thr Gly Thr Asp Ala Asp Tyr
                485                 490                 495 gtt gta aaa ttg att gat gtt tat cct gaa aac acg cca aaa ttt aat          1596
```

```
Val Val Lys Leu Ile Asp Val Tyr Pro Glu Asn Thr Pro Lys Phe Asn
            500                 505                 510 aac aaa tta atg gct gga tat caa aat ttg att cgt gca gaa att atg      1644
Asn Lys Leu Met Ala Gly Tyr Gln Asn Leu Ile Arg Ala Glu Ile Met
            515                 520                 525 cgc gga aaa tat aga aat agt ttc tct aac ccc gaa gct atg gtt ccg      1692
Arg Gly Lys Tyr Arg Asn Ser Phe Ser Asn Pro Glu Ala Met Val Pro
            530                 535                 540 aat aaa gaa aca aat gta acg tac acg atg cca gat gtt gga cat aca      1740
Asn Lys Glu Thr Asn Val Thr Tyr Thr Met Pro Asp Val Gly His Thr
545                 550                 555                 560 ttt aag aaa gga cat cgc att atg att caa gtt cag aac agt tgg ttt      1788
Phe Lys Lys Gly His Arg Ile Met Ile Gln Val Gln Asn Ser Trp Phe
            565                 570                 575 cct tta gca gat cgc aat ccg caa caa ttt atg aat gtt tac gaa gca      1836
Pro Leu Ala Asp Arg Asn Pro Gln Gln Phe Met Asn Val Tyr Glu Ala
            580                 585                 590 act tct aaa gat tat tta aaa caa acg caa cga att tat cat act tct      1884
Thr Ser Lys Asp Tyr Leu Lys Gln Thr Gln Arg Ile Tyr His Thr Ser
            595                 600                 605 tat atc gaa att ccg gta ttg aaa taacaaaaaa atccagctaa ttagctggat     1938
Tyr Ile Glu Ile Pro Val Leu Lys
    610                 615 ttttttata atgttacttt tcctattttt cctttatttc caactaaaat tacatatttt     1998
ttatcgggcg aaaccgtaca agtatg                                          2024

<210> SEQ ID NO 6
<211> LENGTH: 616
<212> TYPE: PRT
<213> ORGANISM: Empedobacter brevis

<400> SEQUENCE: 6

Val Lys Lys Leu Thr Leu Lys Val Thr Leu Leu Thr Leu Leu Leu Gly
1               5                   10                  15

Ser Thr Val Gly Phe Ala Gln Asp Ala Lys Ala Asp Ser Ala Tyr Val
                20                  25                  30

Arg Asp Asn Tyr Glu Lys Ile Glu Gln Val Ile Pro Met Arg Asp Gly
            35                  40                  45

Thr Lys Leu Phe Thr Ala Ile Tyr Gln Pro Lys Asp Lys Thr Lys Gln
        50                  55                  60

Tyr Pro Val Leu Leu Asn Arg Thr Pro Tyr Thr Val Ala Pro Tyr Gly
65                  70                  75                  80

Val Asn Glu Tyr Lys Lys Ser Leu Gly Asn Phe Pro Thr Glu Met Arg
                85                  90                  95

Glu Gly Phe Ile Phe Val Tyr Gln Asp Val Arg Gly Lys Trp Met Ser
            100                 105                 110

Glu Gly Glu Phe Glu Asp Val Arg Pro Ile Asn Pro Ser Lys Ser Lys
        115                 120                 125

Lys Ala Ile Asp Glu Ser Thr Asp Thr Phe Asp Thr Leu Glu Trp Leu
130                 135                 140

Ala Lys Asn Leu Lys Asn Tyr Thr Lys Lys Ala Gly Ile Tyr Gly Ile
145                 150                 155                 160

Ser Tyr Pro Gly Phe Tyr Ser Thr Met Ser Leu Val Asn Ser His Pro
                165                 170                 175

Thr Leu Lys Ala Val Ser Pro Gln Ala Pro Val Thr Asn Trp Phe Leu
            180                 185                 190

Gly Asp Asp Phe His His Asn Gly Val Leu Phe Leu Asn Asp Ser Phe
```

```
            195                 200                 205
Ser Phe Met Thr Phe Phe Gly Val Lys Arg Pro Gln Pro Ile Thr Pro
210                 215                 220

Asp Lys Gly Pro Lys Arg Phe Glu Tyr Pro Ile Lys Asp Asn Tyr Arg
225                 230                 235                 240

Phe Tyr Ala Ser Gly Ser Val Lys Glu Leu Lys Asp Lys Tyr Leu Gln
                245                 250                 255

Asp Asn Ile Lys Phe Tyr Asn Asp Leu Phe Ala His Pro Asp Tyr Asp
                260                 265                 270

Gln Phe Trp Gln Asp Arg Asn Val Leu Pro His Leu Thr Asn Val Gln
                275                 280                 285

Pro Ala Val Met Thr Val Gly Gly Phe Phe Asp Ala Glu Asp Val Tyr
290                 295                 300

Gly Ala Phe Glu Thr Tyr Lys Ala Ile Glu Lys Gln Asn Pro Lys Ala
305                 310                 315                 320

Thr Asn Ile Met Val Ala Gly Pro Trp Phe His Gly Gly Trp Val Arg
                325                 330                 335

Ser Asn Gly Ser Thr Phe Gly Asp Met Gln Phe Ala Ser Asn Thr Ser
                340                 345                 350

Glu His Tyr Gln Gln Glu Ile Glu Leu Pro Phe Phe Asn Tyr Tyr Leu
                355                 360                 365

Lys Asp Lys Gly Asn Phe Lys Pro Thr Glu Ala Thr Ile Phe Ile Thr
370                 375                 380

Gly Ser Asn Glu Trp Lys Gln Phe Asp Ala Trp Pro Pro Lys Asn Val
385                 390                 395                 400

Thr Thr Gln Lys Ile Tyr Leu Gln Gln Asn Gly Lys Ile Ala Phe Asn
                405                 410                 415

Lys Thr Asn Thr Thr Thr Phe Asp Glu Tyr Val Ala Asp Pro Asn
                420                 425                 430

Ser Pro Val Pro Tyr Ser Gly Gly Val Leu Thr Arg Ser Arg Glu
                435                 440                 445

Tyr Met Val Asp Asp Gln Arg Phe Ala Ser Thr Arg Pro Asp Val Met
450                 455                 460

Val Tyr Gln Ser Asp Ile Leu Thr Glu Asp Ile Thr Leu Ala Gly Pro
465                 470                 475                 480

Val Ile Asn His Leu Val Ser Thr Thr Gly Thr Asp Ala Asp Tyr
                485                 490                 495

Val Val Lys Leu Ile Asp Val Tyr Pro Glu Asn Thr Pro Lys Phe Asn
                500                 505                 510

Asn Lys Leu Met Ala Gly Tyr Gln Asn Leu Ile Arg Ala Glu Ile Met
                515                 520                 525

Arg Gly Lys Tyr Arg Asn Ser Phe Ser Asn Pro Glu Ala Met Val Pro
530                 535                 540

Asn Lys Glu Thr Asn Val Thr Tyr Thr Met Pro Asp Val Gly His Thr
545                 550                 555                 560

Phe Lys Lys Gly His Arg Ile Met Ile Gln Val Gln Asn Ser Trp Phe
                565                 570                 575

Pro Leu Ala Asp Arg Asn Pro Gln Gln Phe Met Asn Val Tyr Glu Ala
                580                 585                 590

Thr Ser Lys Asp Tyr Leu Lys Gln Thr Gln Arg Ile Tyr His Thr Ser
                595                 600                 605

Tyr Ile Glu Ile Pro Val Leu Lys
610                 615
```

<210> SEQ ID NO 7
<211> LENGTH: 40
<212> TYPE: DNA
<213> ORGANISM: Artificial Sequence
<220> FEATURE:
<223> OTHER INFORMATION: Synthetic DNA

<400> SEQUENCE: 7
gtatcacgag gccctagctg tggtgtcatg gtcggtgatc                     40

<210> SEQ ID NO 8
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8
ttcggggatt ccatatgata cccttttac gtgaacttgc                      40

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9
gggaattcca tatgaaaaaa ttaacattaa aagtaact                       38

<210> SEQ ID NO 10
<211> LENGTH: 36
<212> TYPE: DNA
<213> ORGANISM: Artificial Sequence
<220> FEATURE:
<223> OTHER INFORMATION: Synthetic DNA

<400> SEQUENCE: 10
gggggctgca gtacttgtac ggtttcgccc gataaa                         36

<210> SEQ ID NO 11
<211> LENGTH: 1935
<212> TYPE: DNA
<213> ORGANISM: Sphingobacterium sp.
<220> FEATURE:
<221> NAME/KEY: CDS
<222> LOCATION: (61)..(1917)
<223> OTHER INFORMATION:

<400> SEQUENCE: 11
gaaaccaagt gtaaaattat aatttacacc aaagaatgta ctgaacaaat aattatctga    60 atg aaa aat aca att tcg tgc cta act tta gcg ctt tta agc gca agc     108
Met Lys Asn Thr Ile Ser Cys Leu Thr Leu Ala Leu Leu Ser Ala Ser
1               5                   10                  15 cag tta cat gct caa aca gct gcc gac tcg gct tat gtt aga gat cat     156
Gln Leu His Ala Gln Thr Ala Ala Asp Ser Ala Tyr Val Arg Asp His
            20                  25                  30 tat gaa aag acc gaa gta gca att ccc atg cga gat ggg aaa aaa tta     204
Tyr Glu Lys Thr Glu Val Ala Ile Pro Met Arg Asp Gly Lys Lys Leu
        35                  40                  45 ttt act gcg atc tac agt cca aaa gac aaa tcc aag aaa tat cca gtt     252
Phe Thr Ala Ile Tyr Ser Pro Lys Asp Lys Ser Lys Lys Tyr Pro Val
    50                  55                  60 ttg ctc aat aga acg ccc tac acg gtt tca cct tat ggg cag aac gaa     300
Leu Leu Asn Arg Thr Pro Tyr Thr Val Ser Pro Tyr Gly Gln Asn Glu

|   |   |   |   |   |   |   |   |   |   |   |   |   |   |   |   |
|---|---|---|---|---|---|---|---|---|---|---|---|---|---|---|---|
| | | 65 | | | | 70 | | | | 75 | | | | 80 | |
| tat | aaa | aaa | agc | ttg | gga | aac | ttt | ccc | caa | atg | atg | cgt | gaa | ggc | tat | 348 |
| Tyr | Lys | Lys | Ser | Leu | Gly | Asn | Phe | Pro | Gln | Met | Met | Arg | Glu | Gly | Tyr | |
| | | | | 85 | | | | | 90 | | | | | 95 | | |
| att | ttc | gtt | tac | cag | gat | gtc | cgt | ggc | aag | tgg | atg | agc | gaa | ggt | gat | 396 |
| Ile | Phe | Val | Tyr | Gln | Asp | Val | Arg | Gly | Lys | Trp | Met | Ser | Glu | Gly | Asp | |
| | | | 100 | | | | | 105 | | | | | 110 | | | |
| ttt | gaa | gat | ata | cgt | ccg | acc | acg | tac | agc | aaa | gat | aaa | aaa | gca | atc | 444 |
| Phe | Glu | Asp | Ile | Arg | Pro | Thr | Thr | Tyr | Ser | Lys | Asp | Lys | Lys | Ala | Ile | |
| | | 115 | | | | | 120 | | | | | 125 | | | | |
| gat | gaa | agt | acg | gat | acc | tat | gat | gcg | ctt | gaa | tgg | tta | cag | aaa | aat | 492 |
| Asp | Glu | Ser | Thr | Asp | Thr | Tyr | Asp | Ala | Leu | Glu | Trp | Leu | Gln | Lys | Asn | |
| | 130 | | | | | 135 | | | | | 140 | | | | | |
| ctc | aaa | aac | tat | aat | ggc | aaa | gcc | ggg | ctc | tat | ggg | att | tcc | tat | cca | 540 |
| Leu | Lys | Asn | Tyr | Asn | Gly | Lys | Ala | Gly | Leu | Tyr | Gly | Ile | Ser | Tyr | Pro | |
| 145 | | | | | 150 | | | | | 155 | | | | | 160 | |
| ggc | ttc | tat | tct | acc | gtc | gga | ttg | gtc | aaa | aca | cac | ccg | agc | ttg | aag | 588 |
| Gly | Phe | Tyr | Ser | Thr | Val | Gly | Leu | Val | Lys | Thr | His | Pro | Ser | Leu | Lys | |
| | | | | 165 | | | | | 170 | | | | | 175 | | |
| gca | gtc | tcc | cca | cag | gct | ccc | gta | aca | gac | tgg | tat | atc | ggc | gac | gac | 636 |
| Ala | Val | Ser | Pro | Gln | Ala | Pro | Val | Thr | Asp | Trp | Tyr | Ile | Gly | Asp | Asp | |
| | | | 180 | | | | | 185 | | | | | 190 | | | |
| ttc | cac | cat | aat | ggc | gta | ttg | ttt | ctt | cag | gat | gca | ttt | aca | ttc | atg | 684 |
| Phe | His | His | Asn | Gly | Val | Leu | Phe | Leu | Gln | Asp | Ala | Phe | Thr | Phe | Met | |
| | | 195 | | | | | 200 | | | | | 205 | | | | |
| tca | acc | ttt | ggt | gtc | cct | cgt | cca | aaa | ccc | att | aca | ccg | gat | caa | ttt | 732 |
| Ser | Thr | Phe | Gly | Val | Pro | Arg | Pro | Lys | Pro | Ile | Thr | Pro | Asp | Gln | Phe | |
| | 210 | | | | | 215 | | | | | 220 | | | | | |
| aag | ggc | aaa | att | cag | atc | aaa | gaa | gcc | gat | aaa | tat | aac | ttt | ttt | gca | 780 |
| Lys | Gly | Lys | Ile | Gln | Ile | Lys | Glu | Ala | Asp | Lys | Tyr | Asn | Phe | Phe | Ala | |
| 225 | | | | | 230 | | | | | 235 | | | | | 240 | |
| gaa | gca | gga | aca | gcg | cgg | gaa | ctc | aaa | gaa | aag | tat | ttt | ggt | gac | tcc | 828 |
| Glu | Ala | Gly | Thr | Ala | Arg | Glu | Leu | Lys | Glu | Lys | Tyr | Phe | Gly | Asp | Ser | |
| | | | | 245 | | | | | 250 | | | | | 255 | | |
| gta | caa | ttt | tgg | aat | gac | ctg | ttt | aag | cat | ccc | gac | tat | gat | gat | ttt | 876 |
| Val | Gln | Phe | Trp | Asn | Asp | Leu | Phe | Lys | His | Pro | Asp | Tyr | Asp | Asp | Phe | |
| | | | 260 | | | | | 265 | | | | | 270 | | | |
| tgg | aaa | tcg | cgt | gtg | atc | acg | aat | tct | tta | cag | gag | gta | aaa | cca | gct | 924 |
| Trp | Lys | Ser | Arg | Val | Ile | Thr | Asn | Ser | Leu | Gln | Glu | Val | Lys | Pro | Ala | |
| | | 275 | | | | | 280 | | | | | 285 | | | | |
| gtg | atg | gtg | gtt | ggt | ggt | ttc | ttt | gac | gcg | gaa | gat | gct | tat | gga | aca | 972 |
| Val | Met | Val | Val | Gly | Gly | Phe | Phe | Asp | Ala | Glu | Asp | Ala | Tyr | Gly | Thr | |
| | 290 | | | | | 295 | | | | | 300 | | | | | |
| ttt | aag | acc | tac | caa | tcg | att | gag | gat | aaa | agc | aaa | aaa | aac | aac | tcg | 1020 |
| Phe | Lys | Thr | Tyr | Gln | Ser | Ile | Glu | Asp | Lys | Ser | Lys | Lys | Asn | Asn | Ser | |
| 305 | | | | | 310 | | | | | 315 | | | | | 320 | |
| att | tta | gtc | gcg | gga | cct | tgg | tat | cat | ggc | ggt | tgg | gtt | cgt | gca | gaa | 1068 |
| Ile | Leu | Val | Ala | Gly | Pro | Trp | Tyr | His | Gly | Gly | Trp | Val | Arg | Ala | Glu | |
| | | | | 325 | | | | | 330 | | | | | 335 | | |
| gga | aac | tat | tta | ggt | gat | atc | caa | ttt | gag | aaa | aaa | acc | agt | att | act | 1116 |
| Gly | Asn | Tyr | Leu | Gly | Asp | Ile | Gln | Phe | Glu | Lys | Lys | Thr | Ser | Ile | Thr | |
| | | | 340 | | | | | 345 | | | | | 350 | | | |
| tat | cag | gaa | caa | ttt | gaa | caa | cca | ttt | ttc | aaa | tat | tac | cta | aaa | gat | 1164 |
| Tyr | Gln | Glu | Gln | Phe | Glu | Gln | Pro | Phe | Phe | Lys | Tyr | Tyr | Leu | Lys | Asp | |
| | | 355 | | | | | 360 | | | | | 365 | | | | |
| gaa | gga | aac | ttc | gcc | cct | tcc | gaa | gct | aac | att | ttt | gtt | tca | ggc | agc | 1212 |
| Glu | Gly | Asn | Phe | Ala | Pro | Ser | Glu | Ala | Asn | Ile | Phe | Val | Ser | Gly | Ser | |
| | 370 | | | | | 375 | | | | | 380 | | | | | |
| aac | gaa | tgg | aaa | cat | ttc | gaa | cag | tgg | cca | cca | aaa | aat | gta | gag | aca | 1260 |
| Asn | Glu | Trp | Lys | His | Phe | Glu | Gln | Trp | Pro | Pro | Lys | Asn | Val | Glu | Thr | |

```
                385                 390                 395                 400
aaa aaa cta tac ttc caa cct cag ggg aaa ctt gga ttt gac aaa gtt      1308
Lys Lys Leu Tyr Phe Gln Pro Gln Gly Lys Leu Gly Phe Asp Lys Val
                405                 410                 415 caa cgt aca gat tcc tgg gat gaa tat gta aca gac cct aat aaa cct      1356
Gln Arg Thr Asp Ser Trp Asp Glu Tyr Val Thr Asp Pro Asn Lys Pro
                420                 425                 430 gtt ccg cat caa ggt ggg gta att caa aac cga aca cgg gag tat atg      1404
Val Pro His Gln Gly Gly Val Ile Gln Asn Arg Thr Arg Glu Tyr Met
                435                 440                 445 gta gat gat caa cgt ttc gcg gct agt cgc cct gat gtc atg gtt tat      1452
Val Asp Asp Gln Arg Phe Ala Ala Ser Arg Pro Asp Val Met Val Tyr
                450                 455                 460 caa acg gaa ccg ttg acg gag gac ctg acg ata gta ggc cca atc aaa      1500
Gln Thr Glu Pro Leu Thr Glu Asp Leu Thr Ile Val Gly Pro Ile Lys
465                 470                 475                 480 aac ttt ctc aaa gtt tct tca aca gga aca gac gcg gac tat gtt gtc      1548
Asn Phe Leu Lys Val Ser Ser Thr Gly Thr Asp Ala Asp Tyr Val Val
                485                 490                 495 aaa ctg att gac gtt tat ccg aat gat gca gca agt tat caa gga aaa      1596
Lys Leu Ile Asp Val Tyr Pro Asn Asp Ala Ala Ser Tyr Gln Gly Lys
                500                 505                 510 aca atg gct gga tat caa atg atg gta cgt ggt gag atc atg gcg ggg      1644
Thr Met Ala Gly Tyr Gln Met Met Val Arg Gly Glu Ile Met Ala Gly
                515                 520                 525 aaa tac cga aat ggt ttc gat aaa gcg cag gcc ttg act cca ggt atg      1692
Lys Tyr Arg Asn Gly Phe Asp Lys Ala Gln Ala Leu Thr Pro Gly Met
                530                 535                 540 gtc gaa aag gtg aat ttt gaa atg cca gac gtt gcg cat acc ttc aaa      1740
Val Glu Lys Val Asn Phe Glu Met Pro Asp Val Ala His Thr Phe Lys
545                 550                 555                 560 aaa gga cat cgc att atg gtt cag gta caa aac tca tgg ttt ccg ctg      1788
Lys Gly His Arg Ile Met Val Gln Val Gln Asn Ser Trp Phe Pro Leu
                565                 570                 575 gca gaa cga aat cca cag gtg ttt tta gca cct tat aca gct acc aaa      1836
Ala Glu Arg Asn Pro Gln Val Phe Leu Ala Pro Tyr Thr Ala Thr Lys
                580                 585                 590 gct gat ttc cgc aaa gct acc caa cgt att ttt cac gat gtg aac aat      1884
Ala Asp Phe Arg Lys Ala Thr Gln Arg Ile Phe His Asp Val Asn Asn
                595                 600                 605 gcc aca tac atc gaa ttt tct gtc ctc aaa gat tagcaggtaa attcgaaa    1935
Ala Thr Tyr Ile Glu Phe Ser Val Leu Lys Asp
                610                 615

<210> SEQ ID NO 12
<211> LENGTH: 619
<212> TYPE: PRT
<213> ORGANISM: Sphingobacterium sp.

<400> SEQUENCE: 12

Met Lys Asn Thr Ile Ser Cys Leu Thr Leu Ala Leu Leu Ser Ala Ser
1               5                   10                  15

Gln Leu His Ala Gln Thr Ala Asp Ser Ala Tyr Val Arg Asp His
            20                  25                  30

Tyr Glu Lys Thr Glu Val Ala Ile Pro Met Arg Asp Gly Lys Lys Leu
            35                  40                  45

Phe Thr Ala Ile Tyr Ser Pro Lys Asp Lys Ser Lys Lys Tyr Pro Val
        50                  55                  60

Leu Leu Asn Arg Thr Pro Tyr Thr Val Ser Pro Tyr Gly Gln Asn Glu
65                  70                  75                  80
```

-continued

```
Tyr Lys Lys Ser Leu Gly Asn Phe Pro Gln Met Met Arg Glu Gly Tyr
                85                  90                  95
Ile Phe Val Tyr Gln Asp Val Arg Gly Lys Trp Met Ser Glu Gly Asp
            100                 105                 110
Phe Glu Asp Ile Arg Pro Thr Thr Tyr Ser Lys Asp Lys Lys Ala Ile
        115                 120                 125
Asp Glu Ser Thr Asp Thr Tyr Asp Ala Leu Glu Trp Leu Gln Lys Asn
    130                 135                 140
Leu Lys Asn Tyr Asn Gly Lys Ala Gly Leu Tyr Gly Ile Ser Tyr Pro
145                 150                 155                 160
Gly Phe Tyr Ser Thr Val Gly Leu Val Lys Thr His Pro Ser Leu Lys
                165                 170                 175
Ala Val Ser Pro Gln Ala Pro Val Thr Asp Trp Tyr Ile Gly Asp Asp
            180                 185                 190
Phe His His Asn Gly Val Leu Phe Leu Gln Asp Ala Phe Thr Phe Met
        195                 200                 205
Ser Thr Phe Gly Val Pro Arg Pro Lys Pro Ile Thr Pro Asp Gln Phe
    210                 215                 220
Lys Gly Lys Ile Gln Ile Lys Glu Ala Asp Lys Tyr Asn Phe Phe Ala
225                 230                 235                 240
Glu Ala Gly Thr Ala Arg Glu Leu Lys Glu Lys Tyr Phe Gly Asp Ser
                245                 250                 255
Val Gln Phe Trp Asn Asp Leu Phe Lys His Pro Asp Tyr Asp Asp Phe
            260                 265                 270
Trp Lys Ser Arg Val Ile Thr Asn Ser Leu Gln Glu Val Lys Pro Ala
        275                 280                 285
Val Met Val Val Gly Gly Phe Phe Asp Ala Glu Asp Ala Tyr Gly Thr
    290                 295                 300
Phe Lys Thr Tyr Gln Ser Ile Glu Asp Lys Ser Lys Lys Asn Asn Ser
305                 310                 315                 320
Ile Leu Val Ala Gly Pro Trp Tyr His Gly Gly Trp Val Arg Ala Glu
                325                 330                 335
Gly Asn Tyr Leu Gly Asp Ile Gln Phe Glu Lys Lys Thr Ser Ile Thr
            340                 345                 350
Tyr Gln Glu Gln Phe Glu Gln Pro Phe Phe Lys Tyr Tyr Leu Lys Asp
        355                 360                 365
Glu Gly Asn Phe Ala Pro Ser Glu Ala Asn Ile Phe Val Ser Gly Ser
    370                 375                 380
Asn Glu Trp Lys His Phe Glu Gln Trp Pro Pro Lys Asn Val Glu Thr
385                 390                 395                 400
Lys Lys Leu Tyr Phe Gln Pro Gly Lys Leu Gly Phe Asp Lys Val
                405                 410                 415
Gln Arg Thr Asp Ser Trp Asp Glu Tyr Val Thr Asp Pro Asn Lys Pro
            420                 425                 430
Val Pro His Gln Gly Gly Val Ile Gln Asn Arg Thr Arg Glu Tyr Met
        435                 440                 445
Val Asp Asp Gln Arg Phe Ala Ala Ser Arg Pro Asp Val Met Val Tyr
    450                 455                 460
Gln Thr Glu Pro Leu Thr Glu Asp Leu Thr Ile Val Gly Pro Ile Lys
465                 470                 475                 480
Asn Phe Leu Lys Val Ser Ser Thr Gly Thr Asp Ala Asp Tyr Val Val
                485                 490                 495
Lys Leu Ile Asp Val Tyr Pro Asn Asp Ala Ala Ser Tyr Gln Gly Lys
```

```
                    500             505                 510
Thr Met Ala Gly Tyr Gln Met Met Val Arg Gly Glu Ile Met Ala Gly
            515                 520                 525

Lys Tyr Arg Asn Gly Phe Asp Lys Ala Gln Ala Leu Thr Pro Gly Met
        530                 535                 540

Val Glu Lys Val Asn Phe Glu Met Pro Asp Val Ala His Thr Phe Lys
545                 550                 555                 560

Lys Gly His Arg Ile Met Val Gln Val Gln Asn Ser Trp Phe Pro Leu
                565                 570                 575

Ala Glu Arg Asn Pro Gln Val Phe Leu Ala Pro Tyr Thr Ala Thr Lys
            580                 585                 590

Ala Asp Phe Arg Lys Ala Thr Gln Arg Ile Phe His Asp Val Asn Asn
        595                 600                 605

Ala Thr Tyr Ile Glu Phe Ser Val Leu Lys Asp
            610                 615

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
gggaattcca tatgaaaaat acaatttcgt                                    30

<210> SEQ ID NO 14
<211> LENGTH: 29
<212> TYPE: DNA
<213> ORGANISM: Artificial Sequence
<220> FEATURE:
<223> OTHER INFORMATION: Synthetic DNA

<400> SEQUENCE: 14
gctctagact aatctttgag gacagaaaa                                     29

<210> SEQ ID NO 15
<211> LENGTH: 17
<212> TYPE: DNA
<213> ORGANISM: Artificial Sequence
<220> FEATURE:
<223> OTHER INFORMATION: Synthetic DNA

<400> SEQUENCE: 15
gaygayttyc aycayaa                                                  17

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t

<400> SEQUENCE: 16
tgrtcrtcna ccatrtaytc                                               20

<210> SEQ ID NO 17
<211> LENGTH: 1974
<212> TYPE: DNA
<213> ORGANISM: Pedobacter heparinus
```

```
<220> FEATURE:
<221> NAME/KEY: CDS
<222> LOCATION: (61)..(1935)
<223> OTHER INFORMATION:

<400> SEQUENCE: 17
aaacctatcc cgtattcagc aatcaattcc atatatttat ccttaaaaaa accttcctct      60 atg act cct ttc aaa tcg ttt tcc ttc att ttt ctc ttt att ttt acc     108
Met Thr Pro Phe Lys Ser Phe Ser Phe Ile Phe Leu Phe Ile Phe Thr
1               5                   10                  15 agt ctt tct gct tct gca caa cag tcc gac tct gct tat ata cgt cag     156
Ser Leu Ser Ala Ser Ala Gln Gln Ser Asp Ser Ala Tyr Ile Arg Gln
            20                  25                  30 aac tat acc aaa ata gaa agg ctg atc cct atg cgg gat ggc att aag     204
Asn Tyr Thr Lys Ile Glu Arg Leu Ile Pro Met Arg Asp Gly Ile Lys
        35                  40                  45 cta ttt aca gcc att tac atc ccc aaa gac aaa agc aag aag tat cct     252
Leu Phe Thr Ala Ile Tyr Ile Pro Lys Asp Lys Ser Lys Lys Tyr Pro
    50                  55                  60 ttt atg ctc aac cgt act cct tat acc gtt tcg cct tat ggc gaa aac     300
Phe Met Leu Asn Arg Thr Pro Tyr Thr Val Ser Pro Tyr Gly Glu Asn
65                  70                  75                  80 aat tat aaa aca agc ctt ggc ccc tct ccg ctc ttt ata aaa gaa ggc     348
Asn Tyr Lys Thr Ser Leu Gly Pro Ser Pro Leu Phe Ile Lys Glu Gly
                85                  90                  95 ttt atc ttt gtt tat cag gat gta agg ggc aaa tgg atg agt gag gga     396
Phe Ile Phe Val Tyr Gln Asp Val Arg Gly Lys Trp Met Ser Glu Gly
            100                 105                 110 aaa ttt gaa gac gta agg ccg caa ata gcc agc aag aaa cgc aaa acg     444
Lys Phe Glu Asp Val Arg Pro Gln Ile Ala Ser Lys Lys Arg Lys Thr
        115                 120                 125 gat att gat gaa agc tcc gat act tat gat acg atc gac tgg ctg atc     492
Asp Ile Asp Glu Ser Ser Asp Thr Tyr Asp Thr Ile Asp Trp Leu Ile
130                 135                 140 agg aac att cct gga aac aac cgt aaa acc ggt att tac ggt atc tca     540
Arg Asn Ile Pro Gly Asn Asn Arg Lys Thr Gly Ile Tyr Gly Ile Ser
145                 150                 155                 160 tac cca ggc ttt tat gct act gct gcc cta cca gat gcg cat cca tct     588
Tyr Pro Gly Phe Tyr Ala Thr Ala Ala Leu Pro Asp Ala His Pro Ser
                165                 170                 175 tta aag gca gta tcg ccc cag gct ccg gtt acc gac tgg ttt ata ggc     636
Leu Lys Ala Val Ser Pro Gln Ala Pro Val Thr Asp Trp Phe Ile Gly
            180                 185                 190 gat gat ttt cat cac aat ggc acc ttg ttc ctt gca gat atc ttt agc     684
Asp Asp Phe His His Asn Gly Thr Leu Phe Leu Ala Asp Ile Phe Ser
        195                 200                 205 ttc tat tat acc ttc ggg gta ccg cga cct caa cca att acg ccc gac     732
Phe Tyr Tyr Thr Phe Gly Val Pro Arg Pro Gln Pro Ile Thr Pro Asp
    210                 215                 220 aaa cgt cca aaa ccc ttt gat ttc ccg gtt aaa gac aac tac cgt ttt     780
Lys Arg Pro Lys Pro Phe Asp Phe Pro Val Lys Asp Asn Tyr Arg Phe
225                 230                 235                 240 ttt ctt gaa ctg ggc ccc tta aaa aac atc acc aaa aaa tat tat ggc     828
Phe Leu Glu Leu Gly Pro Leu Lys Asn Ile Thr Lys Lys Tyr Tyr Gly
                245                 250                 255 gat acc ata cga ttc tgg aat gat atc aat gcg cat acc aat tat gat     876
Asp Thr Ile Arg Phe Trp Asn Asp Ile Asn Ala His Thr Asn Tyr Asp
            260                 265                 270 gcc ttc tgg aaa gcc cgt aac att acg ccg cat tta att ggt gta aaa     924
Ala Phe Trp Lys Ala Arg Asn Ile Thr Pro His Leu Ile Gly Val Lys
        275                 280                 285
```

| | | |
|---|---|---|
| cct gca gtt ttg gta gtt ggc ggc ttc ttt gat gca gaa gac ctt tac<br>Pro Ala Val Leu Val Val Gly Gly Phe Phe Asp Ala Glu Asp Leu Tyr<br>290                               295                                300 | | 972 |
| ggt acg ctt aaa acc tat cag gcc atc gaa aaa caa aat cca tcc tca<br>Gly Thr Leu Lys Thr Tyr Gln Ala Ile Glu Lys Gln Asn Pro Ser Ser<br>305                               310                                315             320 | | 1020 |
| aaa aac aac ctc gtt atg ggc ccc tgg tac cat ggt ggc tgg gca aga<br>Lys Asn Asn Leu Val Met Gly Pro Trp Tyr His Gly Gly Trp Ala Arg<br>                         325                                330                             335 | | 1068 |
| agt acg gga agc agt ttc ggg gat att aat ttc gga cag cca acc agt<br>Ser Thr Gly Ser Ser Phe Gly Asp Ile Asn Phe Gly Gln Pro Thr Ser<br>                     340                                345                             350 | | 1116 |
| act tca tac cag caa aat gtt gag ttc cct ttc ttt atg caa tac ctc<br>Thr Ser Tyr Gln Gln Asn Val Glu Phe Pro Phe Phe Met Gln Tyr Leu<br>355                               360                                365 | | 1164 |
| aaa gag gca ccg gat gca aaa att gca gag gca acc att ttt atc act<br>Lys Glu Ala Pro Asp Ala Lys Ile Ala Glu Ala Thr Ile Phe Ile Thr<br>                     370                                375                             380 | | 1212 |
| ggc agc aat gaa tgg aag aaa ttt agc tcc tgg cca cct cag gat aca<br>Gly Ser Asn Glu Trp Lys Lys Phe Ser Ser Trp Pro Pro Gln Asp Thr<br>385                               390                                395             400 | | 1260 |
| gaa gaa aga aca tta tac ctg cag ccc aat ggc aaa ctg agc ttt gag<br>Glu Glu Arg Thr Leu Tyr Leu Gln Pro Asn Gly Lys Leu Ser Phe Glu<br>                     405                                410                             415 | | 1308 |
| aag gta cag cgg acc gac agc tgg gat gaa tat gta agt gat ccc aat<br>Lys Val Gln Arg Thr Asp Ser Trp Asp Glu Tyr Val Ser Asp Pro Asn<br>                   420                              425                             430 | | 1356 |
| tca cct gtc cct tat cag gat ggc ata caa acc agc aga acc cgg gaa<br>Ser Pro Val Pro Tyr Gln Asp Gly Ile Gln Thr Ser Arg Thr Arg Glu<br>                         435                                440                             445 | | 1404 |
| tat atg atc gat gac cag cgt ttt gcc tcg cgc aga ccg gat gta agg<br>Tyr Met Ile Asp Asp Gln Arg Phe Ala Ser Arg Arg Pro Asp Val Arg<br>450                               455                                460 | | 1452 |
| gta ttc caa aca gag ccc ctc agt tcc gac ctt aca ctt acc ggc ccg<br>Val Phe Gln Thr Glu Pro Leu Ser Ser Asp Leu Thr Leu Thr Gly Pro<br>465                               470                                475             480 | | 1500 |
| gta ttg gcc aaa ctg gtg gta tca acc aca ggt acg gat gca gat tat<br>Val Leu Ala Lys Leu Val Val Ser Thr Thr Gly Thr Asp Ala Asp Tyr<br>                         485                                490                             495 | | 1548 |
| gtg gta aaa ctg ata gat gta tat ccg gaa gat aca cca aat cct gta<br>Val Val Lys Leu Ile Asp Val Tyr Pro Glu Asp Thr Pro Asn Pro Val<br>500                               505                                510 | | 1596 |
| cct aac cct aaa aac ctg atc atg ggt ggt tac cag atg ctg gta cgc<br>Pro Asn Pro Lys Asn Leu Ile Met Gly Gly Tyr Gln Met Leu Val Arg<br>                     515                                520                             525 | | 1644 |
| ggc gag atc atg cgt gga aaa tac cgt aat agc ttt gaa aaa ccc gag<br>Gly Glu Ile Met Arg Gly Lys Tyr Arg Asn Ser Phe Glu Lys Pro Glu<br>                     530                                535                             540 | | 1692 |
| cct ttt gtt cct gga aca att aca aaa gta aac tat gcc ctt ccg gat<br>Pro Phe Val Pro Gly Thr Ile Thr Lys Val Asn Tyr Ala Leu Pro Asp<br>545                               550                                555             560 | | 1740 |
| gta gcc cat acc ttt aaa aaa ggc cac cgc atc atg atc cag gtc cag<br>Val Ala His Thr Phe Lys Lys Gly His Arg Ile Met Ile Gln Val Gln<br>                         565                                570                             575 | | 1788 |
| aat tca tgg ttt ccc ctg gcc gac cgg aat cca cag cag ttt atg gac<br>Asn Ser Trp Phe Pro Leu Ala Asp Arg Asn Pro Gln Gln Phe Met Asp<br>                   580                                585                             590 | | 1836 |
| att tac cag gcc gaa cct ggc gat ttc aga aaa gct acg cat agg atc<br>Ile Tyr Gln Ala Glu Pro Gly Asp Phe Arg Lys Ala Thr His Arg Ile<br>                         595                                600                             605 | | 1884 |

-continued

```
ttc cac gat gta cac aat gca tct gca att acg gta aac gta ctg aaa      1932
Phe His Asp Val His Asn Ala Ser Ala Ile Thr Val Asn Val Leu Lys
    610             615                 620 cct taaaacggat gaaaccagta tattgtgcca tccttactt                       1974
Pro
625

<210> SEQ ID NO 18
<211> LENGTH: 625
<212> TYPE: PRT
<213> ORGANISM: Pedobacter heparinus

<400> SEQUENCE: 18

Met Thr Pro Phe Lys Ser Phe Ser Phe Ile Phe Leu Phe Ile Phe Thr
1               5                   10                  15

Ser Leu Ser Ala Ser Ala Gln Gln Ser Asp Ser Ala Tyr Ile Arg Gln
                20                  25                  30

Asn Tyr Thr Lys Ile Glu Arg Leu Ile Pro Met Arg Asp Gly Ile Lys
            35                  40                  45

Leu Phe Thr Ala Ile Tyr Ile Pro Lys Asp Lys Ser Lys Lys Tyr Pro
50                  55                  60

Phe Met Leu Asn Arg Thr Pro Tyr Thr Val Ser Pro Tyr Gly Glu Asn
65                  70                  75                  80

Asn Tyr Lys Thr Ser Leu Gly Pro Ser Pro Leu Phe Ile Lys Glu Gly
                85                  90                  95

Phe Ile Phe Val Tyr Gln Asp Val Arg Gly Lys Trp Met Ser Glu Gly
            100                 105                 110

Lys Phe Glu Asp Val Arg Pro Gln Ile Ala Ser Lys Lys Arg Lys Thr
        115                 120                 125

Asp Ile Asp Glu Ser Ser Asp Thr Tyr Asp Thr Ile Asp Trp Leu Ile
130                 135                 140

Arg Asn Ile Pro Gly Asn Asn Arg Lys Thr Gly Ile Tyr Gly Ile Ser
145                 150                 155                 160

Tyr Pro Gly Phe Tyr Ala Thr Ala Ala Leu Pro Asp Ala His Pro Ser
                165                 170                 175

Leu Lys Ala Val Ser Pro Gln Ala Pro Val Thr Asp Trp Phe Ile Gly
            180                 185                 190

Asp Asp Phe His His Asn Gly Thr Leu Phe Leu Ala Asp Ile Phe Ser
        195                 200                 205

Phe Tyr Tyr Thr Phe Gly Val Pro Arg Pro Gln Pro Ile Thr Pro Asp
210                 215                 220

Lys Arg Pro Lys Pro Phe Asp Phe Pro Val Lys Asp Asn Tyr Arg Phe
225                 230                 235                 240

Phe Leu Glu Leu Gly Pro Leu Lys Asn Ile Thr Lys Lys Tyr Tyr Gly
                245                 250                 255

Asp Thr Ile Arg Phe Trp Asn Asp Ile Asn Ala His Thr Asn Tyr Asp
            260                 265                 270

Ala Phe Trp Lys Ala Arg Asn Ile Thr Pro His Leu Ile Gly Val Lys
        275                 280                 285

Pro Ala Val Leu Val Val Gly Phe Phe Asp Ala Glu Asp Leu Tyr
290                 295                 300

Gly Thr Leu Lys Thr Tyr Gln Ala Ile Glu Lys Gln Asn Pro Ser Ser
305                 310                 315                 320

Lys Asn Asn Leu Val Met Gly Pro Trp Tyr His Gly Gly Trp Ala Arg
                325                 330                 335
```

Ser Thr Gly Ser Ser Phe Gly Asp Ile Asn Phe Gly Gln Pro Thr Ser
            340                 345                 350

Thr Ser Tyr Gln Gln Asn Val Glu Phe Pro Phe Met Gln Tyr Leu
        355                 360                 365

Lys Glu Ala Pro Asp Ala Lys Ile Ala Glu Ala Thr Ile Phe Ile Thr
370                 375                 380

Gly Ser Asn Glu Trp Lys Lys Phe Ser Ser Trp Pro Pro Gln Asp Thr
385                 390                 395                 400

Glu Glu Arg Thr Leu Tyr Leu Gln Pro Asn Gly Lys Leu Ser Phe Glu
                405                 410                 415

Lys Val Gln Arg Thr Asp Ser Trp Asp Glu Tyr Val Ser Asp Pro Asn
            420                 425                 430

Ser Pro Val Pro Tyr Gln Asp Gly Ile Gln Thr Ser Arg Thr Arg Glu
        435                 440                 445

Tyr Met Ile Asp Asp Gln Arg Phe Ala Ser Arg Arg Pro Asp Val Arg
450                 455                 460

Val Phe Gln Thr Glu Pro Leu Ser Ser Asp Leu Thr Leu Thr Gly Pro
465                 470                 475                 480

Val Leu Ala Lys Leu Val Val Ser Thr Thr Gly Thr Asp Ala Asp Tyr
                485                 490                 495

Val Val Lys Leu Ile Asp Val Tyr Pro Glu Asp Thr Pro Asn Pro Val
            500                 505                 510

Pro Asn Pro Lys Asn Leu Ile Met Gly Gly Tyr Gln Met Leu Val Arg
        515                 520                 525

Gly Glu Ile Met Arg Gly Lys Tyr Arg Asn Ser Phe Glu Lys Pro Glu
530                 535                 540

Pro Phe Val Pro Gly Thr Ile Thr Lys Val Asn Tyr Ala Leu Pro Asp
545                 550                 555                 560

Val Ala His Thr Phe Lys Lys Gly His Arg Ile Met Ile Gln Val Gln
                565                 570                 575

Asn Ser Trp Phe Pro Leu Ala Asp Arg Asn Pro Gln Gln Phe Met Asp
        580                 585                 590

Ile Tyr Gln Ala Glu Pro Gly Asp Phe Arg Lys Ala Thr His Arg Ile
    595                 600                 605

Phe His Asp Val His Asn Ala Ser Ala Ile Thr Val Asn Val Leu Lys
    610                 615                 620

Pro
625

<210> SEQ ID NO 19
<211> LENGTH: 38
<212> TYPE: DNA
<213> ORGANISM: Artificial Sequence
<220> FEATURE:
<223> OTHER INFORMATION: Synthetic DNA

<400> SEQUENCE: 19
gggaattcca tatgactcct ttcaaatcgt tctccttc                              38

<210> SEQ ID NO 20
<211> LENGTH: 30
<212> TYPE: DNA
<213> ORGANISM: Artificial Sequence
<220> FEATURE:
<223> OTHER INFORMATION: Synthetic DNA

<400> SEQUENCE: 20
cccaagcttt taaggtttca gtacgtttac                                       30

<210> SEQ ID NO 21
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a, c, g, or t

<400> SEQUENCE: 21
athttygtnt aycarga                                                     17

<210> SEQ ID NO 22
<211> LENGTH: 2018
<212> TYPE: DNA
<213> ORGANISM: Taxeobacter gelupurpurascens
<220> FEATURE:
<221> NAME/KEY: CDS
<222> LOCATION: (61)..(1995)
<223> OTHER INFORMATION:

<400> SEQUENCE: 22
ctgaatgtct gctgacgaat tggaactaca ttaggctcgt tcttcaccta cccttccact        60 atg ccc tac tct ttc ccg aaa gtt gcc gcc ctg agt ggc cta ctg gtg        108
Met Pro Tyr Ser Phe Pro Lys Val Ala Ala Leu Ser Gly Leu Leu Val
1               5                   10                  15 gcc ggt tta tcc ggt gcc cac gcc caa act cct gtt acc tat ccg ctg        156
Ala Gly Leu Ser Gly Ala His Ala Gln Thr Pro Val Thr Tyr Pro Leu
            20                  25                  30 gct tct gag gct gaa aaa gcg cag ctg gcg gtg gta cta gcc gat acg        204
Ala Ser Glu Ala Glu Lys Ala Gln Leu Ala Val Val Leu Ala Asp Thr
        35                  40                  45 gct tac atc aag gag cgc tat acc aaa aca gaa tat cag att ccg atg        252
Ala Tyr Ile Lys Glu Arg Tyr Thr Lys Thr Glu Tyr Gln Ile Pro Met
    50                  55                  60 cgc gat ggg gtg aag ttg tac acc att gtg tac gcg ccc aac gat gcc        300
Arg Asp Gly Val Lys Leu Tyr Thr Ile Val Tyr Ala Pro Asn Asp Ala
65                  70                  75                  80 aac aag gta aag tac cct att ctg ctc aac cgt acc cct tac gct att        348
Asn Lys Val Lys Tyr Pro Ile Leu Leu Asn Arg Thr Pro Tyr Ala Ile
                85                  90                  95 ggc ccc tac ggc ccc ggc aaa tac aag ctc aac ctg ggc ccc agc agc        396
Gly Pro Tyr Gly Pro Gly Lys Tyr Lys Leu Asn Leu Gly Pro Ser Ser
            100                 105                 110 acg atg atg cat gag gga tac atc ttc gcc tac cag gat gtg cgt ggg        444
Thr Met Met His Glu Gly Tyr Ile Phe Ala Tyr Gln Asp Val Arg Gly
        115                 120                 125 cga tat atg tcg gaa gga gag ttt gtg gat gtg cgc ccc gaa aag gac        492
Arg Tyr Met Ser Glu Gly Glu Phe Val Asp Val Arg Pro Glu Lys Asp
    130                 135                 140 atg cac aaa ggc aag aac gac atc gat gaa ggc acc gac acc tac gat        540
Met His Lys Gly Lys Asn Asp Ile Asp Glu Gly Thr Asp Thr Tyr Asp
145                 150                 155                 160 acc att gag tgg ctt ctg aag cac ggg ccc aag aat aac ggc cgc gta        588
Thr Ile Glu Trp Leu Leu Lys His Gly Pro Lys Asn Asn Gly Arg Val
                165                 170                 175 ggc cag tgg ggc atc tcc tac ccc ggc tac tat acc gct act ggc cta        636
Gly Gln Trp Gly Ile Ser Tyr Pro Gly Tyr Tyr Thr Ala Thr Gly Leu
            180                 185                 190 ctg agc cgc cac aag gcc cta aag gca tcc tca ccg cag gcc cct att        684

```
Leu Ser Arg His Lys Ala Leu Lys Ala Ser Ser Pro Gln Ala Pro Ile
    195                 200                 205 gcc gac tgg ttc tgg gac gat ttt cac cac aac ggc gcg ttc ttc ctg      732
Ala Asp Trp Phe Trp Asp Asp Phe His His Asn Gly Ala Phe Phe Leu
210                 215                 220 ccg cac gct ttc aac ttc ctg gcc tcc ttt ggg ctg gcc cgc ccc cag      780
Pro His Ala Phe Asn Phe Leu Ala Ser Phe Gly Leu Ala Arg Pro Gln
225                 230                 235                 240 ccc acg cct acc ggc aac ccc ggc ttc aag cac ggc acc ccc gat ggc      828
Pro Thr Pro Thr Gly Asn Pro Gly Phe Lys His Gly Thr Pro Asp Gly
                245                 250                 255 tac gat ttt ttc ctg aag atg ggt ccg ctg aaa aac gct gat gcc aac      876
Tyr Asp Phe Phe Leu Lys Met Gly Pro Leu Lys Asn Ala Asp Ala Asn
            260                 265                 270 tac tac aaa ggc aaa gtg gcc ttc tgg aac gaa atg gcc agc cac ccc      924
Tyr Tyr Lys Gly Lys Val Ala Phe Trp Asn Glu Met Ala Ser His Pro
        275                 280                 285 aac tac gac gaa ttc tgg cag gcc cgt aac cta cgc ccc cac ctc aag      972
Asn Tyr Asp Glu Phe Trp Gln Ala Arg Asn Leu Arg Pro His Leu Lys
290                 295                 300 aac ctc aac aaa ggc acc gcg gtg ctc acg gtt ggt ggc ttc aat gat     1020
Asn Leu Asn Lys Gly Thr Ala Val Leu Thr Val Gly Gly Phe Asn Asp
305                 310                 315                 320 gcc gag gac ctg ttt ggc gcc ctg aaa acc tac gaa agc atc gag aag     1068
Ala Glu Asp Leu Phe Gly Ala Leu Lys Thr Tyr Glu Ser Ile Glu Lys
                325                 330                 335 caa aac ccc ggc atg cgc aac ggc ctc gtg atg ggg ccg tgg gta cac     1116
Gln Asn Pro Gly Met Arg Asn Gly Leu Val Met Gly Pro Trp Val His
            340                 345                 350 ggt ggc tgg gcc cgc ggc act ggc gaa atg gta ggc aat gtg gcc tac     1164
Gly Gly Trp Ala Arg Gly Thr Gly Glu Met Val Gly Asn Val Ala Tyr
        355                 360                 365 ggc gag tcg ccg tcg ttg tat tac cag aag cag att gaa gcg ccg ttc     1212
Gly Glu Ser Pro Ser Leu Tyr Tyr Gln Lys Gln Ile Glu Ala Pro Phe
    370                 375                 380 ttc aaa tca tat ctg aag gat ggc aaa cct gcc gct acc ccc gag gct     1260
Phe Lys Ser Tyr Leu Lys Asp Gly Lys Pro Ala Ala Thr Pro Glu Ala
385                 390                 395                 400 acc atc ttt gaa agc ggc acc aac cgc tgg cgc agc ttc gaa acc tgg     1308
Thr Ile Phe Glu Ser Gly Thr Asn Arg Trp Arg Ser Phe Glu Thr Trp
                405                 410                 415 ccg ccc aaa gaa gcc aaa gag cgc act ttg tac ttt cag tcg gcc ggg     1356
Pro Pro Lys Glu Ala Lys Glu Arg Thr Leu Tyr Phe Gln Ser Ala Gly
            420                 425                 430 aaa atc ggc ttc gag aag cct gcc agt ggc cta gag tac gac cag ttc     1404
Lys Ile Gly Phe Glu Lys Pro Ala Ser Gly Leu Glu Tyr Asp Gln Phe
        435                 440                 445 ctc agc gac ccg gct cac cca gtg cct ttc acc gaa gct acg gct acg     1452
Leu Ser Asp Pro Ala His Pro Val Pro Phe Thr Glu Ala Thr Ala Thr
    450                 455                 460 ggc atg acc cgc gag tac atg acc gac gac cag cgc ttc gcc agc cgc     1500
Gly Met Thr Arg Glu Tyr Met Thr Asp Asp Gln Arg Phe Ala Ser Arg
465                 470                 475                 480 cgc ccc gac gtg ctg acc tac cag acc gaa gcg ctt acc gag gac atg     1548
Arg Pro Asp Val Leu Thr Tyr Gln Thr Glu Ala Leu Thr Glu Asp Met
                485                 490                 495 acg ctg gct ggc cct atc gag gcg ctg ttg cag gta gcc acc acc ggc     1596
Thr Leu Ala Gly Pro Ile Glu Ala Leu Leu Gln Val Ala Thr Thr Gly
            500                 505                 510 acc gat gcc gac tgg gta gtg aag att att gat gtg tac ccc gac gat     1644
```

```
Thr Asp Ala Asp Trp Val Val Lys Ile Ile Asp Val Tyr Pro Asp Asp
            515                 520                 525 acg ccc aac aac ccc agc acg aac ccc gcc gtg aaa ctg ggc ggc tac       1692
Thr Pro Asn Asn Pro Ser Thr Asn Pro Ala Val Lys Leu Gly Gly Tyr
530                 535                 540 cag cag atg gtt cgc tcc gag gtg atg cgc ggt cgt ttc cgc aac agc       1740
Gln Gln Met Val Arg Ser Glu Val Met Arg Gly Arg Phe Arg Asn Ser
545                 550                 555                 560 ttc tcc aag ccc gaa gcc ttt gta ccg gaa cag gta acg gcc gtg ccc       1788
Phe Ser Lys Pro Glu Ala Phe Val Pro Glu Gln Val Thr Ala Val Pro
                565                 570                 575 ttc acg gtg cag gac ctg tgc cac acc ttc cgg aaa gga cac cgc ctg       1836
Phe Thr Val Gln Asp Leu Cys His Thr Phe Arg Lys Gly His Arg Leu
            580                 585                 590 atg gtg cag gtg caa agc agc tgg ttc ccg att gtt gac cgc aac ccg       1884
Met Val Gln Val Gln Ser Ser Trp Phe Pro Ile Val Asp Arg Asn Pro
        595                 600                 605 cag acc ttc gta ccc aat att ttc gag gcc gat gag aag gat ttc cag       1932
Gln Thr Phe Val Pro Asn Ile Phe Glu Ala Asp Glu Lys Asp Phe Gln
    610                 615                 620 gcc gcc acg cat cgg ctg tac cat tcg ccg gcg cat agc tcg cag ctc       1980
Ala Ala Thr His Arg Leu Tyr His Ser Pro Ala His Ser Ser Gln Leu
625                 630                 635                 640 acg ttg cgc gtt ctg taggccactc taaacaggct cgg                         2018
Thr Leu Arg Val Leu
                645

<210> SEQ ID NO 23
<211> LENGTH: 645
<212> TYPE: PRT
<213> ORGANISM: Taxeobacter gelupurpurascens

<400> SEQUENCE: 23

Met Pro Tyr Ser Phe Pro Lys Val Ala Ala Leu Ser Gly Leu Leu Val
1               5                   10                  15

Ala Gly Leu Ser Gly Ala His Ala Gln Thr Pro Val Thr Tyr Pro Leu
            20                  25                  30

Ala Ser Glu Ala Glu Lys Ala Gln Leu Ala Val Val Leu Ala Asp Thr
        35                  40                  45

Ala Tyr Ile Lys Glu Arg Tyr Thr Lys Thr Glu Tyr Gln Ile Pro Met
    50                  55                  60

Arg Asp Gly Val Lys Leu Tyr Thr Ile Val Tyr Ala Pro Asn Asp Ala
65                  70                  75                  80

Asn Lys Val Lys Tyr Pro Ile Leu Leu Asn Arg Thr Pro Tyr Ala Ile
                85                  90                  95

Gly Pro Tyr Gly Pro Gly Lys Tyr Lys Leu Asn Leu Gly Pro Ser Ser
            100                 105                 110

Thr Met Met His Glu Gly Tyr Ile Phe Ala Tyr Gln Asp Val Arg Gly
        115                 120                 125

Arg Tyr Met Ser Glu Gly Glu Phe Val Asp Val Arg Pro Glu Lys Asp
    130                 135                 140

Met His Lys Gly Lys Asn Asp Ile Asp Glu Gly Thr Asp Thr Tyr Asp
145                 150                 155                 160

Thr Ile Glu Trp Leu Leu Lys His Gly Pro Lys Asn Asn Gly Arg Val
                165                 170                 175

Gly Gln Trp Gly Ile Ser Tyr Pro Gly Tyr Tyr Thr Ala Thr Gly Leu
            180                 185                 190

Leu Ser Arg His Lys Ala Leu Lys Ala Ser Ser Pro Gln Ala Pro Ile
```

-continued

```
                195                 200                 205
Ala Asp Trp Phe Trp Asp Asp Phe His His Asn Gly Ala Phe Phe Leu
210                 215                 220
Pro His Ala Phe Asn Phe Leu Ala Ser Phe Gly Leu Ala Arg Pro Gln
225                 230                 235                 240
Pro Thr Pro Thr Gly Asn Pro Gly Phe Lys His Gly Thr Pro Asp Gly
            245                 250                 255
Tyr Asp Phe Phe Leu Lys Met Gly Pro Leu Lys Asn Ala Asp Ala Asn
            260                 265                 270
Tyr Tyr Lys Gly Lys Val Ala Phe Trp Asn Glu Met Ala Ser His Pro
            275                 280                 285
Asn Tyr Asp Glu Phe Trp Gln Ala Arg Asn Leu Arg Pro His Leu Lys
290                 295                 300
Asn Leu Asn Lys Gly Thr Ala Val Leu Thr Val Gly Gly Phe Asn Asp
305                 310                 315                 320
Ala Glu Asp Leu Phe Gly Ala Leu Lys Thr Tyr Glu Ser Ile Glu Lys
            325                 330                 335
Gln Asn Pro Gly Met Arg Asn Gly Leu Val Met Gly Pro Trp Val His
            340                 345                 350
Gly Gly Trp Ala Arg Gly Thr Gly Glu Met Val Gly Asn Val Ala Tyr
            355                 360                 365
Gly Glu Ser Pro Ser Leu Tyr Tyr Gln Lys Gln Ile Glu Ala Pro Phe
            370                 375                 380
Phe Lys Ser Tyr Leu Lys Asp Gly Lys Pro Ala Ala Thr Pro Glu Ala
385                 390                 395                 400
Thr Ile Phe Glu Ser Gly Thr Asn Arg Trp Arg Ser Phe Glu Thr Trp
            405                 410                 415
Pro Pro Lys Glu Ala Lys Glu Arg Thr Leu Tyr Phe Gln Ser Ala Gly
            420                 425                 430
Lys Ile Gly Phe Glu Lys Pro Ala Ser Gly Leu Glu Tyr Asp Gln Phe
            435                 440                 445
Leu Ser Asp Pro Ala His Pro Val Pro Phe Thr Glu Ala Thr Ala Thr
450                 455                 460
Gly Met Thr Arg Glu Tyr Met Thr Asp Asp Gln Arg Phe Ala Ser Arg
465                 470                 475                 480
Arg Pro Asp Val Leu Thr Tyr Gln Thr Glu Ala Leu Thr Glu Asp Met
            485                 490                 495
Thr Leu Ala Gly Pro Ile Glu Ala Leu Leu Gln Val Ala Thr Thr Gly
            500                 505                 510
Thr Asp Ala Asp Trp Val Val Lys Ile Ile Asp Val Tyr Pro Asp Asp
            515                 520                 525
Thr Pro Asn Asn Pro Ser Thr Asn Pro Ala Val Lys Leu Gly Gly Tyr
530                 535                 540
Gln Gln Met Val Arg Ser Glu Val Met Arg Gly Arg Phe Arg Asn Ser
545                 550                 555                 560
Phe Ser Lys Pro Glu Ala Phe Val Pro Glu Gln Val Thr Ala Val Pro
            565                 570                 575
Phe Thr Val Gln Asp Leu Cys His Thr Phe Arg Lys Gly His Arg Leu
            580                 585                 590
Met Val Gln Val Gln Ser Ser Trp Phe Pro Ile Val Asp Arg Asn Pro
            595                 600                 605
Gln Thr Phe Val Pro Asn Ile Phe Glu Ala Asp Glu Lys Asp Phe Gln
610                 615                 620
```

```
Ala Ala Thr His Arg Leu Tyr His Ser Pro Ala His Ser Ser Gln Leu
625                 630                 635                 640

Thr Leu Arg Val Leu
            645

<210> SEQ ID NO 24
<211> LENGTH: 1931
<212> TYPE: DNA
<213> ORGANISM: Cyclobacterium marinum
<220> FEATURE:
<221> NAME/KEY: CDS
<222> LOCATION: (29)..(1888)
<223> OTHER INFORMATION:

<400> SEQUENCE: 24
cccaaagcat taacaaaata atttagtc atg aaa cac tgt tac aaa ctt ctg           52
                                Met Lys His Cys Tyr Lys Leu Leu
                                  1               5 gtc ttt tac aca tta ttt ttg atg acc aca aac tgg gct tta tca caa         100
Val Phe Tyr Thr Leu Phe Leu Met Thr Thr Asn Trp Ala Leu Ser Gln
     10                  15                  20 gcc att aat gga tat gat aag gca gcc tat gac att cct atg cga gat         148
Ala Ile Asn Gly Tyr Asp Lys Ala Ala Tyr Asp Ile Pro Met Arg Asp
 25                  30                  35                  40 gga gtt cac ctt cac acc atc gtc tat agc ccc aaa gat tta tcg cag         196
Gly Val His Leu His Thr Ile Val Tyr Ser Pro Lys Asp Leu Ser Gln
                 45                  50                  55 ccc tat cct ata ttg atg caa agg aca cct tac agc gcc ggc cct tat         244
Pro Tyr Pro Ile Leu Met Gln Arg Thr Pro Tyr Ser Ala Gly Pro Tyr
             60                  65                  70 ggt cct gga aat atg aaa aat aag ctt ggc cct tct cag ttt tta atg         292
Gly Pro Gly Asn Met Lys Asn Lys Leu Gly Pro Ser Gln Phe Leu Met
         75                  80                  85 aac gat ggc tat ata ttt gtt tac cag gat gta aga ggg cgg tgg atg         340
Asn Asp Gly Tyr Ile Phe Val Tyr Gln Asp Val Arg Gly Arg Trp Met
     90                  95                 100 tcg gaa gga tcc tat gac aac atg cgc cct acc cta tcc aaa tca gaa         388
Ser Glu Gly Ser Tyr Asp Asn Met Arg Pro Thr Leu Ser Lys Ser Glu
105                 110                 115                 120 aga aat tcc aac caa ata gac gaa agc aca gac acc tat gat acc ata         436
Arg Asn Ser Asn Gln Ile Asp Glu Ser Thr Asp Thr Tyr Asp Thr Ile
                125                 130                 135 gaa tgg ttg ctc gcc aat atc aaa aat cac aat gaa aaa gta ggc cta         484
Glu Trp Leu Leu Ala Asn Ile Lys Asn His Asn Glu Lys Val Gly Leu
            140                 145                 150 tgg gga atc agc tat ccc gga ttt tat agt gct gca gcc ctt cct ttt         532
Trp Gly Ile Ser Tyr Pro Gly Phe Tyr Ser Ala Ala Ala Leu Pro Phe
        155                 160                 165 gcc cat cca aac ctg aaa gcc gtt tcc cct caa gca ccc ata ggg gat         580
Ala His Pro Asn Leu Lys Ala Val Ser Pro Gln Ala Pro Ile Gly Asp
    170                 175                 180 ttt tac ttt gat gat ttt cat cat aac ggt gct tac tta tta agt tat         628
Phe Tyr Phe Asp Asp Phe His His Asn Gly Ala Tyr Leu Leu Ser Tyr
185                 190                 195                 200 tgg ttg gcc act tct gtt ttc ggc tac caa aaa gac ggc cct aca cag         676
Trp Leu Ala Thr Ser Val Phe Gly Tyr Gln Lys Asp Gly Pro Thr Gln
                205                 210                 215 gaa gca tgg tat ggc atg gtg aat ccg gaa aca aat gac ggc tat cag         724
Glu Ala Trp Tyr Gly Met Val Asn Pro Glu Thr Asn Asp Gly Tyr Gln
            220                 225                 230 ttt ttt atg gat atg ggg cca tta aaa aat gcc gat aaa tgg tat ggt         772
Phe Phe Met Asp Met Gly Pro Leu Lys Asn Ala Asp Lys Trp Tyr Gly
```

```
                235                 240                 245
gaa gac aat ttt ttc tgg caa caa ctt aaa aac aat cct gat tac aac         820
Glu Asp Asn Phe Phe Trp Gln Gln Leu Lys Asn Asn Pro Asp Tyr Asn
    250                 255                 260 gct ttc tgg caa aag aga agt att att cct cac tta aaa gaa gtg aag         868
Ala Phe Trp Gln Lys Arg Ser Ile Ile Pro His Leu Lys Glu Val Lys
265                 270                 275                 280 cct gca gtt tta acc gtt ggg ggc tgg ttt gat gca gaa gat ctc tat         916
Pro Ala Val Leu Thr Val Gly Gly Trp Phe Asp Ala Glu Asp Leu Tyr
                285                 290                 295 gga cca ctt aca att tat aaa acc att gaa aaa aat aat cct gag acc         964
Gly Pro Leu Thr Ile Tyr Lys Thr Ile Glu Lys Asn Asn Pro Glu Thr
            300                 305                 310 tac aat acc att gtc atg ggc cct tgg tcc cac gga gat tgg tca agg        1012
Tyr Asn Thr Ile Val Met Gly Pro Trp Ser His Gly Asp Trp Ser Arg
        315                 320                 325 gaa cct gga tca cag gtc att tca aat att tat ttt ggt gat tct atc        1060
Glu Pro Gly Ser Gln Val Ile Ser Asn Ile Tyr Phe Gly Asp Ser Ile
    330                 335                 340 tcc aca tgg tat caa aaa aat ata gaa cgt gtt ttt ttc aat cat ttt        1108
Ser Thr Trp Tyr Gln Lys Asn Ile Glu Arg Val Phe Phe Asn His Phe
345                 350                 355                 360 cta aaa gaa tcc gaa aat agc aat cct gcc ctt cct gaa gcc tac atg        1156
Leu Lys Glu Ser Glu Asn Ser Asn Pro Ala Leu Pro Glu Ala Tyr Met
                365                 370                 375 ttt gat acc gga aaa cat aaa tgg gaa aaa ttt gac gat tgg cct cct        1204
Phe Asp Thr Gly Lys His Lys Trp Glu Lys Phe Asp Asp Trp Pro Pro
            380                 385                 390 aaa gaa agc caa tgg aaa agc ttt tac ttt caa gag aaa gga gag tta        1252
Lys Glu Ser Gln Trp Lys Ser Phe Tyr Phe Gln Glu Lys Gly Glu Leu
        395                 400                 405 act gag gta aca cct gag gga aat agg ttt act acc tat gtc tca gac        1300
Thr Glu Val Thr Pro Glu Gly Asn Arg Phe Thr Thr Tyr Val Ser Asp
    410                 415                 420 ccc tct aat cct gtc ccc tat agt caa gat att aaa cta aac ttc act        1348
Pro Ser Asn Pro Val Pro Tyr Ser Gln Asp Ile Lys Leu Asn Phe Thr
425                 430                 435                 440 ccg aga aaa tac atg gcc gat gac cag cga ttt gca gcc aga aga ccg        1396
Pro Arg Lys Tyr Met Ala Asp Asp Gln Arg Phe Ala Ala Arg Arg Pro
                445                 450                 455 gac gta ctg acc ttt acg agc gaa gta tta agt caa gac atg acg ctt        1444
Asp Val Leu Thr Phe Thr Ser Glu Val Leu Ser Gln Asp Met Thr Leu
            460                 465                 470 gcg ggg gaa gtc atg gca aac tta aaa gtt gcc act tca caa act gat        1492
Ala Gly Glu Val Met Ala Asn Leu Lys Val Ala Thr Ser Gln Thr Asp
        475                 480                 485 gct gat tgg gta gtt aaa atc atc gat ata ttt ccc gga gat cag cca        1540
Ala Asp Trp Val Val Lys Ile Ile Asp Ile Phe Pro Gly Asp Gln Pro
    490                 495                 500 aat cat gcc tat gtt tta gat ggg gtg gac atg ggc aat tac cac cta        1588
Asn His Ala Tyr Val Leu Asp Gly Val Asp Met Gly Asn Tyr His Leu
505                 510                 515                 520 atg gtt cgt tca gag gta att aga ggg agg tat aga gaa agt ttt gag        1636
Met Val Arg Ser Glu Val Ile Arg Gly Arg Tyr Arg Glu Ser Phe Glu
                525                 530                 535 ttt cct aaa ccc ttt gtt cct gat caa atc act gct gtt gat ttc agg        1684
Phe Pro Lys Pro Phe Val Pro Asp Gln Ile Thr Ala Val Asp Phe Arg
            540                 545                 550 tta caa gat ctt ttc cat act ttc aaa aag ggg cat aaa att caa ata        1732
Leu Gln Asp Leu Phe His Thr Phe Lys Lys Gly His Lys Ile Gln Ile
```

```
                555                 560                 565
caa ata caa agt act tgg ttt ccc cta att gat cga aat ccc caa aaa    1780
Gln Ile Gln Ser Thr Trp Phe Pro Leu Ile Asp Arg Asn Pro Gln Lys
    570                 575                 580 tat gta caa aac ata ttt gaa gct gag gaa gcc gat ttt gtc aaa gcc    1828
Tyr Val Gln Asn Ile Phe Glu Ala Glu Glu Ala Asp Phe Val Lys Ala
585                 590                 595                 600 acc cat agg gtt ttt cat aca gaa aag ttt gcc agc aaa att gaa gta    1876
Thr His Arg Val Phe His Thr Glu Lys Phe Ala Ser Lys Ile Glu Val
                605                 610                 615 atg gtt ctt cct tagaattaga atggtttaaa attactattt gtagcagaag ata    1931
Met Val Leu Pro
            620

<210> SEQ ID NO 25
<211> LENGTH: 620
<212> TYPE: PRT
<213> ORGANISM: Cyclobacterium marinum

<400> SEQUENCE: 25

Met Lys His Cys Tyr Lys Leu Leu Val Phe Tyr Thr Leu Phe Leu Met
1               5                   10                  15

Thr Thr Asn Trp Ala Leu Ser Gln Ala Ile Asn Gly Tyr Asp Lys Ala
            20                  25                  30

Ala Tyr Asp Ile Pro Met Arg Asp Gly Val His Leu Thr Ile Val
        35                  40                  45

Tyr Ser Pro Lys Asp Leu Ser Gln Pro Tyr Pro Ile Leu Met Gln Arg
    50                  55                  60

Thr Pro Tyr Ser Ala Gly Pro Tyr Gly Pro Gly Asn Met Lys Asn Lys
65                  70                  75                  80

Leu Gly Pro Ser Gln Phe Leu Met Asn Asp Gly Tyr Ile Phe Val Tyr
                85                  90                  95

Gln Asp Val Arg Gly Arg Trp Met Ser Glu Gly Ser Tyr Asp Asn Met
            100                 105                 110

Arg Pro Thr Leu Ser Lys Ser Glu Arg Asn Ser Asn Gln Ile Asp Glu
        115                 120                 125

Ser Thr Asp Thr Tyr Asp Thr Ile Glu Trp Leu Leu Ala Asn Ile Lys
130                 135                 140

Asn His Asn Glu Lys Val Gly Leu Trp Gly Ile Ser Tyr Pro Gly Phe
145                 150                 155                 160

Tyr Ser Ala Ala Ala Leu Pro Phe Ala His Pro Asn Leu Lys Ala Val
                165                 170                 175

Ser Pro Gln Ala Pro Ile Gly Asp Phe Tyr Phe Asp Asp Phe His His
            180                 185                 190

Asn Gly Ala Tyr Leu Leu Ser Tyr Trp Leu Ala Thr Ser Val Phe Gly
        195                 200                 205

Tyr Gln Lys Asp Gly Pro Thr Gln Glu Ala Trp Tyr Gly Met Val Asn
    210                 215                 220

Pro Glu Thr Asn Asp Gly Tyr Gln Phe Phe Met Asp Met Gly Pro Leu
225                 230                 235                 240

Lys Asn Ala Asp Lys Trp Tyr Gly Glu Asp Asn Phe Phe Trp Gln Gln
                245                 250                 255

Leu Lys Asn Asn Pro Asp Tyr Asn Ala Phe Trp Gln Lys Arg Ser Ile
            260                 265                 270

Ile Pro His Leu Lys Glu Val Lys Pro Ala Val Leu Thr Val Gly Gly
        275                 280                 285
```

```
Trp Phe Asp Ala Glu Asp Leu Tyr Gly Pro Leu Thr Ile Tyr Lys Thr
        290                 295                 300

Ile Glu Lys Asn Asn Pro Glu Thr Tyr Asn Thr Ile Val Met Gly Pro
305                 310                 315                 320

Trp Ser His Gly Asp Trp Ser Arg Glu Pro Gly Ser Gln Val Ile Ser
                325                 330                 335

Asn Ile Tyr Phe Gly Asp Ser Ile Ser Thr Trp Tyr Gln Lys Asn Ile
            340                 345                 350

Glu Arg Val Phe Phe Asn His Phe Leu Lys Glu Ser Glu Asn Ser Asn
        355                 360                 365

Pro Ala Leu Pro Glu Ala Tyr Met Phe Asp Thr Gly Lys His Lys Trp
370                 375                 380

Glu Lys Phe Asp Asp Trp Pro Pro Lys Glu Ser Gln Trp Lys Ser Phe
385                 390                 395                 400

Tyr Phe Gln Glu Lys Gly Glu Leu Thr Glu Val Thr Pro Glu Gly Asn
                405                 410                 415

Arg Phe Thr Thr Tyr Val Ser Asp Pro Ser Asn Pro Val Pro Tyr Ser
            420                 425                 430

Gln Asp Ile Lys Leu Asn Phe Thr Pro Arg Lys Tyr Met Ala Asp Asp
        435                 440                 445

Gln Arg Phe Ala Ala Arg Arg Pro Asp Val Leu Thr Phe Thr Ser Glu
450                 455                 460

Val Leu Ser Gln Asp Met Thr Leu Ala Gly Glu Val Met Ala Asn Leu
465                 470                 475                 480

Lys Val Ala Thr Ser Gln Thr Asp Ala Asp Trp Val Val Lys Ile Ile
                485                 490                 495

Asp Ile Phe Pro Gly Asp Gln Pro Asn His Ala Tyr Val Leu Asp Gly
            500                 505                 510

Val Asp Met Gly Asn Tyr His Leu Met Val Arg Ser Glu Val Ile Arg
        515                 520                 525

Gly Arg Tyr Arg Glu Ser Phe Glu Phe Pro Lys Pro Phe Val Pro Asp
530                 535                 540

Gln Ile Thr Ala Val Asp Phe Arg Leu Gln Asp Leu Phe His Thr Phe
545                 550                 555                 560

Lys Lys Gly His Lys Ile Gln Ile Gln Ile Gln Ser Thr Trp Phe Pro
                565                 570                 575

Leu Ile Asp Arg Asn Pro Gln Lys Tyr Val Gln Asn Ile Phe Glu Ala
            580                 585                 590

Glu Glu Ala Asp Phe Val Lys Ala Thr His Arg Val Phe His Thr Glu
        595                 600                 605

Lys Phe Ala Ser Lys Ile Glu Val Met Val Leu Pro
610                 615                 620

<210> SEQ ID NO 26
<211> LENGTH: 2036
<212> TYPE: DNA
<213> ORGANISM: Psycloserpens burtonensis
<220> FEATURE:
<221> NAME/KEY: CDS
<222> LOCATION: (61)..(1992)
<223> OTHER INFORMATION:

<400> SEQUENCE: 26
catattcgta aaatagctat aagttttgt aaatttagtc aatcaaaatt ttaaatgtaa    60 atg aag act ctt ttt aaa ttg ttg ctc cta ttt gta ttt gtt cta acg   108
Met Lys Thr Leu Phe Lys Leu Leu Leu Leu Phe Val Phe Val Leu Thr
1               5                   10                  15
```

```
tct tgt aat aag gcc aac aaa gac gct act gaa att gtg aaa acc gaa    156
Ser Cys Asn Lys Ala Asn Lys Asp Ala Thr Glu Ile Val Lys Thr Glu
        20              25                  30 gta gaa gat act tac gtt aaa gat aat tat aac aaa caa gag gtg act    204
Val Glu Asp Thr Tyr Val Lys Asp Asn Tyr Asn Lys Gln Glu Val Thr
        35              40                  45 att gaa atg cgc gat ggt ata aaa ctt cac acg acc att tat tca cca    252
Ile Glu Met Arg Asp Gly Ile Lys Leu His Thr Thr Ile Tyr Ser Pro
50              55                  60 aaa gat gaa agt cag acc tat cct att tta atg atg aga aca cca tat    300
Lys Asp Glu Ser Gln Thr Tyr Pro Ile Leu Met Met Arg Thr Pro Tyr
65              70                  75                  80 agt tct caa cct tat ggt gac aat gag ttt aag acg aaa att ggt cct    348
Ser Ser Gln Pro Tyr Gly Asp Asn Glu Phe Lys Thr Lys Ile Gly Pro
                    85                  90                  95 aat gtt cat tta atg aaa gaa ggg aat att gtt gtg tat caa gat gta    396
Asn Val His Leu Met Lys Glu Gly Asn Ile Val Val Tyr Gln Asp Val
                100                 105                 110 cga ggt cgt tgg atg agt gaa ggt gtc tat gat aat atg cgt gct tat    444
Arg Gly Arg Trp Met Ser Glu Gly Val Tyr Asp Asn Met Arg Ala Tyr
            115                 120                 125 atc cca aat aaa aca gag gat tct caa att gat gag gca tca gac act    492
Ile Pro Asn Lys Thr Glu Asp Ser Gln Ile Asp Glu Ala Ser Asp Thr
        130                 135                 140 tat gac acg att gac tgg ctg gta aat aac gta gaa aat aat aac ggg    540
Tyr Asp Thr Ile Asp Trp Leu Val Asn Asn Val Glu Asn Asn Asn Gly
145                 150                 155                 160 aat gtt ggt act tgg gga att tca tat cct ggt ttt tat gct aca tat    588
Asn Val Gly Thr Trp Gly Ile Ser Tyr Pro Gly Phe Tyr Ala Thr Tyr
                    165                 170                 175 tct act ata gac gca cac cca gct tta aaa gca gca tcg cct caa gcg    636
Ser Thr Ile Asp Ala His Pro Ala Leu Lys Ala Ala Ser Pro Gln Ala
                180                 185                 190 tgt att gga gat ttc ttt ttt gac gat ttt cat cat aat ggt gct ttt    684
Cys Ile Gly Asp Phe Phe Phe Asp Asp Phe His His Asn Gly Ala Phe
            195                 200                 205 tta tta agt tat ttt aga gca gtg tct tta ttt ggt acg aca aaa gat    732
Leu Leu Ser Tyr Phe Arg Ala Val Ser Leu Phe Gly Thr Thr Lys Asp
        210                 215                 220 aaa cct aca gat tct gct tgg tat aag ttt cca gaa atg aaa aca caa    780
Lys Pro Thr Asp Ser Ala Trp Tyr Lys Phe Pro Glu Met Lys Thr Gln
225                 230                 235                 240 gat caa tat caa ttt ttt ctt gat gct gga cct tta agt aat ttg aac    828
Asp Gln Tyr Gln Phe Phe Leu Asp Ala Gly Pro Leu Ser Asn Leu Asn
                    245                 250                 255 aag tat ttc caa tat gac aca cca gac gac aca tct gta tcc aag tct    876
Lys Tyr Phe Gln Tyr Asp Thr Pro Asp Asp Thr Ser Val Ser Lys Ser
                260                 265                 270 gat agg ata gat gat gtg ttt tgg aaa gaa att gta gag cat cca aac    924
Asp Arg Ile Asp Asp Val Phe Trp Lys Glu Ile Val Glu His Pro Asn
            275                 280                 285 tac gat acg ata tgg aaa tct aaa ggt tta att caa aac cta aaa gat    972
Tyr Asp Thr Ile Trp Lys Ser Lys Gly Leu Ile Gln Asn Leu Lys Asp
        290                 295                 300 att aag cca agt gta gcg aca atg att gtg gga ggg tta ttt gat gcc   1020
Ile Lys Pro Ser Val Ala Thr Met Ile Val Gly Gly Leu Phe Asp Ala
305                 310                 315                 320 gaa gat tta tat ggg cca ttt gaa act tat aaa acg ata gaa aaa cat   1068
Glu Asp Leu Tyr Gly Pro Phe Glu Thr Tyr Lys Thr Ile Glu Lys His
                    325                 330                 335
```

```
aat cct gat aat tat aat att atg gtt ttt ggg cct tgg gat cat ggt    1116
Asn Pro Asp Asn Tyr Asn Ile Met Val Phe Gly Pro Trp Asp His Gly
        340                 345                 350 cgt tgg gct agg agt gac gtt aaa aat tat gtt gga aat tat ttc ttc    1164
Arg Trp Ala Arg Ser Asp Val Lys Asn Tyr Val Gly Asn Tyr Phe Phe
        355                 360                 365 gga gat tct ata tct cta aaa ttt caa cgt gat gtt gaa acg aag ttt    1212
Gly Asp Ser Ile Ser Leu Lys Phe Gln Arg Asp Val Glu Thr Lys Phe
370                 375                 380 ttt aat cat ttt tta aaa gga aaa ggc gac aag aac tca ggg tta cca    1260
Phe Asn His Phe Leu Lys Gly Lys Gly Asp Lys Asn Ser Gly Leu Pro
385                 390                 395                 400 gaa gca tat gta ttt gat tct ggt aaa aag gaa tgg agt agc ttt gac    1308
Glu Ala Tyr Val Phe Asp Ser Gly Lys Lys Glu Trp Ser Ser Phe Asp
                405                 410                 415 agc tgg cct cca aag caa gca gaa aaa caa gcc atg tat ctt aat gcc    1356
Ser Trp Pro Pro Lys Gln Ala Glu Lys Gln Ala Met Tyr Leu Asn Ala
            420                 425                 430 aac caa gag cta tca gat tca aaa aaa gga aat act agt gag aca ttt    1404
Asn Gln Glu Leu Ser Asp Ser Lys Lys Gly Asn Thr Ser Glu Thr Phe
        435                 440                 445 gtt agt gat tta aaa cgc cct gta cct tat tcc gaa gat att aaa aca    1452
Val Ser Asp Leu Lys Arg Pro Val Pro Tyr Ser Glu Asp Ile Lys Thr
450                 455                 460 gtt ttc aca cca cga aaa tac atg aca gac gat cag cgt ttt gca gca    1500
Val Phe Thr Pro Arg Lys Tyr Met Thr Asp Asp Gln Arg Phe Ala Ala
465                 470                 475                 480 cga cgt cct gat gtt ctt ata ttt gag acc gat att ctt gag gaa gat    1548
Arg Arg Pro Asp Val Leu Ile Phe Glu Thr Asp Ile Leu Glu Glu Asp
                485                 490                 495 ata acc tta gct ggt gat att tta gcg cag ctt aat gtg tca act aca    1596
Ile Thr Leu Ala Gly Asp Ile Leu Ala Gln Leu Asn Val Ser Thr Thr
            500                 505                 510 ggg aca gat gca gat tgg att gtc aaa ata gta gat gtt cat cca gca    1644
Gly Thr Asp Ala Asp Trp Ile Val Lys Ile Val Asp Val His Pro Ala
        515                 520                 525 gat gct gag gag caa aaa gaa ggt atg caa gac cat tta tca atg agt    1692
Asp Ala Glu Glu Gln Lys Glu Gly Met Gln Asp His Leu Ser Met Ser
530                 535                 540 aat tat cat ttg atg gtg agg agt gaa gtg atg cgc ggt cgt ttt aga    1740
Asn Tyr His Leu Met Val Arg Ser Glu Val Met Arg Gly Arg Phe Arg
545                 550                 555                 560 aat agt ttt gaa aac cca gag cca ttt gtg cca aac caa cca aca gat    1788
Asn Ser Phe Glu Asn Pro Glu Pro Phe Val Pro Asn Gln Pro Thr Asp
                565                 570                 575 gtc aat atc aag tta caa gat gta cat cat aca ttt aaa aaa ggt cac    1836
Val Asn Ile Lys Leu Gln Asp Val His His Thr Phe Lys Lys Gly His
            580                 585                 590 aaa tta caa gtg caa gtt cag agt acg tgg ttt cca ctt att gat ttg    1884
Lys Leu Gln Val Gln Val Gln Ser Thr Trp Phe Pro Leu Ile Asp Leu
        595                 600                 605 aac ccg caa aca ttt gtg cct aat att tat aaa gca aaa gaa agc gat    1932
Asn Pro Gln Thr Phe Val Pro Asn Ile Tyr Lys Ala Lys Glu Ser Asp
610                 615                 620 ttt aaa acc caa aca cat tcg gtt ttt aac gat tct aaa att gag ttt    1980
Phe Lys Thr Gln Thr His Ser Val Phe Asn Asp Ser Lys Ile Glu Phe
625                 630                 635                 640 acg gtt ttg aaa taagagtaga tgactaaatt tgccaaggta gatttagtct tttt   2036
Thr Val Leu Lys
```

<210> SEQ ID NO 27
<211> LENGTH: 644
<212> TYPE: PRT
<213> ORGANISM: Psycloserpens burtonensis

<400> SEQUENCE: 27

```
Met Lys Thr Leu Phe Lys Leu Leu Leu Phe Val Phe Val Leu Thr
 1               5                  10                  15

Ser Cys Asn Lys Ala Asn Lys Asp Ala Thr Glu Ile Val Lys Thr Glu
            20                  25                  30

Val Glu Asp Thr Tyr Val Lys Asp Asn Tyr Asn Lys Gln Glu Val Thr
        35                  40                  45

Ile Glu Met Arg Asp Gly Ile Lys Leu His Thr Thr Ile Tyr Ser Pro
    50                  55                  60

Lys Asp Glu Ser Gln Thr Tyr Pro Ile Leu Met Met Arg Thr Pro Tyr
 65                  70                  75                  80

Ser Ser Gln Pro Tyr Gly Asp Asn Glu Phe Lys Thr Lys Ile Gly Pro
                85                  90                  95

Asn Val His Leu Met Lys Glu Gly Asn Ile Val Val Tyr Gln Asp Val
            100                 105                 110

Arg Gly Arg Trp Met Ser Glu Gly Val Tyr Asp Asn Met Arg Ala Tyr
        115                 120                 125

Ile Pro Asn Lys Thr Glu Asp Ser Gln Ile Asp Glu Ala Ser Asp Thr
    130                 135                 140

Tyr Asp Thr Ile Asp Trp Leu Val Asn Asn Val Glu Asn Asn Asn Gly
145                 150                 155                 160

Asn Val Gly Thr Trp Gly Ile Ser Tyr Pro Gly Phe Tyr Ala Thr Tyr
                165                 170                 175

Ser Thr Ile Asp Ala His Pro Ala Leu Lys Ala Ala Ser Pro Gln Ala
            180                 185                 190

Cys Ile Gly Asp Phe Phe Phe Asp Asp Phe His His Asn Gly Ala Phe
        195                 200                 205

Leu Leu Ser Tyr Phe Arg Ala Val Ser Leu Phe Gly Thr Thr Lys Asp
    210                 215                 220

Lys Pro Thr Asp Ser Ala Trp Tyr Lys Phe Pro Glu Met Lys Thr Gln
225                 230                 235                 240

Asp Gln Tyr Gln Phe Phe Leu Asp Ala Gly Pro Leu Ser Asn Leu Asn
                245                 250                 255

Lys Tyr Phe Gln Tyr Asp Thr Pro Asp Asp Thr Ser Val Ser Lys Ser
            260                 265                 270

Asp Arg Ile Asp Asp Val Phe Trp Lys Glu Ile Val Glu His Pro Asn
        275                 280                 285

Tyr Asp Thr Ile Trp Lys Ser Lys Gly Leu Ile Gln Asn Leu Lys Asp
    290                 295                 300

Ile Lys Pro Ser Val Ala Thr Met Ile Val Gly Gly Leu Phe Asp Ala
305                 310                 315                 320

Glu Asp Leu Tyr Gly Pro Phe Glu Thr Tyr Lys Thr Ile Glu Lys His
                325                 330                 335

Asn Pro Asp Asn Tyr Asn Ile Met Val Phe Gly Pro Trp Asp His Gly
            340                 345                 350

Arg Trp Ala Arg Ser Asp Val Lys Asn Tyr Val Gly Asn Tyr Phe Phe
        355                 360                 365

Gly Asp Ser Ile Ser Leu Lys Phe Gln Arg Asp Val Glu Thr Lys Phe
    370                 375                 380
```

```
Phe Asn His Phe Leu Lys Gly Lys Gly Asp Lys Asn Ser Gly Leu Pro
385                 390                 395                 400

Glu Ala Tyr Val Phe Asp Ser Gly Lys Lys Glu Trp Ser Ser Phe Asp
                405                 410                 415

Ser Trp Pro Pro Lys Gln Ala Glu Lys Gln Ala Met Tyr Leu Asn Ala
            420                 425                 430

Asn Gln Glu Leu Ser Asp Ser Lys Lys Gly Asn Thr Ser Glu Thr Phe
            435                 440                 445

Val Ser Asp Leu Lys Arg Pro Val Pro Tyr Ser Glu Asp Ile Lys Thr
        450                 455                 460

Val Phe Thr Pro Arg Lys Tyr Met Thr Asp Asp Gln Arg Phe Ala Ala
465                 470                 475                 480

Arg Arg Pro Asp Val Leu Ile Phe Glu Thr Asp Ile Leu Glu Glu Asp
                485                 490                 495

Ile Thr Leu Ala Gly Asp Ile Leu Ala Gln Leu Asn Val Ser Thr Thr
                500                 505                 510

Gly Thr Asp Ala Asp Trp Ile Val Lys Ile Val Asp Val His Pro Ala
            515                 520                 525

Asp Ala Glu Glu Gln Lys Glu Gly Met Gln Asp His Leu Ser Met Ser
530                 535                 540

Asn Tyr His Leu Met Val Arg Ser Glu Val Met Arg Gly Arg Phe Arg
545                 550                 555                 560

Asn Ser Phe Glu Asn Pro Glu Pro Phe Val Pro Asn Gln Pro Thr Asp
                565                 570                 575

Val Asn Ile Lys Leu Gln Asp Val His His Thr Phe Lys Lys Gly His
            580                 585                 590

Lys Leu Gln Val Gln Val Gln Ser Thr Trp Phe Pro Leu Ile Asp Leu
            595                 600                 605

Asn Pro Gln Thr Phe Val Pro Asn Ile Tyr Lys Ala Lys Glu Ser Asp
            610                 615                 620

Phe Lys Thr Gln Thr His Ser Val Phe Asn Asp Ser Lys Ile Glu Phe
625                 630                 635                 640

Thr Val Leu Lys
```